United States Patent
Song et al.

(10) Patent No.: US 12,251,183 B2
(45) Date of Patent: *Mar. 18, 2025

(54) MULTI-JOINT TYPE SURGICAL DEVICE

(71) Applicant: LIVSMED INC., Seongnam-si (KR)

(72) Inventors: Youngjae Song, Seongnam-si (KR);
Jung Joo Lee, Seongnam-si (KR);
Heejin Kim, Seongnam-si (KR);
Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/651,817

(22) Filed: May 1, 2024

(65) Prior Publication Data

US 2024/0285357 A1 Aug. 29, 2024

Related U.S. Application Data

(63) Continuation of application No. 18/384,859, filed on Oct. 29, 2023, now Pat. No. 12,004,828, which is a
(Continued)

(30) Foreign Application Priority Data

Apr. 28, 2021 (KR) .......................... 10-2021-0055321

(51) Int. Cl.
*A61B 17/29* (2006.01)
*A61B 34/00* (2016.01)
(Continued)

(52) U.S. Cl.
CPC .............. *A61B 34/30* (2016.02); *A61B 17/29* (2013.01); *A61B 34/71* (2016.02);
(Continued)

(58) Field of Classification Search
CPC ......... A61B 34/30; A61B 34/71; A61B 17/29; A61B 2034/301; A61B 2034/305; A61B 2017/00477
See application file for complete search history.

(56) References Cited

U.S. PATENT DOCUMENTS 6,684,129 B2 * 1/2004 Salisbury, Jr. ......... A61B 34/30
600/595
6,728,599 B2 * 4/2004 Wang ..................... A61B 34/70
600/595
(Continued)

FOREIGN PATENT DOCUMENTS

JP  2007-167643 A  7/2007
JP  2017-513678 A  6/2017
(Continued)

OTHER PUBLICATIONS

Horigome et al., Development of a coupled tendon-driven 3D multi-joint manipulator, 2014, IEEE, p. 5915-5920 (Year: 2014).*
(Continued)

*Primary Examiner* — McDieunel Marc
(74) *Attorney, Agent, or Firm* — Bridgeway IP Law Group, PLLC; Sang Ho Lee; Hyun Woo Shin

(57) ABSTRACT

A multi-joint type surgical device includes a driving part configured to control a pitch rotation of an end tool. The driving part includes a driving part pitch relay pulley formed such that at least a portion of a wire is wound therearound and a driving part pitch satellite pulley that changes a position thereof relative to the driving part pitch relay pulley by moving relative to the driving part pitch relay pulley while being spaced a certain distance from the driving part pitch relay pulley, and is formed such that at least a portion of the wire is wound therearound, and when the driving part pitch satellite pulley is moved relative to the driving part
(Continued)

pitch relay pulley, the pitch rotation of the end tool is controlled as an overall length of the wire in the driving part is changed.

19 Claims, 33 Drawing Sheets

Related U.S. Application Data continuation of application No. PCT/KR2022/006086, filed on Apr. 28, 2022.

(51) Int. Cl.
*A61B 34/30* (2016.01)
*A61B 17/00* (2006.01)

(52) U.S. Cl.
CPC ............... *A61B 2017/00477* (2013.01); *A61B 2034/301* (2016.02); *A61B 2034/306* (2016.02)

(56) References Cited

U.S. PATENT DOCUMENTS

| | | | | |
|---|---|---|---|---|
| 6,839,612 | B2* | 1/2005 | Sanchez | A61B 34/35 606/1 |
| 7,155,316 | B2* | 12/2006 | Sutherland | A61B 34/37 901/1 |
| 7,379,790 | B2* | 5/2008 | Toth | A61B 34/30 901/33 |
| 7,386,365 | B2* | 6/2008 | Nixon | A61B 34/37 606/139 |
| 8,992,565 | B2 | 3/2015 | Brisson et al. | |
| 9,089,353 | B2 | 7/2015 | Farritor et al. | |
| 9,770,305 | B2 | 9/2017 | Farritor et al. | |
| 10,582,973 | B2 | 3/2020 | Wilson et al. | |
| 2002/0032451 | A1 | 3/2002 | Tierney et al. | |
| 2002/0087169 | A1 | 7/2002 | Brock et al. | |
| 2010/0011900 | A1 | 1/2010 | Burbank | |
| 2011/0066161 | A1 | 3/2011 | Cooper | |
| 2017/0042560 | A1 | 2/2017 | Lee et al. | |
| 2019/0069967 | A1 | 3/2019 | Crews et al. | |
| 2019/0090965 | A1 | 3/2019 | Farritor et al. | |
| 2019/0328467 | A1 | 10/2019 | Waterbury | |
| 2020/0138534 | A1 | 5/2020 | Garcia Kilroy et al. | |
| 2020/0214775 | A1 | 7/2020 | Farritor et al. | |
| 2023/0372039 | A1 | 11/2023 | Panescu et al. | |
| 2024/0000527 | A1 | 1/2024 | Girardeau-Montaut et al. | |
| 2024/0004369 | A1 | 1/2024 | Agrawal et al. | |

FOREIGN PATENT DOCUMENTS

| | | |
|---|---|---|
| KR | 10-2008-0087111 A | 9/2008 |
| KR | 10-2016-0008169 A | 1/2016 |
| KR | 10-2018-0022945 A | 3/2018 |
| KR | 10-2021-0024484 A | 3/2021 |

OTHER PUBLICATIONS

Lee et al., Design and Evaluation of Cable-driven Manipulator with Motion-decoupled Joints, 2008, IEEE, p. 275-580 (Year: 2008).*
Kim et al., A study for the dynamic system of coupled cable-driven structure in surgical robot instrument, 2011, IEEE, p. 339-343 (Year: 2011).*
Fujioka et al., Proposal of tendon-driven elastic telescopic arm and initial bending experiment, 2017, IEEE, p. 164-169 (Year: 2017 ).*
Hongbing Li et al., "Development of a human-arm like laparoscopic instrument," 2016, IEEE, p. 68-70 (Year: 2016).
Yusheng Yan et al., "UFK-Based motion estimation of cable-driven forceps for robot-assisted surgical system," 2020, IEEE, p. 94912-94922 (Year: 2020).
Lin Cao et al., "Sewing up the wounds: a robotic suturing system for flexible endoscopy," 2020, IEEE, p. 45-54 (Year: 2020).
Lin Cao et al., "A novel robotic suturing system for flexible endoscopic surgery," 2019, IEEE, p. 1514-1520 (Year: 2019).
European Patent Office, Extended European Search Report issued on Oct. 18, 2024, for counterpart European Application No. 22796169.5.

* cited by examiner

FIG. 15
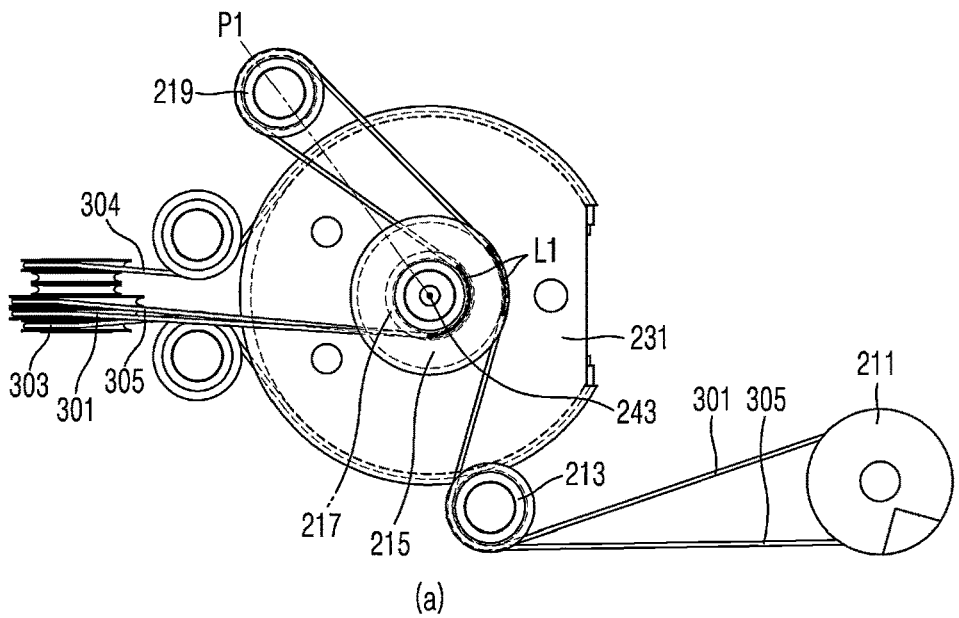
(a)
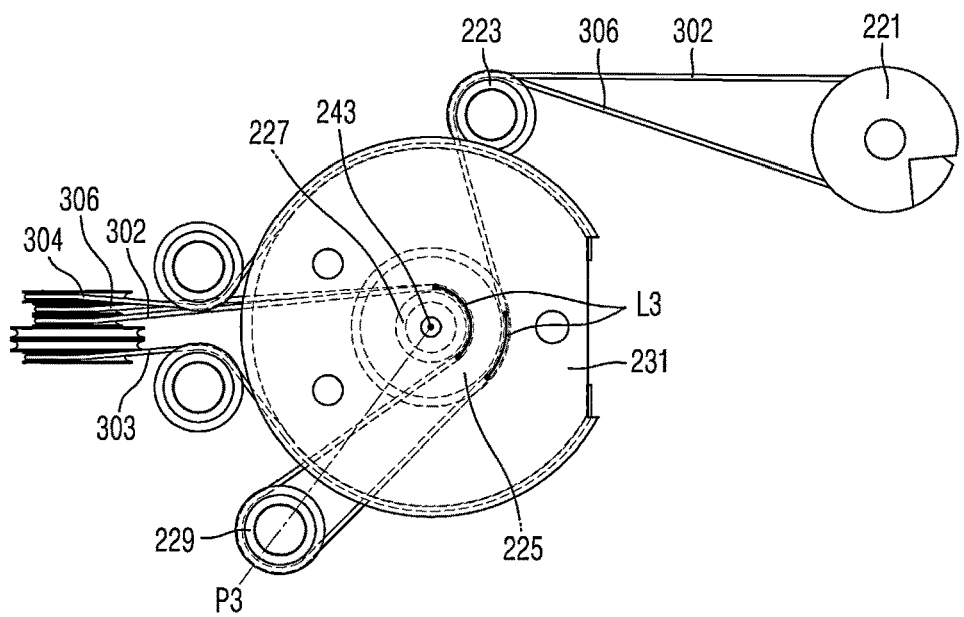
(b)
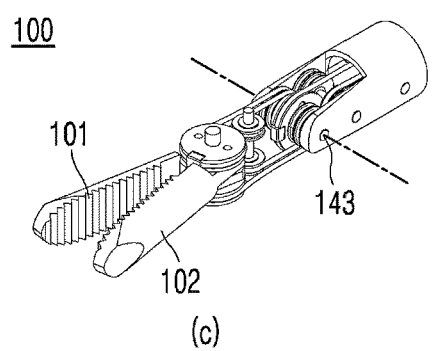
(c)

FIG. 16
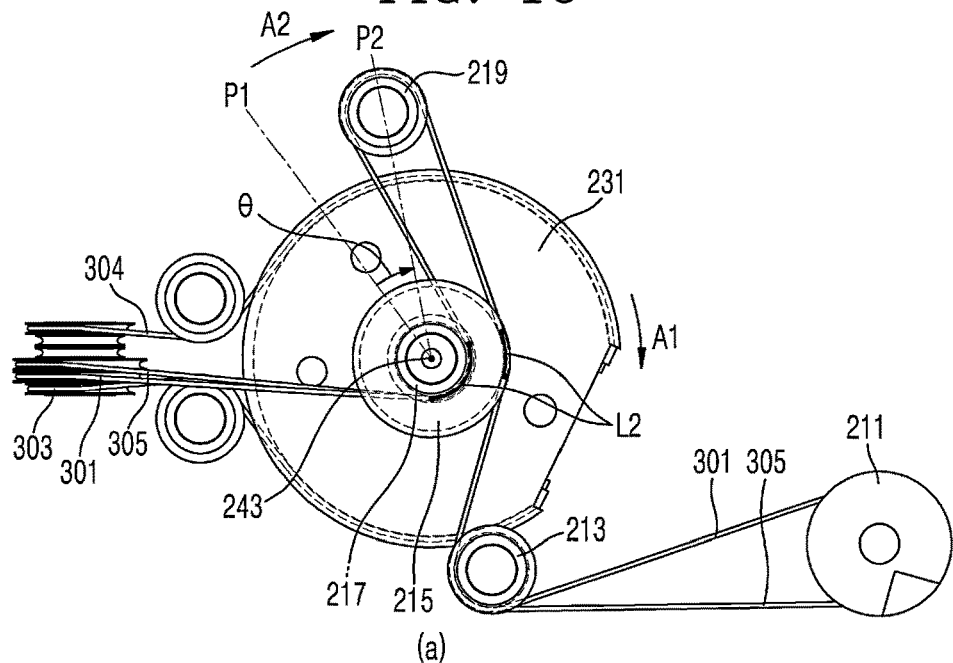
(a)
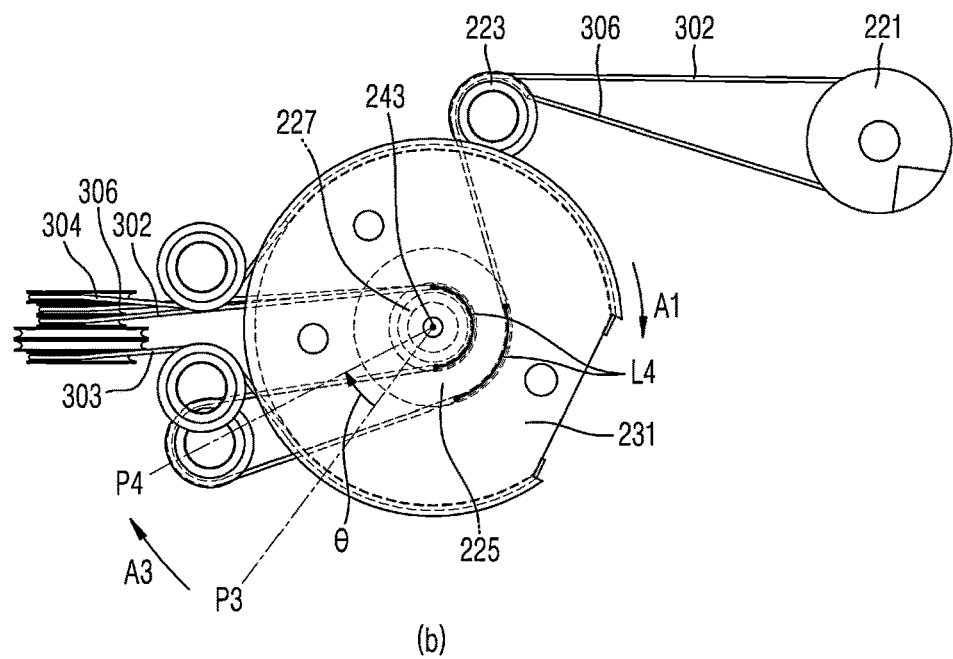
(b)
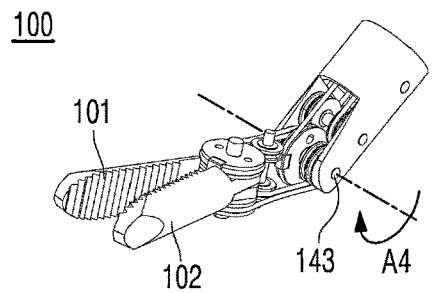
(c)

FIG. 17
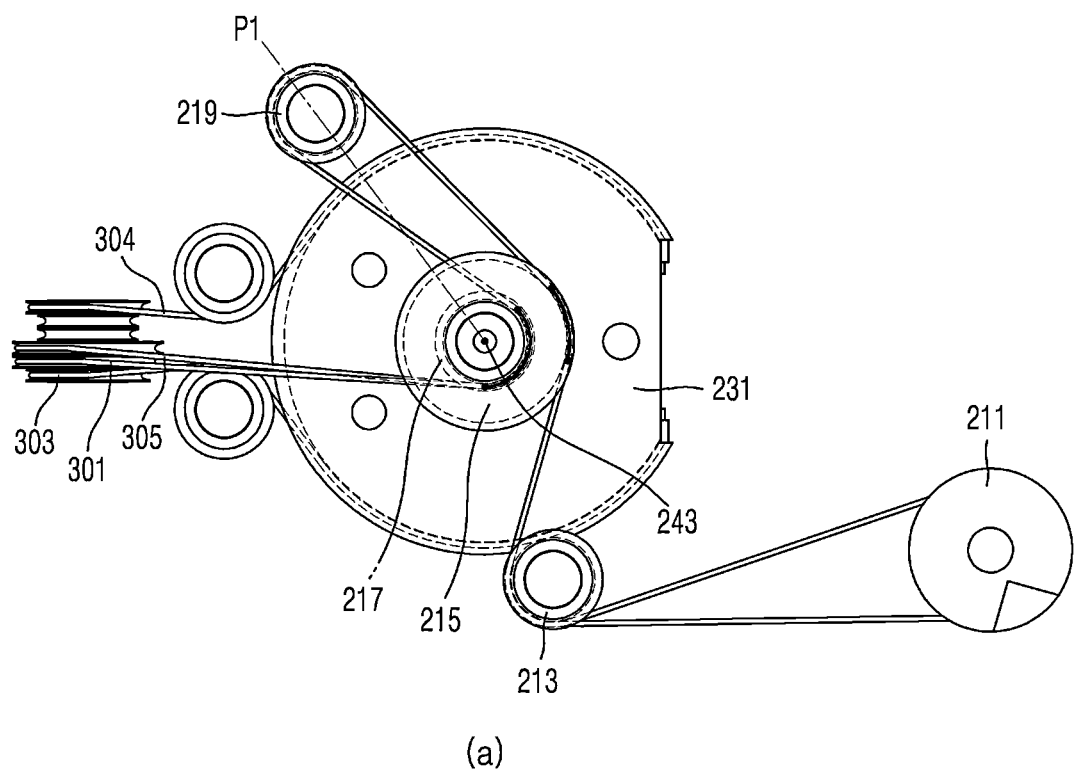
(a)
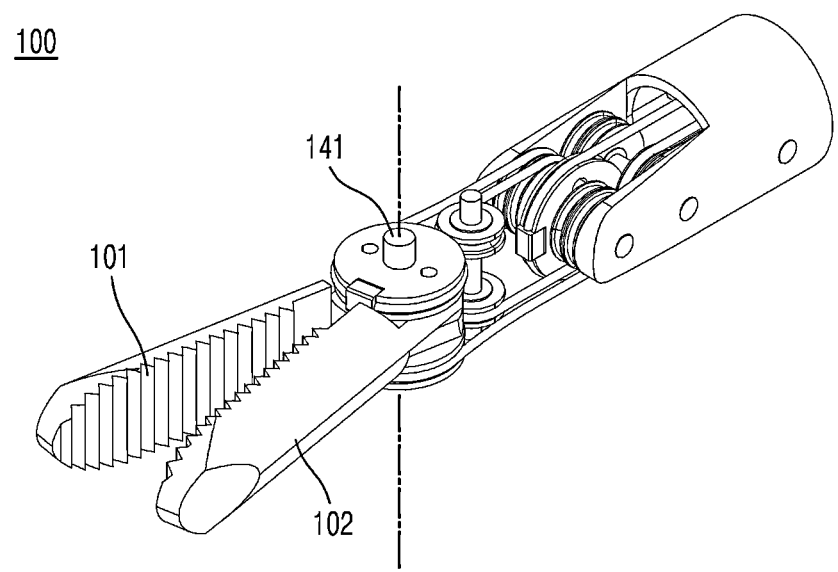
(b)

FIG. 18
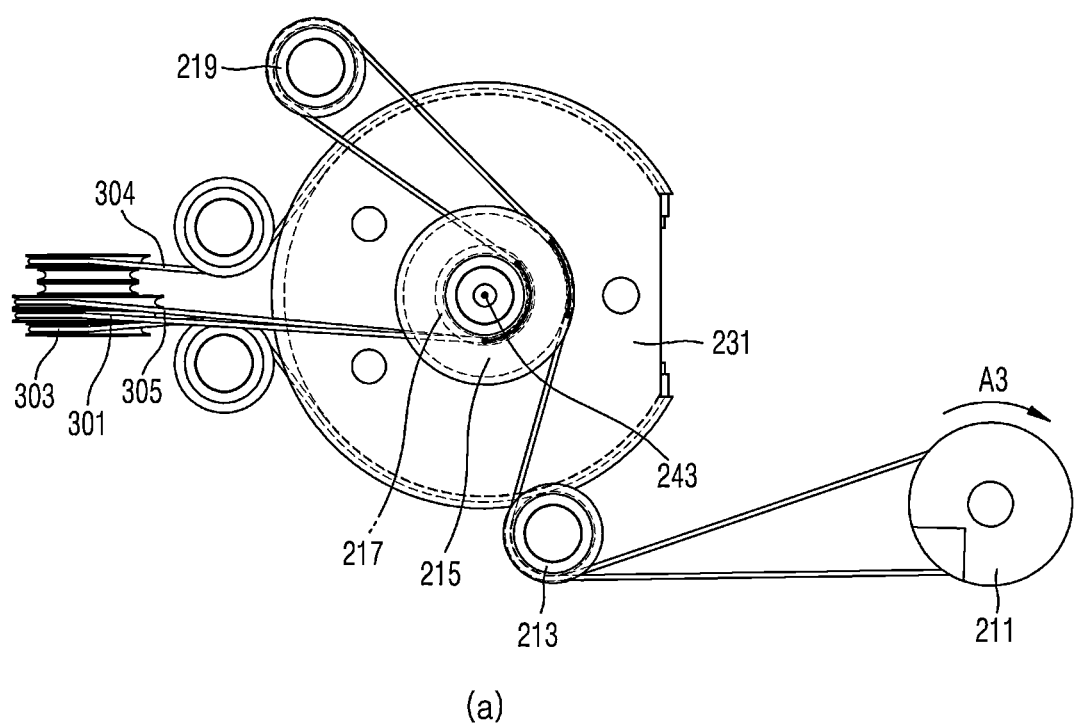
(a)
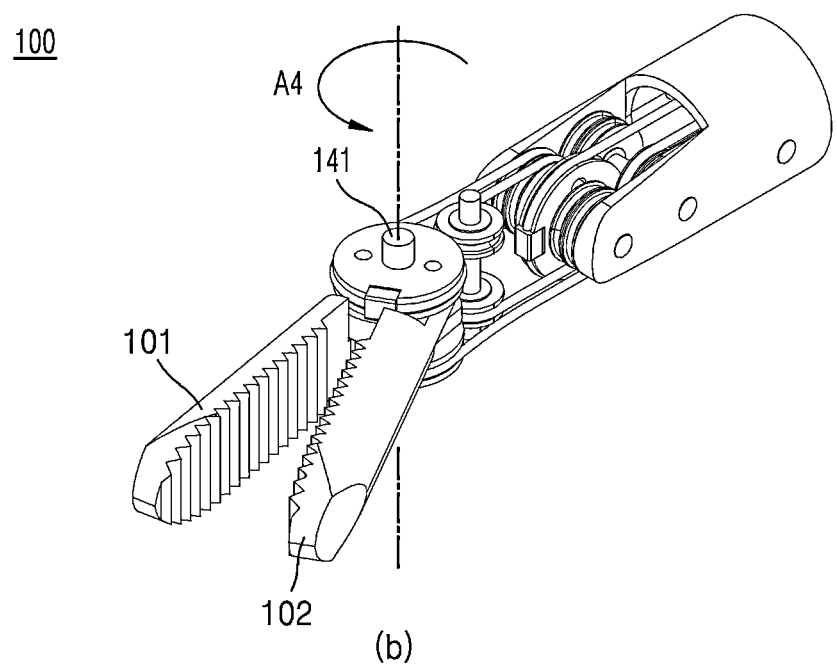
(b)

MULTI-JOINT TYPE SURGICAL DEVICE

CROSS-REFERENCE TO RELATED APPLICATION

This application is a continuation application of U.S. Ser. No. 18/384,859 filed on Oct. 29, 2023, which is a bypass continuation application of international application No. PCT/KR2022/006086 filed on Apr. 28, 2022, which claims priority to Korean Patent Application No. 10-2021-0055321, filed on Apr. 28, 2021, with the Korean Intellectual Property Office, the disclosures of which are incorporated herein in their entirety by reference.

TECHNICAL FIELD

The present disclosure relates to a multi-joint type surgical device, and more particularly, to a multi-joint type surgical device capable of being mounted on a robot arm or operated manually for use in laparoscopic surgery or various surgeries.

BACKGROUND ART

Medically, surgery refers to the treatment of diseases by cutting, slitting, or manipulating the skin, mucous membranes, or other tissues using medical devices In particular, open surgery in which the skin of the surgical site is incised and opened to treat, shape, remove organs or the like therein and the like cause problems such as bleeding, side effects, patient pain, scarring. Accordingly, recently, surgery performed by inserting only a medical device, for example, laparoscopic surgical instrument, microsurgical microscope, and the like by forming a predetermined hole in the skin or surgery using a robot has been spotlighted as an alternative.

Here, a surgical robot refers to a robot that has a function of replacing a surgical action performed by a surgeon. Advantageously, the surgical robot may operate more accurately and precisely as compared with a human and enable remote operation.

Surgical robots that are currently being developed worldwide may include a bone surgical robot, a laparoscopic surgical robot, a stereotactic surgical robot, and the like. Here, the laparoscopic surgical robot is a robot that performs minimum invasive surgery using a laparoscope and small surgical instruments.

Laparoscopic surgery is a cutting-edge surgery technique that involves perforating one or more small holes in the abdomen and inserting a laparoscope, which is an endoscope for looking inside the abdomen to perform the surgery, and is a field that is expected to advance in the future. Today's laparoscopes are mounted with computer chips and have been developed to the extent that magnified images, which are clearer than images seen with the naked eye, can be obtained and when used with specially-designed laparoscopic surgical tools while looking at a monitor screen, any type of surgery is possible.

Moreover, laparoscopic surgery offers the same range of surgical procedures as open surgery, but with several advantages including fewer complications, the ability to initiate treatment shortly after the procedure, and the capability to maintain the patient's stamina and immune functions. As a result, laparoscopic surgery is becoming increasingly recognized as the standard surgery for treating colorectal cancer or the like in places such as the United States and Europe.

Meanwhile, a surgical robot is generally composed of a master robot and a slave robot. When a surgical operator manipulates a control lever (e.g., a handle) equipped on the master robot, a surgical tool coupled to or held by a robot arm on the slave robot may be manipulated to perform surgery.

DESCRIPTION OF EMBODIMENTS

Technical Problem

The present disclosure is directed to providing a multi-joint type surgical device capable of being mounted on a robot arm or operated manually for use in laparoscopic surgery or various surgeries, the multi-joint type surgical device capable of independently and smoothly performing a pitch motion and a yaw motion/actuation motion by compensating for jaw wire movement that occurs during the pitch motion.

Technical Solution to Problem

One aspect of the present disclosure provides a multi-joint type surgical device including an end tool including one or more jaws and an end tool jaw pulley coupled to the jaws and formed to be rotatable together with the jaws around a first shaft, the end tool being formed to allow at least pitch rotation and yaw rotation, a jaw wire coupled to the end tool jaw pulley and moved in response to rotation of the end tool jaw pulley, a connection part formed to extend in one direction, having the jaw wire passing therethrough, and having one end portion to which the end tool is coupled, and a driving part coupled to the other end portion of the connection part and configured to control the pitch rotation and the yaw rotation of the end tool, wherein the driving part includes a driving part jaw pulley formed to be rotatable around a second shaft, and coupled to the jaw wire, a driving part relay pulley formed adjacent to the driving part jaw pulley, formed to rotate around a shaft fixed in position, and formed such that at least a portion of the jaw wire is wound therearound, and a driving part satellite pulley formed adjacent to the driving part relay pulley, formed to be movable relative to the driving part relay pulley so that a position thereof relative to the driving part relay pulley is changed, and formed such that at least a portion of the jaw wire is wound therearound, the end tool jaw pulley and the jaw are rotated while the jaw wire is moved in response to the rotation of the driving part jaw pulley, two strands of the jaw wire, which emerge while being wound around the driving part jaw pulley, extend toward the end tool after being sequentially wound around the driving part relay pulley, the driving part satellite pulley, and the driving part relay pulley, and when the driving part satellite pulley is moved relative to the driving part relay pulley, an overall length of the jaw wire in the driving part is changed so that the end tool performs the pitch rotation.

Advantageous Effects of Disclosure

According to the present disclosure, a pitch motion and a yaw motion/actuation motion can be smoothly performed independently by compensating for jaw wire movement occurring during the pitch motion.

BRIEF DESCRIPTION OF DRAWINGS

FIGS. 15 and 16 are views illustrating a pitch motion of the multi-joint type surgical device illustrated in FIG. 4.

FIGS. 17 and 18 are views illustrating a yaw motion of the multi-joint type surgical device illustrated in FIG. 4.

BEST MODE

Figure 1:
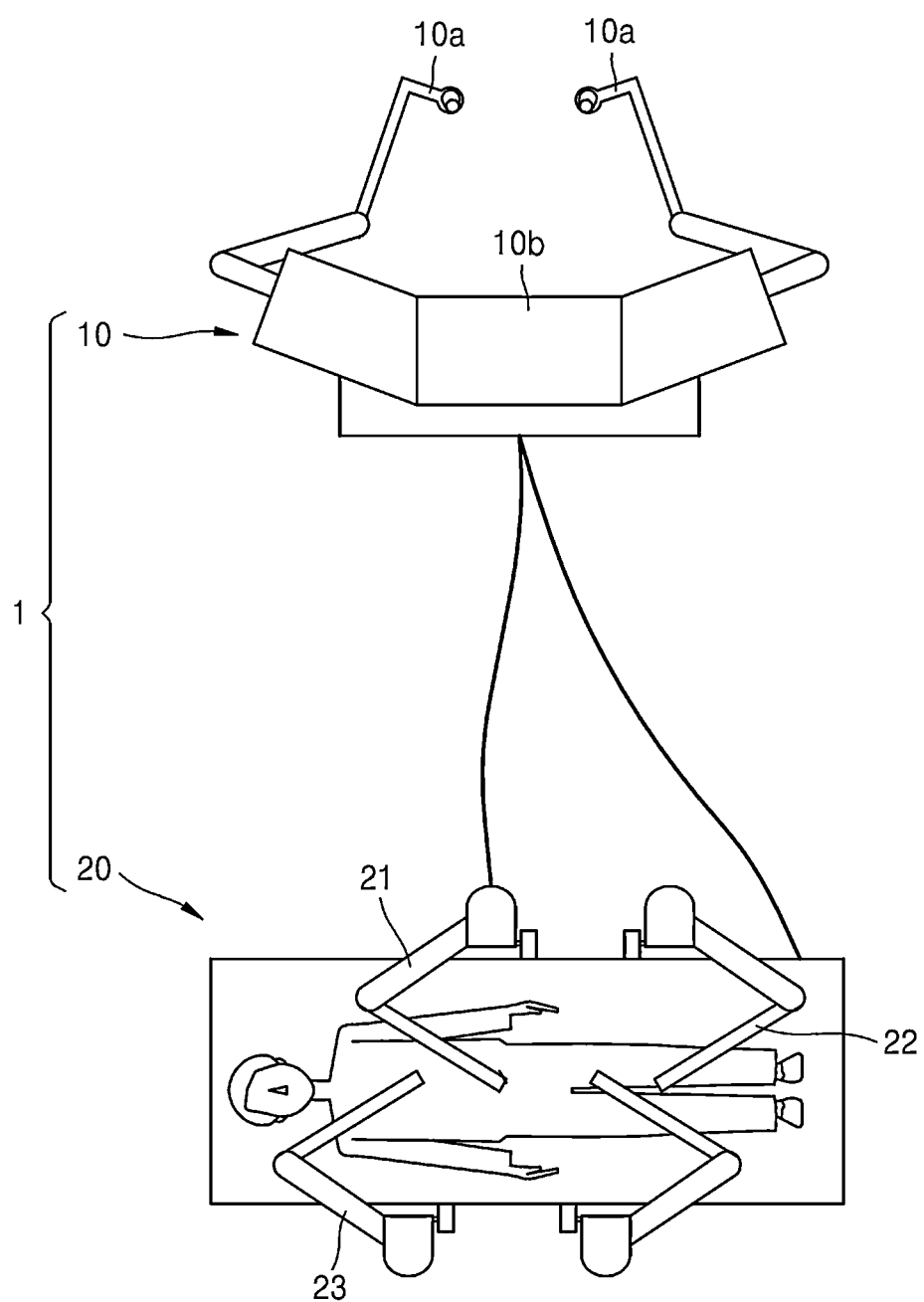
FIG. 1 is a conceptual diagram illustrating a surgical robot system to which a multi-joint type surgical device according to an embodiment of the present disclosure is mounted.

An embodiment of the present disclosure provides a multi-joint type surgical device including an end tool including one or more jaws and an end tool jaw pulley coupled to the jaws and formed to be rotatable together with the jaws around a first shaft, the end tool being formed to allow at least pitch rotation and yaw rotation, a jaw wire coupled to the end tool jaw pulley and moved in response to rotation of the end tool jaw pulley, a connection part formed to extend in one direction, having the jaw wire passing therethrough, and having one end portion to which the end tool is coupled, and a driving part coupled to the other end portion of the connection part and configured to control the pitch rotation and the yaw rotation of the end tool, wherein the driving part includes a driving part jaw pulley formed to be rotatable around a second shaft, and coupled to the jaw wire, a driving part relay pulley formed adjacent to the driving part jaw pulley, formed to rotate around a shaft fixed in position, and formed such that at least a portion of the jaw wire is wound therearound, and a driving part satellite pulley formed adjacent to the driving part relay pulley, formed to be movable relative to the driving part relay pulley so that a position thereof relative to the driving part relay pulley is changed, and formed such that at least a portion of the jaw wire is wound therearound, the end tool jaw pulley and the jaw are rotated while the jaw wire is moved in response to the rotation of the driving part jaw pulley, two strands of the jaw wire, which emerge while being wound around the driving part jaw pulley, extend toward the end tool after being sequentially wound around the driving part relay pulley, the driving part satellite pulley, and the driving part relay pulley, and when the driving part satellite pulley is moved relative to the driving part relay pulley, an overall length of the jaw wire in the driving part is changed so that the end tool performs the pitch rotation.

In an embodiment of the present disclosure, the multi-joint type surgical device may further include a driving part pitch pulley disposed adjacent to the driving part jaw pulley and formed to be rotatable around a third shaft different from the second shaft, wherein the driving part satellite pulley may be formed to be movable relative to the driving part pitch pulley, and when the driving part pitch pulley is rotated, a relative position of the driving part satellite pulley with respect to the driving part pitch pulley may be changed.

In an embodiment of the present disclosure, a relative position of the driving part pitch pulley with respect to the driving part relay pulley may remain constant.

In an embodiment of the present disclosure, when the driving part pitch pulley is rotated, the driving part satellite pulley may be moved in conjunction with the driving part pitch pulley.

In an embodiment of the present disclosure, when the driving part pitch pulley is rotated around the third shaft, the overall length of the jaw wire in the driving part may be changed as the driving part satellite pulley is moved relative to the driving part pitch pulley.

In an embodiment of the present disclosure, due to the change in the overall length of the jaw wire in the driving part caused by the rotation of the driving part pitch pulley, an overall length of the jaw wire in the end tool may also be changed.

In an embodiment of the present disclosure, even when the overall length of the jaw wire in the driving part is changed due to the rotation of the driving part pitch pulley, an overall length of the jaw wire may remain constant.

In an embodiment of the present disclosure, the multi-joint type surgical device may further include an end tool jaw pitch main pulley formed adjacent to the end tool jaw pulley and formed to be rotatable around a fourth shaft different from the first shaft, and an end tool jaw pitch sub-pulley formed adjacent to the end tool jaw pitch main pulley and formed to be rotatable around a fifth shaft different from the first shaft.

In an embodiment of the present disclosure, when the end tool is pitch-rotated, two strands of the jaw wire emerging while being wound around the end tool jaw pulley and passing through the end tool jaw pitch main pulley and the end tool jaw pitch sub-pulley may be simultaneously moved in the same direction.

In an embodiment of the present disclosure, on the basis of one plane perpendicular to the first shaft and including the fourth shaft, two strands of the jaw wire, which emerge while being wound around the end tool jaw pulley, may be disposed on the same side with respect to the one plane.

In an embodiment of the present disclosure, the jaws may include a first jaw and a second jaw, the end tool jaw pulley may include an end tool first jaw pulley coupled to the first jaw and an end tool second jaw pulley coupled to the second jaw, and the jaw wire may include a first jaw wire coupled to the end tool first jaw pulley and a second jaw wire coupled to the end tool second jaw pulley.

In an embodiment of the present disclosure, on the basis of a plane perpendicular to the first shaft and including the fourth shaft, two strands of the first jaw wire, which emerge while being wound around the end tool first jaw pulley, may be disposed on one side with respect to the plane, and two strands of the second jaw wire, which emerge while being wound around the end tool second jaw pulley, may be disposed on the other side with respect to the plane.

In an embodiment of the present disclosure, the jaw wire may be formed to be sequentially in contact with the end tool jaw pulley, the end tool jaw pitch main pulley, and the end tool jaw pitch sub-pulley.

In an embodiment of the present disclosure, the multi-joint type surgical device may further include an end tool pitch pulley disposed adjacent to the end tool jaw pulley and formed to be rotatable around the fourth shaft or the fifth shaft, and a pitch wire coupled to each of the end tool pitch pulley and the driving part pitch pulley and configured to connect the end tool pitch pulley and the driving part pitch pulley.

In an embodiment of the present disclosure, a rotation amount of the driving part pitch pulley and a rotation amount of the end tool pitch pulley may be substantially equal to each other.

In an embodiment of the present disclosure, a ratio of a diameter of the end tool pitch pulley to a diameter of the end tool jaw pitch main pulley may be substantially equal to a ratio of a diameter of the driving part pitch pulley to a diameter of the driving part relay pulley.

In an embodiment of the present disclosure, when the driving part pitch pulley is rotated by a first angle, the driving part satellite pulley may be revolved by the first angle, and when the driving part pitch pulley is rotated by the first angle, the end tool pitch pulley and the end tool jaw pitch main pulley may be rotated by a second angle.

In an embodiment of the present disclosure, the driving part relay pulley may include a driving part first relay pulley and a driving part second relay pulley, and the jaw wire sequentially may pass through the driving part first relay pulley, the driving part satellite pulley, and the driving part second relay pulley.

In an embodiment of the present disclosure, when the driving part pitch pulley is rotated, a path length of the jaw wire from a point of entry into the driving part first relay pulley to a point of exit from the driving part second relay pulley through the driving part satellite pulley may be changed.

In an embodiment of the present disclosure, when the driving part pitch pulley is rotated, on an arrangement path of the jaw wire connecting the end tool jaw pulley and the driving part jaw pulley, a path length of the jaw wire from a point at which the jaw wire is initially in contact with the driving part relay pulley to a point at which the jaw wire is finally in contact with the driving part relay pulley may be changed.

In an embodiment of the present disclosure, a diameter of the driving part first relay pulley and a diameter of the driving part second relay pulley may be equal to each other.

In an embodiment of the present disclosure, a diameter of the driving part first relay pulley and a diameter of the driving part second relay pulley may be different from each other.

In an embodiment of the present disclosure, a diameter of the driving part relay pulley may be equal to a sum of a diameter of the driving part first relay pulley and a diameter of the driving part second relay pulley.

In an embodiment of the present disclosure, the driving part relay pulley may be formed to be rotatable around the third shaft, and the driving part satellite pulley may be formed to be revolvable around the third shaft.

In an embodiment of the present disclosure, when the driving part pitch pulley is rotated around the third shaft, the overall length of the jaw wire in the driving part may be changed as the driving part satellite pulley connected to the driving part pitch pulley is revolved around the third shaft.

In an embodiment of the present disclosure, when the driving part pitch pulley is rotated around the third shaft, the driving part satellite pulley may be rotated around the third shaft as a whole while maintaining a constant distance between a rotation axis of the driving part satellite pulley and the third shaft, in a state in which the rotation axis of the driving part satellite pulley is spaced apart from the third shaft by a certain extent.

In an embodiment of the present disclosure, the multi-joint type surgical device may further include a pitch-yaw connector formed to rotate together with the driving part pitch pulley around the third shaft, wherein the driving part satellite pulley may be formed on at least one end portion of the pitch-yaw connector.

In an embodiment of the present disclosure, the pitch-yaw connector may include two or more extension portions formed to extend from the center thereof, and a driving part satellite pulley central shaft may be formed at an end portion of each of at least some of the extension portions.

In an embodiment of the present disclosure, the pitch-yaw connector may rigidly connect the driving part pitch pulley and the driving part satellite pulley, and when the driving part pitch pulley is rotated around the third shaft, the driving part satellite pulley may be revolved around the third shaft.

In an embodiment of the present disclosure, when the driving part satellite pulley is revolved around the third shaft, a length of the jaw wire wound around the driving part relay pulley may be changed.

In an embodiment of the present disclosure, the multi-joint type surgical device may further include a driving part pitch gear formed to rotate together with the driving part pitch pulley around the third shaft, and a compensation gear formed on one side of the driving part pitch gear so as to be engaged with the driving part pitch gear.

In an embodiment of the present disclosure, when the driving part pitch pulley performs a rotational motion, the compensation gear formed to be engaged with the driving part pitch gear may perform a linear motion.

In an embodiment of the present disclosure, the driving part satellite pulley may be disposed on the compensation gear and may perform a linear motion together with the compensation gear.

In an embodiment of the present disclosure, a length of the jaw wire wound around the driving part relay pulley may remain constant even when the driving part satellite pulley performs the linear motion.

In an embodiment of the present disclosure, the compensation gear may serve as a rack, and the driving part pitch gear may serve as a pinion.

In an embodiment of the present disclosure, the overall length of the jaw wire in the driving part may remain constant even when the driving part jaw pulley is rotated.

In an embodiment of the present disclosure, the jaw wire may be coupled to each of the end tool jaw pulley and the driving part jaw pulley to form a closed loop as a whole.

In an embodiment of the present disclosure, each of the driving part relay pulley and the driving part satellite pulley may be formed as a pair of two pulleys, so that the two strands of the jaw wire, which emerge while being wound around the driving part jaw pulley, are respectively wound around the pair of two pulleys.

In an embodiment of the present disclosure, the yaw rotation may be a motion in which the end tool jaw pulley is rotated around the first shaft, and the pitch rotation may be a motion in which the end tool jaw pulley is revolved around a fourth shaft different from the first shaft.

Another embodiment of the present disclosure provides a multi-joint type surgical device including an end tool including one or more end tool pulleys and formed to allow at least pitch rotation, a wire coupled to the end tool pulley and moved in response to rotation of the end tool pulley, a connection part formed to extend in one direction, having the wire passing therethrough, and having one end portion to which the end tool is coupled, and a driving part coupled to the other end portion of the connection part and configured to control the pitch rotation of the end tool, wherein the driving part includes a driving part driving pulley formed to be rotatable around a second shaft, and coupled to the wire, a driving part relay pulley formed adjacent to the driving part driving pulley, formed to rotate around a shaft fixed in position, and formed such that at least a portion of the wire is wound therearound, and a driving part satellite pulley formed adjacent to the driving part relay pulley, formed to be movable relative to the driving part relay pulley so that a position thereof relative to the driving part relay pulley is changed, and formed such that at least a portion of the wire is wound therearound, the end tool pulley is rotated while the wire is moved in response to the rotation of the driving part driving pulley, two strands of the wire, which emerge while being wound around the driving part driving pulley, extend toward the end tool after being sequentially wound around the driving part relay pulley, the driving part satellite pulley, and the driving part relay pulley, and when the driving part satellite pulley is moved relative to the driving part relay pulley, an overall length of the wire in the driving part is changed so that the end tool performs the pitch rotation.

Other aspects, features, and advantages other than those described above will become apparent from the following drawings, claims, and detailed description of the disclosure.

MODE OF DISCLOSURE

While the present disclosure is susceptible to various modifications and alternative forms, specific embodiments thereof are shown by way of example in the drawings and will herein be described in detail. However, it should be understood that there is no intent to limit the present disclosure to the particular forms disclosed herein, rather, the present disclosure should be construed to cover various modifications, equivalents, and alternatives of embodiments of the present disclosure. In describing the present disclosure, a detailed description of known related arts will be omitted when it is determined that the gist of the present disclosure may be unnecessarily obscured Although terms such as "first", "second", and the like may be used to describe various components, such components should not be limited to the above terms The terms are only used to distinguish one component from another.

The terms used herein are for the purpose of describing particular embodiments only and are not intended to be limiting to the present disclosure. Singular forms are intended to include plural forms as well, unless the context clearly indicates otherwise. In the present application, it will be further understood that the terms "comprise", "comprising", "include", and/or "including", when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

Figure 2:
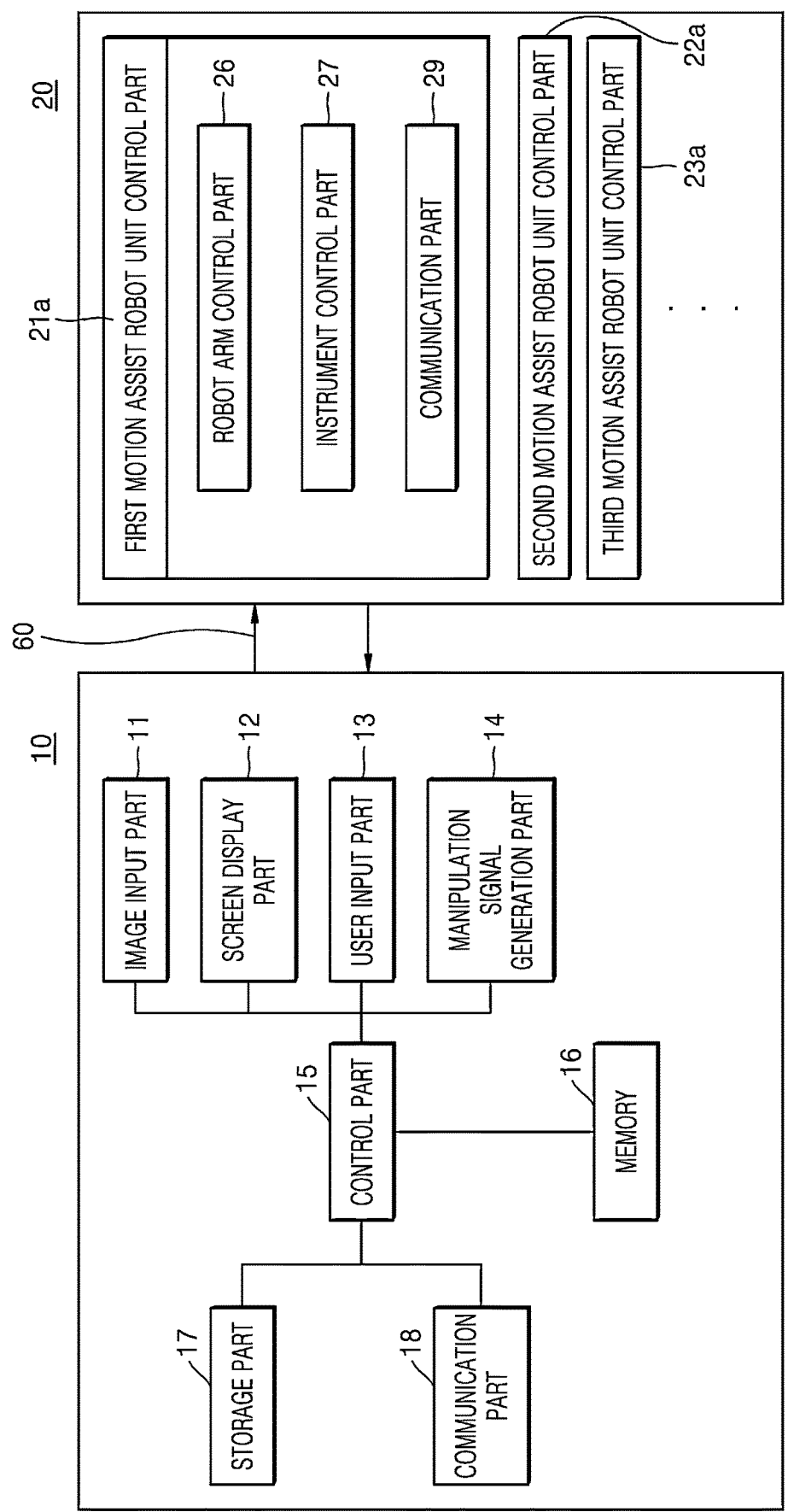
FIG. 2 is a block diagram illustrating an internal configuration of the surgical robot system of FIG. 1.
Figure 3:
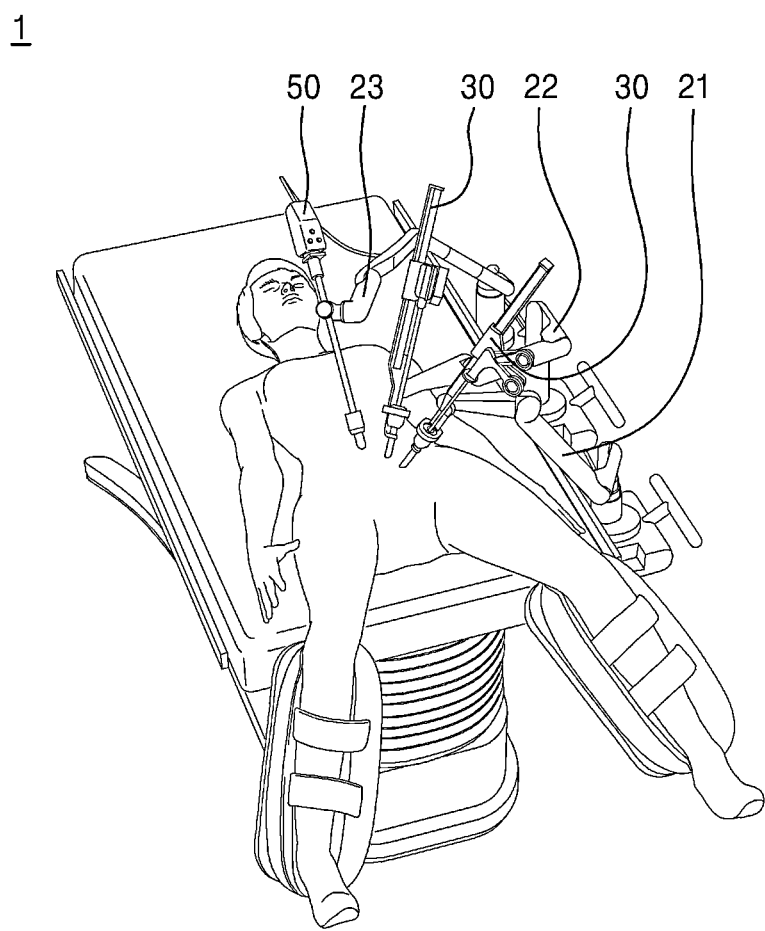
FIG. 3 is a perspective view illustrating a slave robot of the surgical robot system of FIG. 1 and the multi-joint type surgical device mounted thereto.

FIG. 1 is a conceptual diagram illustrating a surgical robot system to which a multi-joint type surgical device according to an embodiment of the present disclosure is mounted, FIG. 2 is a block diagram illustrating an internal configuration of the surgical robot system of FIG. 1, and FIG. 3 is a perspective view illustrating a slave robot of the surgical robot system of FIG. 1 and the multi-joint type surgical device mounted thereto.

Referring to FIGS. 1 to 3, a surgical robot system 1 includes a master robot 10, a slave robot 20, and a multi-joint type surgical device 30.

The master robot 10 includes manipulating members 10*a* and a display member 10*b*, and the slave robot 20 includes one or more robot arm units 21, 22, and 23.

In detail, the master robot 10 includes the manipulating members 10*a* so that a surgical operator can grip and manipulate them respectively with both hands. The manipulating members 10*a* may be implemented as two or more handles as illustrated in FIG. 1, and manipulation signals according to the handle manipulation of the surgical operator are transmitted to the slave robot 20 through a wired or wireless communication network so that the robot arm units 21, 22, and 23 are controlled. That is, surgical motions such as positioning, rotation, and cutting operations of the robot arm units 21, 22, and 23 may be performed by the handle manipulation of the surgical operator.

For example, the surgical operator may manipulate the robot arm units 21, 22, and 23 using manipulation levers in the form of a handle. The manipulation lever as described above may have various mechanical configurations according to the manipulate method thereof, and may be provided in various configurations for operating the robot arm units 21, 22, and 23 of the slave robot 20 and/or other surgical instruments, such as a master handle manipulating the motion of each of the robot arm units 21, 22, and 23 and various input tools added to the master robot 10 for manipulating the functions of the entire system such as joystick, keypad, trackball, foot pedal, and touch screen. Here, the manipulating member 10*a* is not limited to the shape of a handle and can be applied without any limitation as long as it can control motions of the robot arm units 21, 22, and 23 through a network such as a wired or wireless communication network.

Alternatively, a voice input or a motion input may also be applied for user input. That is, a user may wear, on the head thereof, glasses or a head mount display (HMD), to which a sensor attached, and a laparoscope 50 may move according to a direction in which the user's gaze. Alternatively, when the user issues a command with voice, such as "left", "right", "first arm", "second arm", and the like, the voice command may be recognized and the motion may be performed.

An image captured through the laparoscope 50 to be described later is displayed as a screen image on the display member 10*b* of the master robot 10. In addition, a predetermined virtual manipulation plate may be displayed independently or displayed together with the image captured by the laparoscope 50 on the display member 10*b*. A detailed description of the arrangement, configuration, and the like of such a virtual manipulation plate will be omitted.

Here, the display member 10*b* may include one or more monitors, each of which may individually display information necessary for surgery. The quantity of monitors may be variously determined depending on the type or kind of information that needs to be displayed.

Meanwhile, the slave robot 20 may include one or more robot arm units 21, 22, and 23. Here, each of the robot arm units 21, 22, and 23 may be provided in the form of a module that can operate independently of each other, and in this case, an algorithm for preventing a collision between the robot arm units 21, 22, and 23 may be applied to the surgical robot system 1.

In general, a robot arm refers to a device having a function similar to that of the arm and/or the wrist of a human being and having a wrist portion to which a predetermined tool may be attached. In the present specification, the robot arm units 21, 22, and 23 may each be defined as a concept encompassing all of the components such as an upper arm, a lower arm, a wrist, and an elbow, a multi-joint type surgical device coupled to the wrist portion, and the like. Alternatively, the robot arm unit may also be defined as a concept that includes only components for driving the multi-joint type surgical device, excluding the multi-joint type surgical device coupled to the wrist portion.

The robot arm units 21, 22, and 23 of the slave robot 20 described above may be implemented to be driven with multiple degrees of freedom. The robot arm units 21, 22, and 23 may include, for example, a surgical instrument inserted into a surgical site of a patient, a yaw driving part for rotating the surgical instrument in a yaw direction according to a surgical position, a pitch driving part for rotating the surgical instrument in a pitch direction perpendicular to a rotational driving of the yaw driving part, a transfer driving part for moving the surgical instrument in a length direction, a rotation driving part for rotating the surgical instrument, and a surgical instrument driving part for incising or cutting the surgical lesion by driving an end effector at an end of the surgical instrument. However, the configuration of the robot arm units 21, 22, and 23 is not limited thereto, and it should be understood that this example does not limit the scope of the present disclosure. Here, a detailed description of the actual control process, such as rotation and movement of the robot arm units 21, 22, and 23 in a corresponding direction by the surgical operator manipulating the manipulating member 10*a* will be omitted.

Here, two of the robot arm units 21, 22, and 23 may have the multi-joint type surgical device 30 attached thereto, and one of the robot arm units 21, 22, and 23 may have the laparoscope 50 attached thereto. In addition, the surgical operator may select the robot arm unit 21, 22, or 23 to be controlled via the master robot 10. As described above, by directly controlling a total of three or more surgical instruments through the master robot 10, the surgical operator may accurately and freely control various tools according to the intention of the surgical operator without a surgical assistant.

Meanwhile, one or more slave robots 20 may be provided to operate the patient, and the laparoscope 50 for allowing a surgical site to be displayed as a screen image through the display member 10*b* may be implemented as an independent slave robot 20. In addition, as described above, the embodiments of the present disclosure can be used universally for surgeries in which various surgical endoscopes other than laparoscopes (e.g., thoracoscopic, arthroscopic, rhinoscopic, and the like) are used.

Referring to FIG. 2, in an embodiment of the present disclosure, the master robot 10 may include an image input part 11, a screen display part 12, a user input part 13, a manipulation signal generation part 14, a control part 15, a memory 16, a storage part 17, and a communication part 18.

The image input part 11 may receive an image captured by a camera provided in the laparoscope 50 of the slave robot 20 through a wired or wireless communication network.

The screen display part 12 outputs a screen image corresponding to the image received through the image input part 11 as visual information. In addition, the screen display part 12 may further output information corresponding to biometric information of a subject to be treated, when the biometric information is input. In addition, the screen display part 12 may further output image data (e.g., an X-ray image, a CT image, an MRI image, or the like) associated with a patient for a surgical site. Here, the screen display part 12 may be implemented in the form of a display member (see 10*b* of FIG. 1), and an image processing process for allowing the received image to be output as a screen image through the screen display part 12 may be performed by the control part 15.

In the embodiment illustrated in FIG. 2, the image input part and the screen display part are illustrated as being included in the master robot 10, but the present disclosure is not limited thereto. That is, the display member may be provided as a separate member spaced apart from the master robot 10. Alternatively, the display member may be provided as one component of the master robot 10. In addition, in another embodiment, a plurality of display members may be provided, one of which may be disposed adjacent to the master robot 10, and others thereof may be disposed at some distance from the master robot 10.

Here, the screen display part 12 (that is, the display member 10b of FIG. 1) may be provided as a three-dimensional display device. In detail, the three-dimensional display device refers to an image display device in which depth information is added to a two-dimensional image by applying a stereoscopic technique, and this depth information is used to enable an observer to feel a three-dimensional living feeling and a sense of reality. The surgical robot system 1 according to an embodiment of the present disclosure may provide a more realistic virtual environment to a user by including a three-dimensional display device as the screen display part 12.

The user input part 13 is a member for allowing the surgical operator to manipulate the positions and functions of the robot arm units 21, 22, and 23 of the slave robot 20. The user input part 13 may be formed in the form of a handle-shaped manipulation member (see 10a of FIG. 1) as illustrated in FIG. 1, but the shape thereof is not limited thereto and may be implemented by being modified in various shapes to achieve the same purpose. In addition, for example, some of the user input part 13 may be formed in the shape of a handle, and the others may be formed in a different shape, such as a clutch button. In addition, a finger insertion tube or insertion ring may be further formed so as to allow the surgical operator's finger to be inserted therethrough and fixed to facilitate manipulation of the surgical tool.

When the surgical operator manipulates the user input part 13 to move the positions of robot arm units 21, 22, and 23 or manipulate surgical operations thereof, the manipulation signal generation part 14 may generate a corresponding manipulation signal, and transmit the manipulation signal to the slave robot 20 through the communication part 18. The manipulation signal may be transmitted and received via a wired or wireless communication network.

The control part 15 is a kind of central processing device, and controls the operation of each component so that the above-described functions can be performed. In an example, the control part 15 may perform a function of converting an image input through the image input part 11 into a screen image to be displayed through the screen display part 12.

The memory 16 may perform a function of temporarily or permanently storing data processed by the control part 15. Here, the memory 16 may include a magnetic storage medium or a flash storage medium, but the scope of the present disclosure is not limited thereto.

The storage part 17 may store data received from the slave robot 20. In addition, the storage part 17 may store various pieces of input data (e.g., patient data, device data, surgery data, and the like).

The communication part 18 interworks with a communication network 60 to provide a communication interface necessary for transmitting and receiving image data transmitted from the slave robot 20 and control data transmitted from the master robot 10.

The slave robot 20 includes a plurality of robot arm unit control parts 21a, 22a, and 23a. In addition, the robot arm unit control part 21a includes a robot arm control part 26, an instrument control part 27, and a communication part 29. In addition, the robot arm unit control part 21a may further include a rail control part 28.

The robot arm control part 26 may receive a manipulation signal generated by the manipulation signal generation part 14 of the master robot 10, and may serve to control the robot arm units 21, 22, and 23 so as to operate according to the manipulation signal.

The instrument control part 27 may receive a manipulation signal generated by the manipulation signal generation part 14 of the master robot 10, and may serve to control the multi-joint type surgical device 30 so as to operate according to the manipulation signal.

The communication part 29 interworks with the communication network 60 to provide a communication interface necessary for transmitting and receiving image data transmitted from the slave robot 20 and control data transmitted from the master robot 10.

Meanwhile, the communication network 60 serves to connect the master robot 10 and the slave robot 20. That is, the communication network 60 refers to a communication network for providing an access path so that data can be transmitted and received between the master robot 10 and the slave robot 20 after the master robot 10 and the slave robot 20 are connected. The communication network 60 may be, for example, a wired network such as local area networks (LANs), wired area networks (WANs), metropolitan area networks (MANs), and integrated service digital networks (ISDNs), or a wireless network such as wireless LANs, code division multiple access (CDMA), Bluetooth, and satellite communication, but the scope of the present disclosure is not limited thereto.

(Multi-Joint Type Surgical Device)

Figure 4:
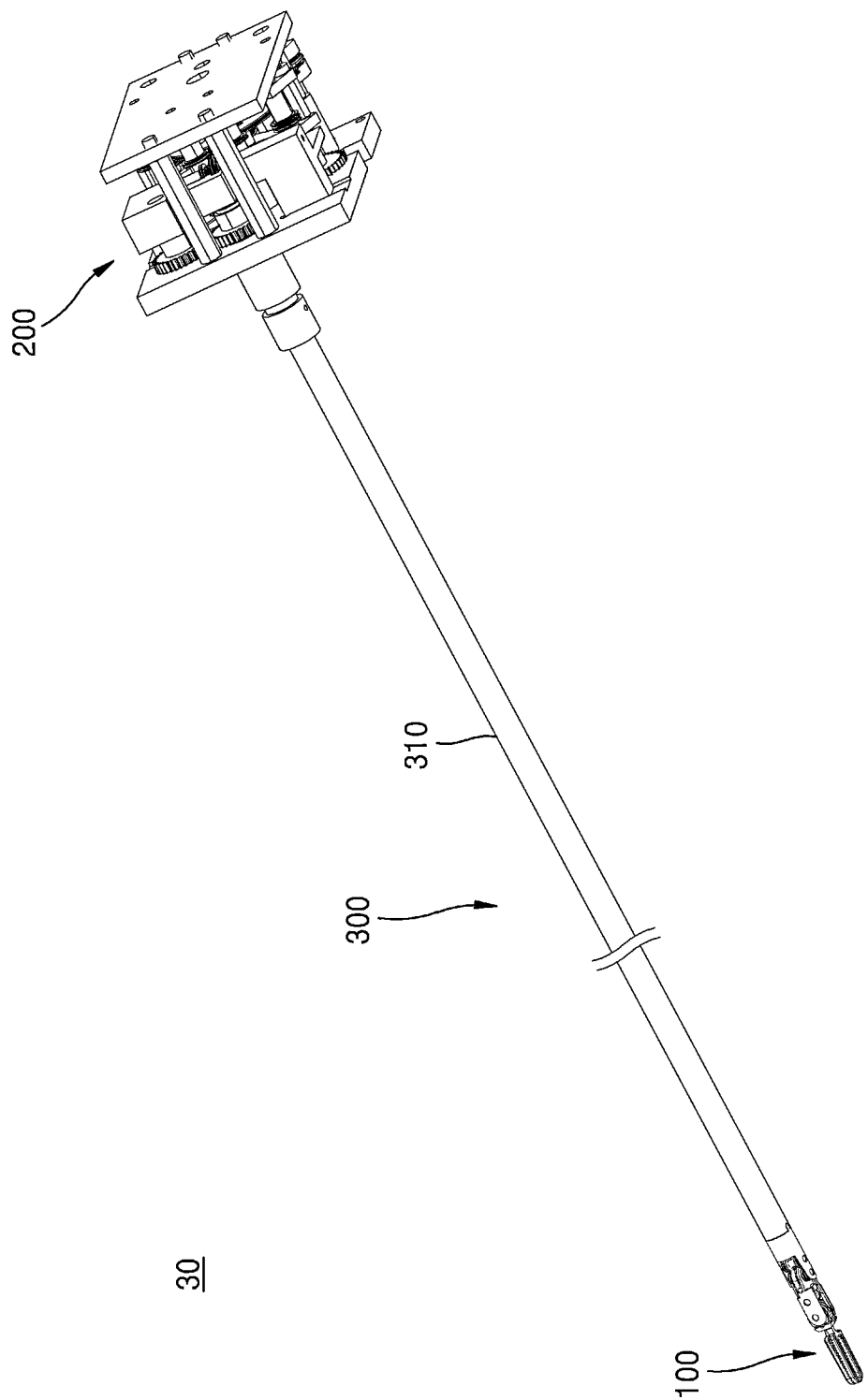
FIG. 4 is a perspective view illustrating a multi-joint type surgical device according to an embodiment of the present disclosure.
Figure 5:
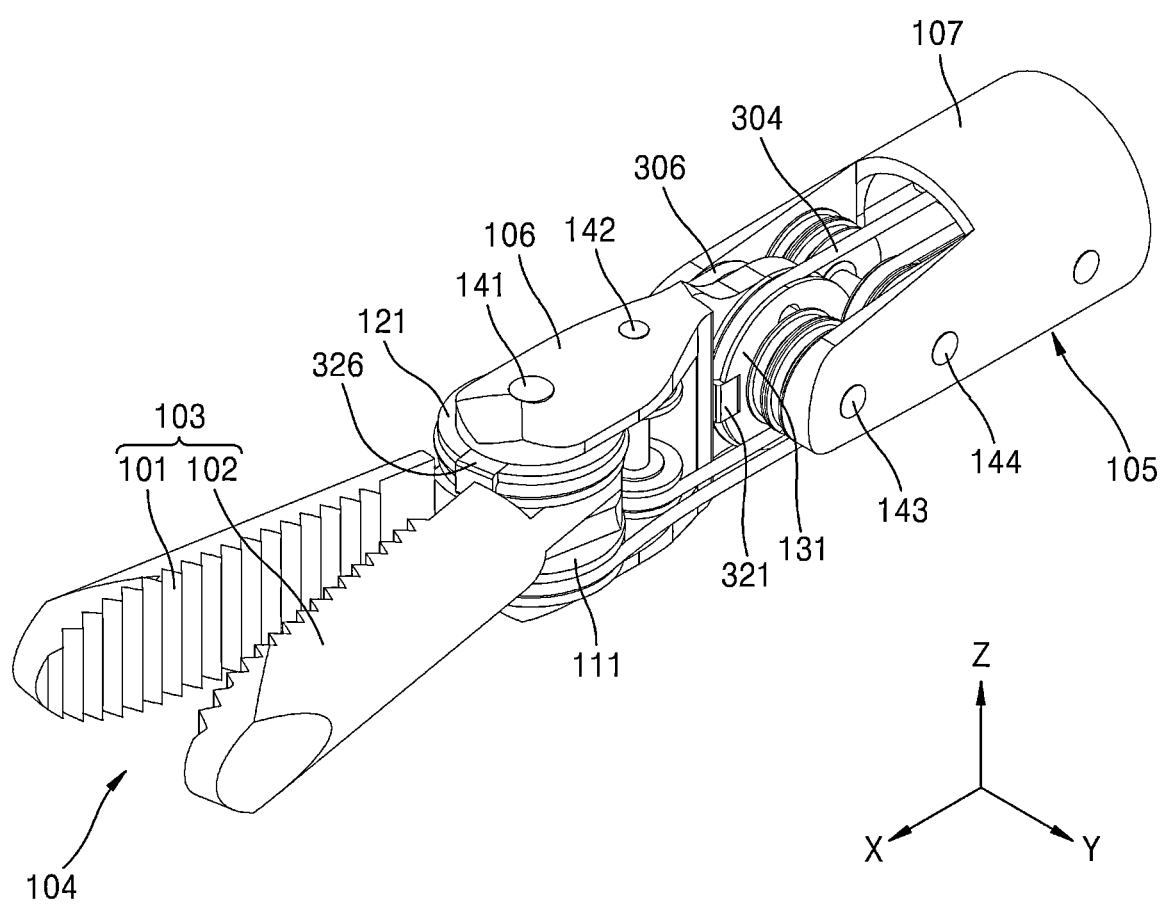
FIGS. 5 and 6 are perspective views of an end tool of the multi-joint type surgical device of FIG. 4.
Figure 6:
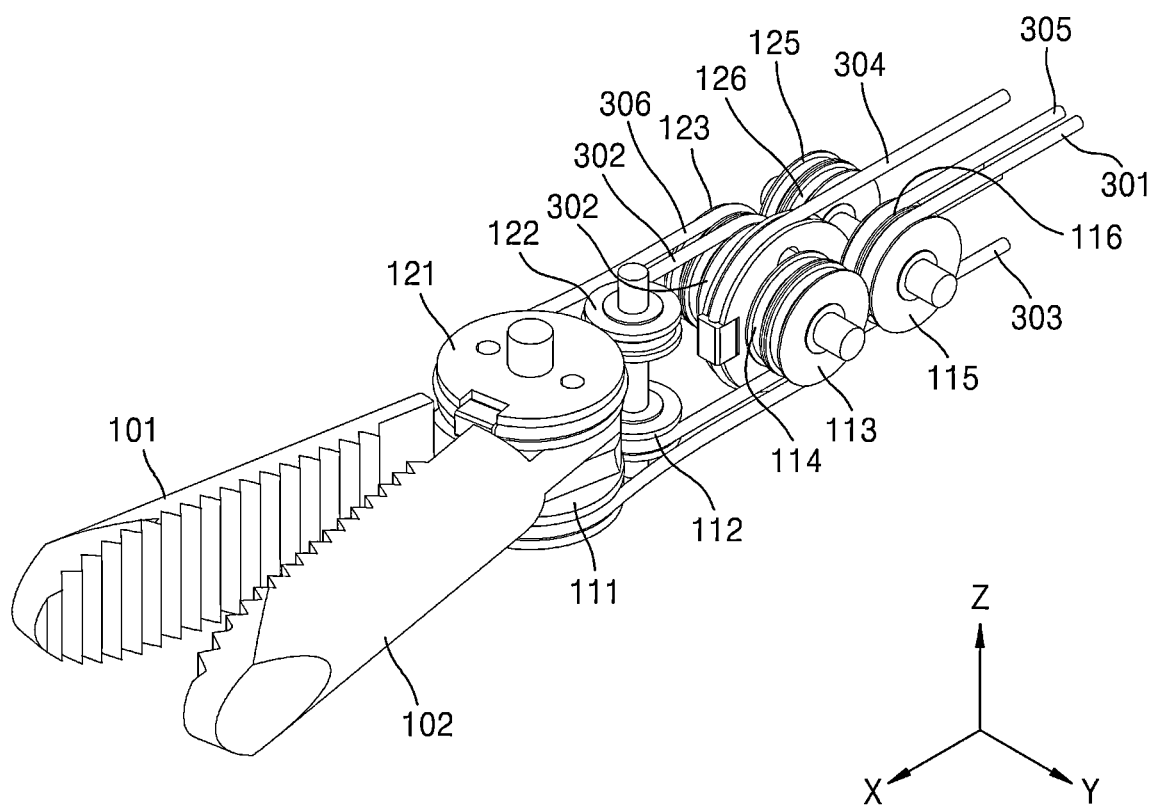
Figure 7:
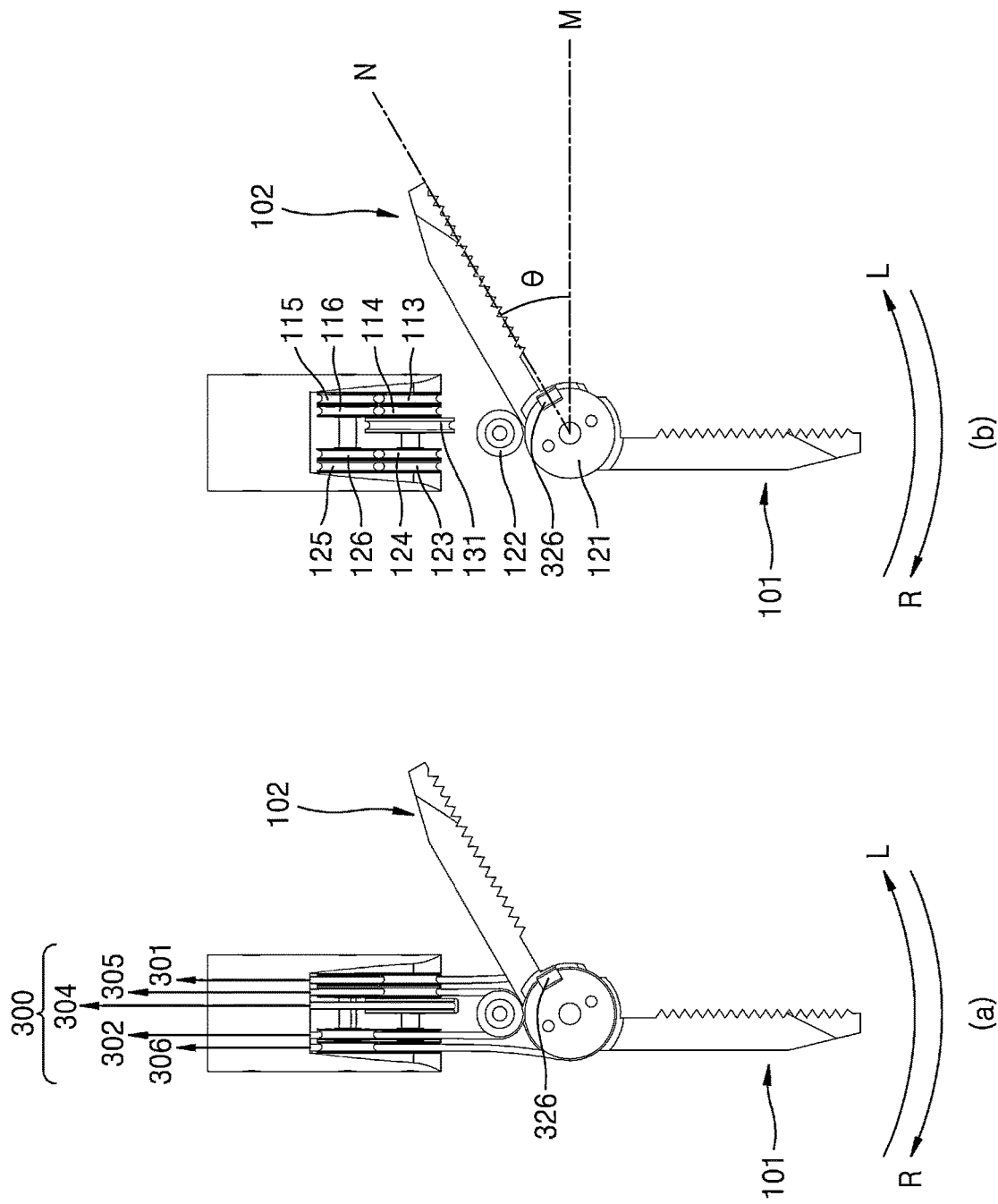
FIG. 7 is a plan view of the end tool of the multi-joint type surgical device of FIG. 4.
Figure 8:
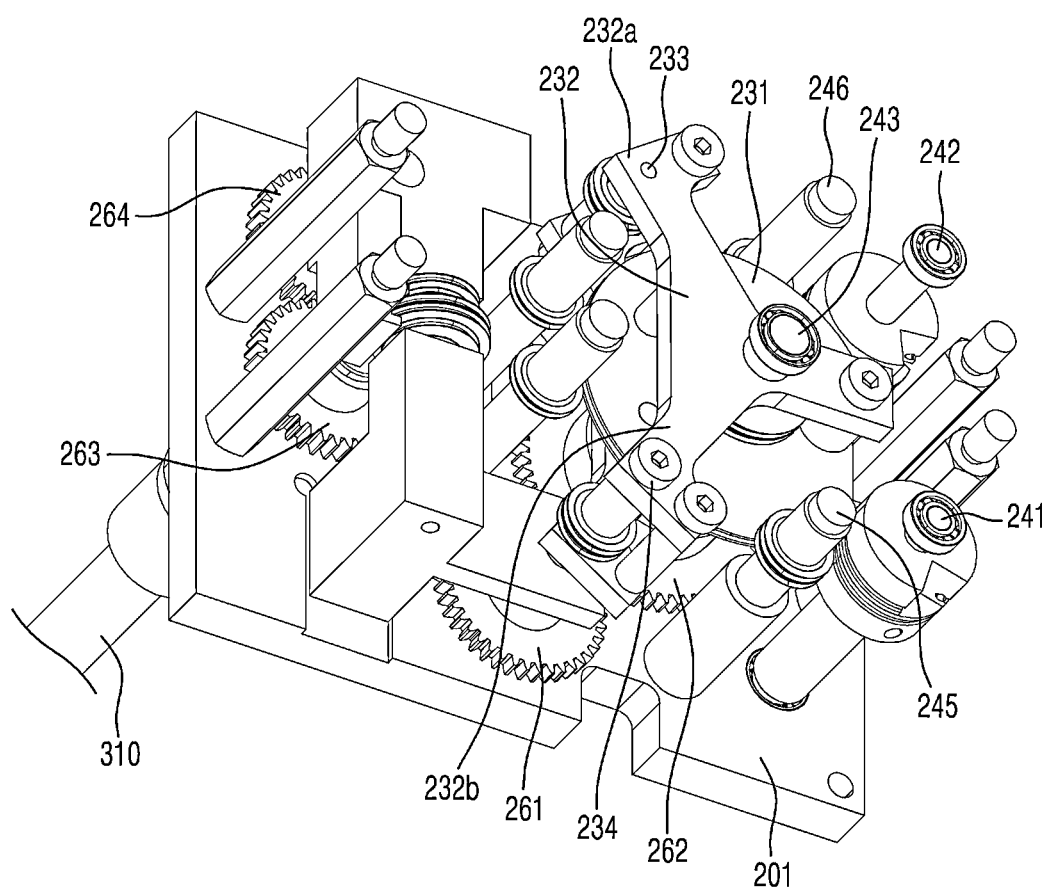
FIGS. 8 and 9 are perspective views of a driving part of the multi-joint type surgical device of FIG. 4.
Figure 9:
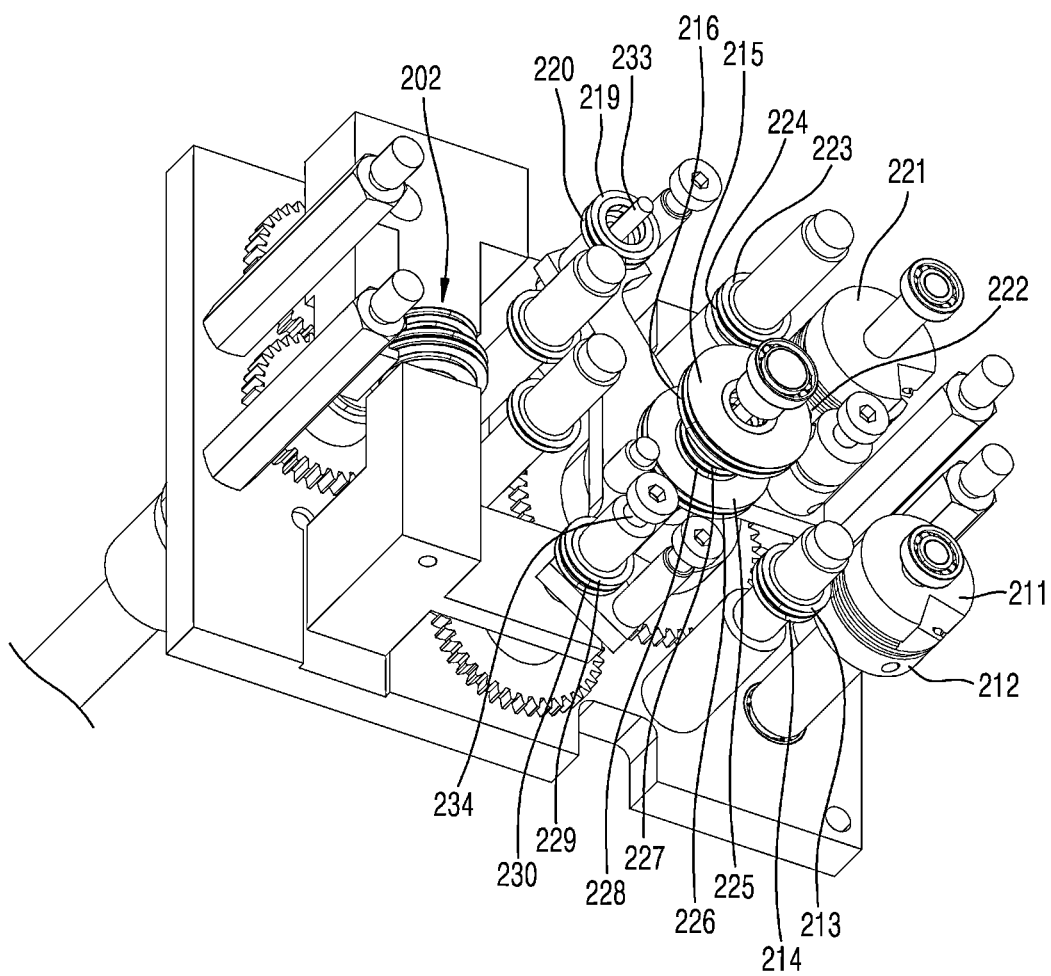
Figure 10:
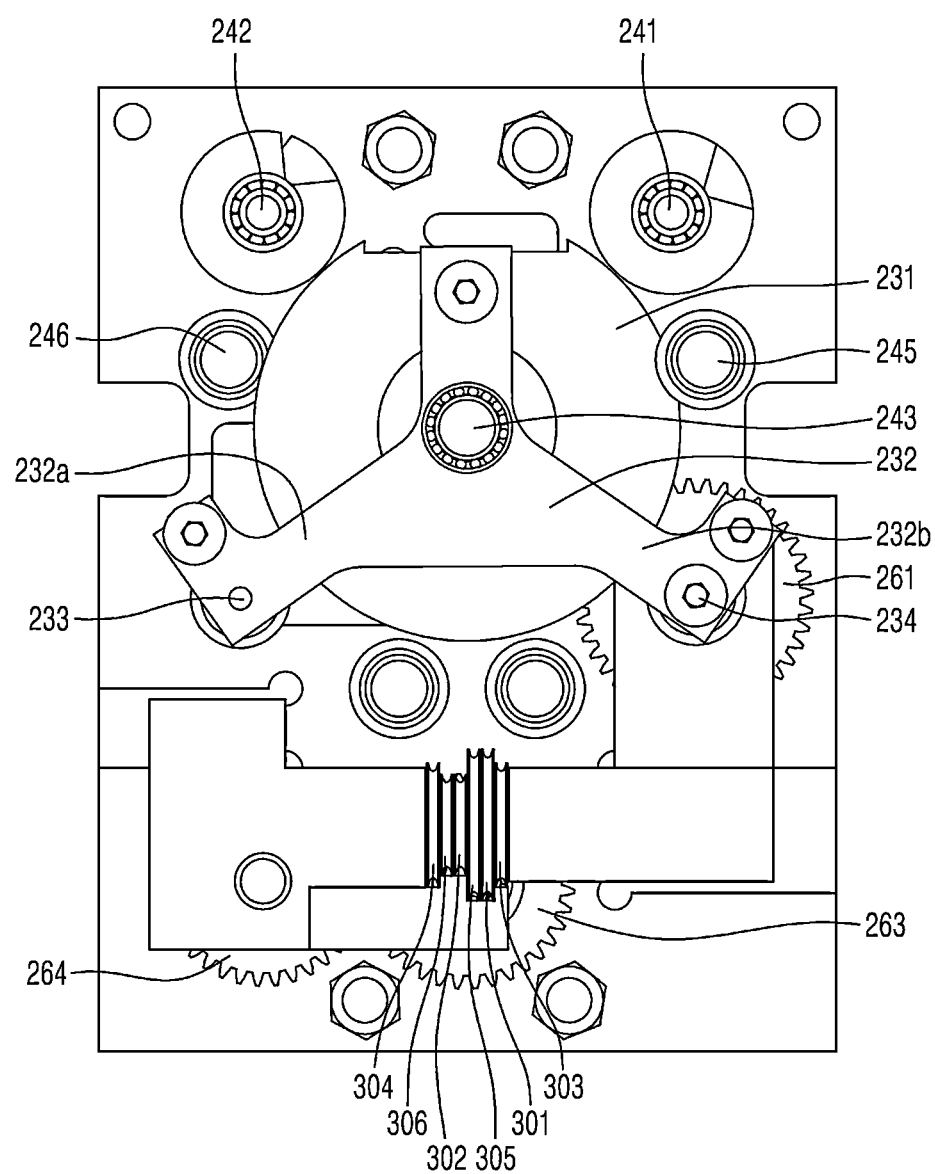
FIG. 10 is a plan view of the driving part of the multi-joint type surgical device of FIG. 4.
Figure 11:
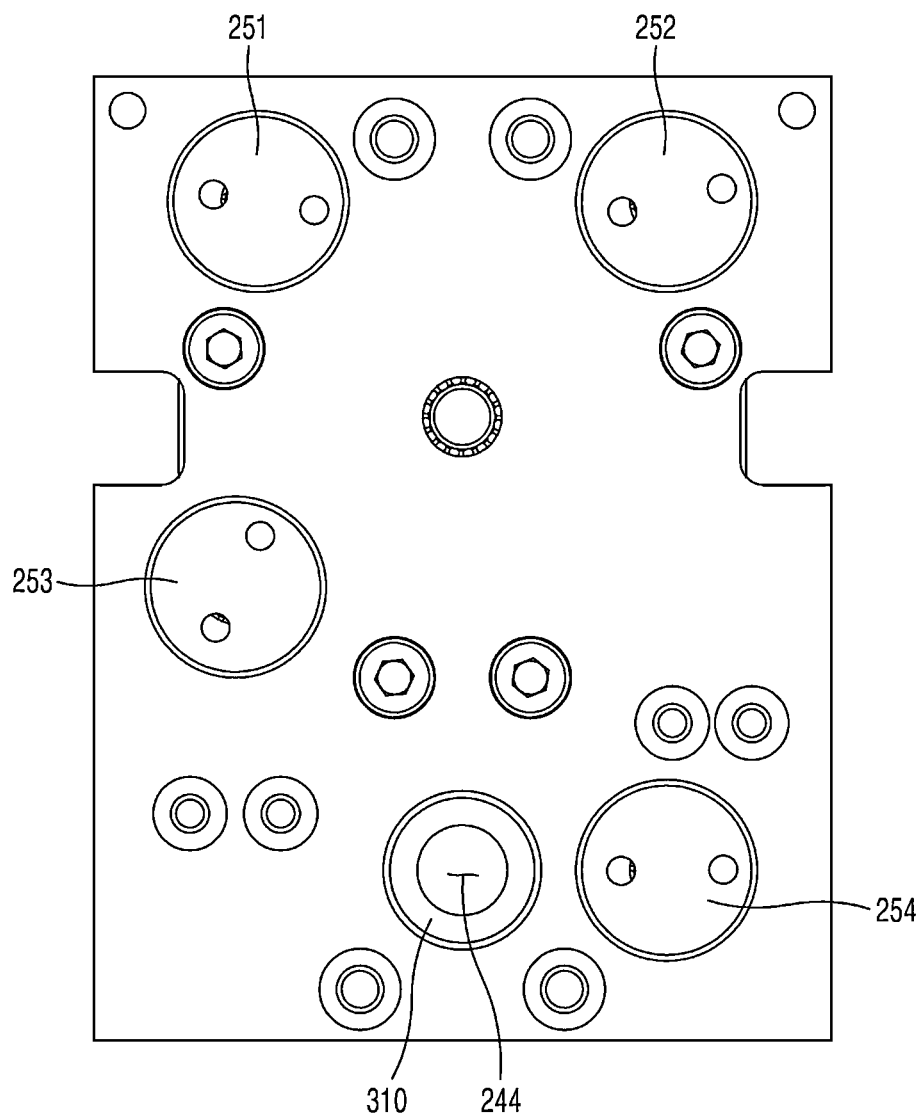
FIG. 11 is a rear view of the driving part of the multi-joint type surgical device of FIG. 4.
Figure 12:
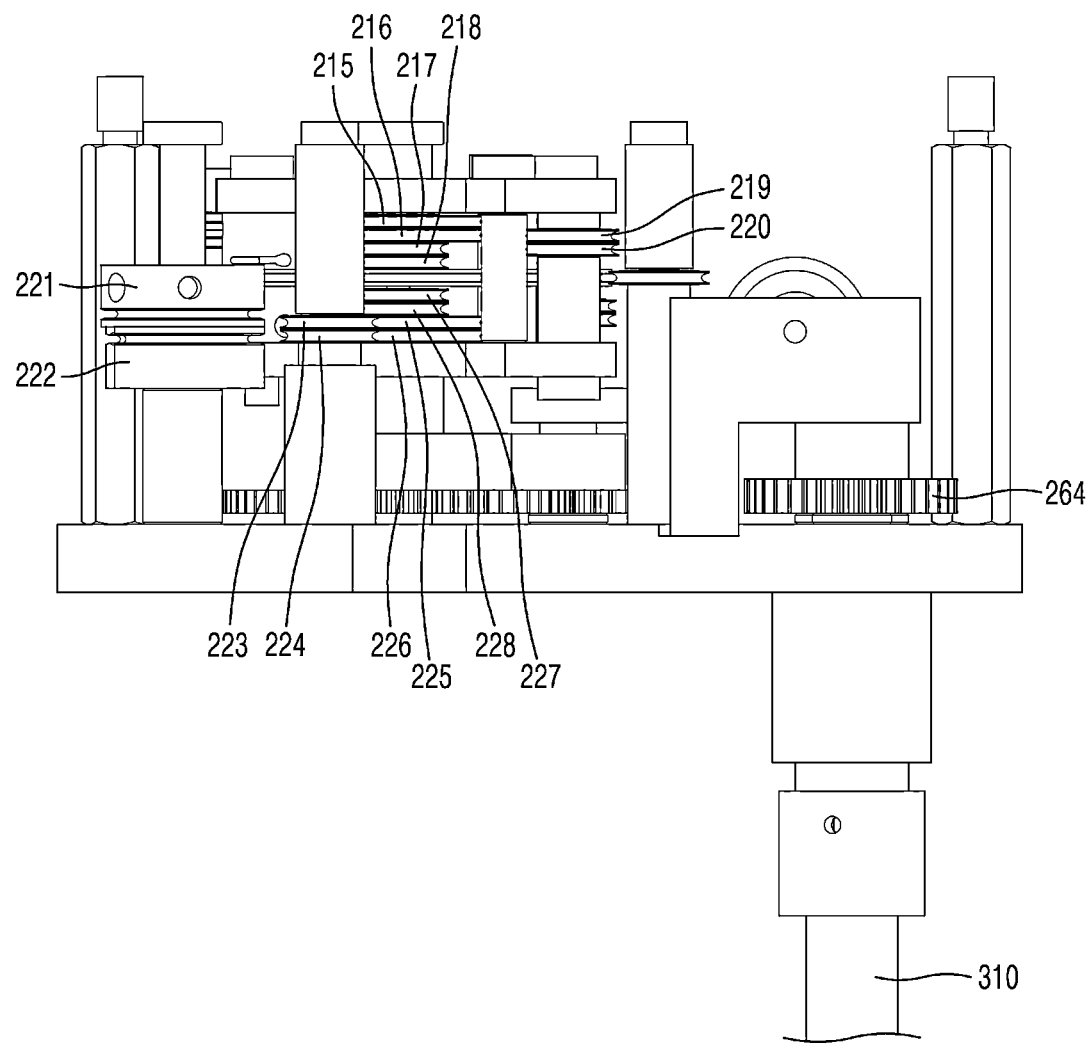
FIG. 12 is a side view of the driving part of the multi-joint type surgical device of FIG. 4.
Figure 13:
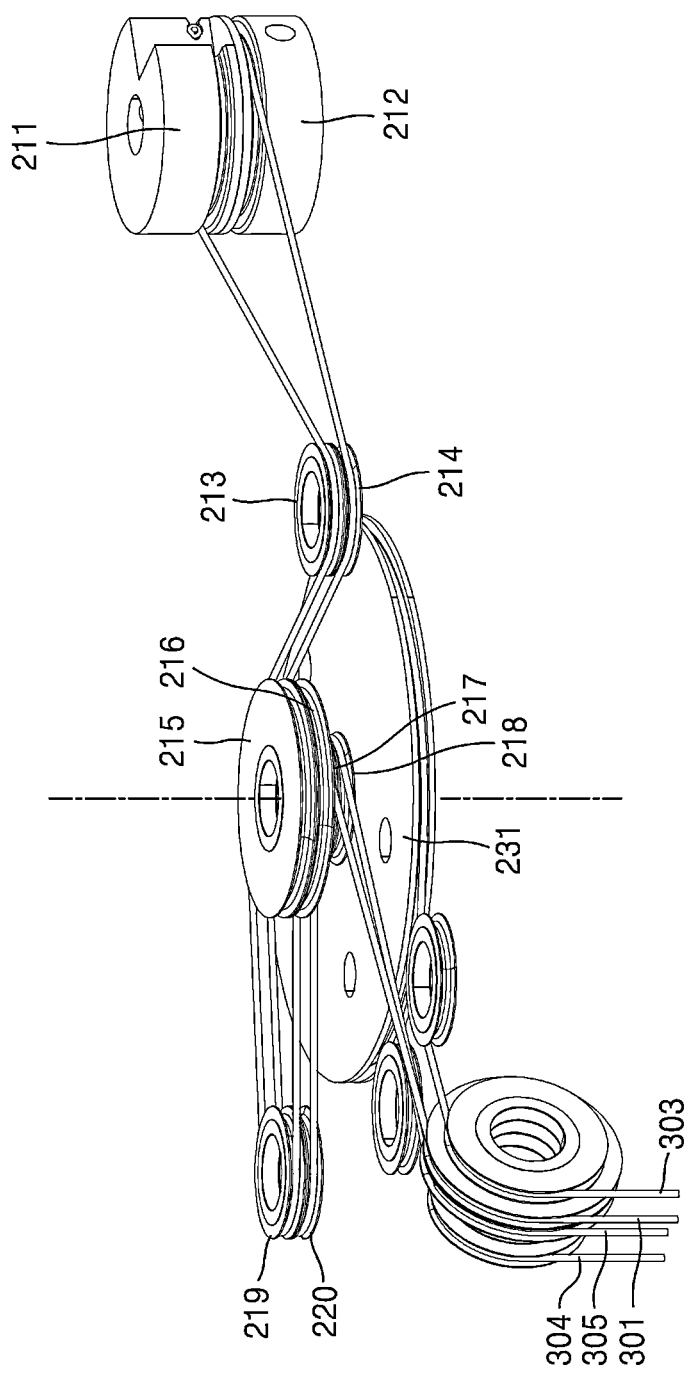
FIG. 13 is a view illustrating the configuration of pulleys and wires of the multi-joint type surgical device illustrated in FIG. 4, in detail for the configuration related to a first jaw.
Figure 14:
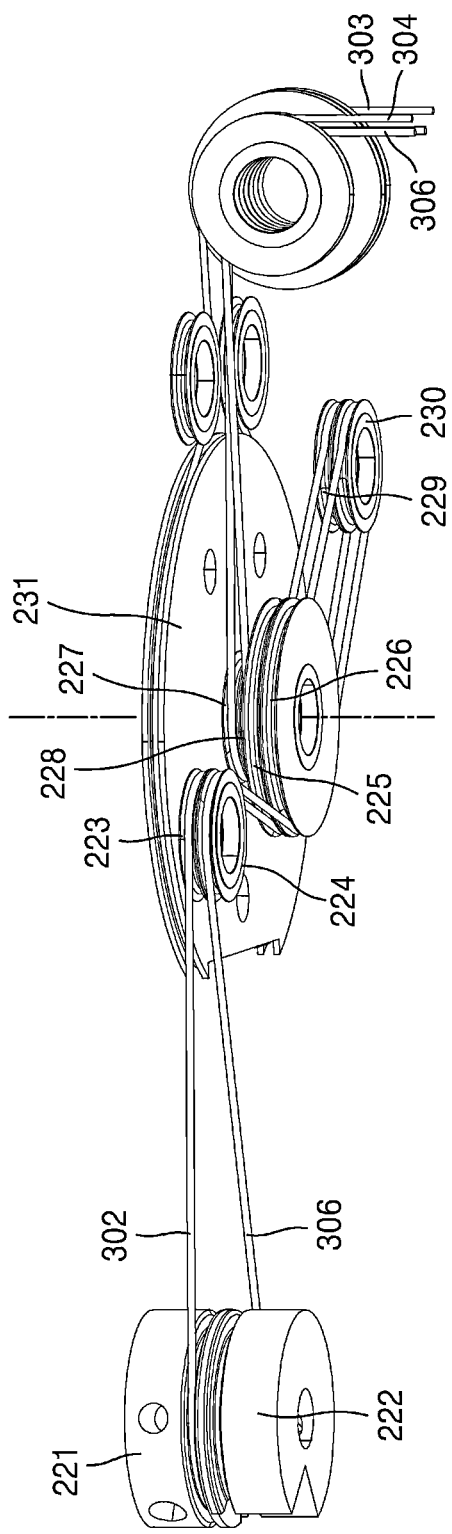
FIG. 14 is a view illustrating the configuration of pulleys and wires of the multi-joint type surgical device illustrated in FIG. 4, in detail for the configuration related to a second jaw.

FIG. 4 is a perspective view illustrating a multi-joint type surgical device according to an embodiment of the present disclosure, FIGS. 5 and 6 are perspective views of an end tool of the multi-joint type surgical device of FIG. 4, and FIG. 7 is a plan view of the end tool of the multi-joint type surgical device of FIG. 4. FIGS. 8 and 9 are perspective views of a driving part of the multi-joint type surgical device of FIG. 4, FIG. 10 is a plan view of the driving part of the multi-joint type surgical device of FIG. 4, FIG. 11 is a rear view of the driving part of the multi-joint type surgical device of FIG. 4, and FIG. 12 is a side view of the driving part of the multi-joint type surgical device of FIG. 4.

Referring first to FIG. 4, a multi-joint type surgical device 30 according to a first embodiment of the present disclosure may include an end tool 100, a driving part 200, and a power transmission part 300, and the power transmission part 300 may include a connection part 310.

Here, the connection part 310 is formed in the shape of a hollow shaft, in which one or more wires (to be described later) may be accommodated, and may have one end portion to which the driving part 200 is coupled and the other end portion to which the end tool 100 is coupled and serve to connect the driving part 200 and the end tool 100.

The driving part 200 is formed at one end portion of the connection part 310 and provides an interface capable of being coupled to the robot arm unit (see 21 or the like in FIG. 1). Accordingly, when a user operates the master robot (see 10 in FIG. 1), a motor (not shown) of the robot arm unit (see 21 or the like in FIG. 1) is operated so that the end tool 100 of the multi-joint type surgical device 30 can perform a motion corresponding thereto, and a driving force of the motor (not shown) is transmitted to the end tool 100 through the driving part 200. Viewed from another perspective, it may be described that the driving part 200 itself becomes an interface between the multi-joint type surgical device 30 and the slave robot 20.

The end tool 100 is formed on the other end portion of the connection part 310, and performs necessary motions for surgery by being inserted into a surgical site. In an example of the above-described end tool 100, as shown in FIG. 5, a pair of jaws 101 and 102 for performing a grip motion may be used. However, the concept of the present disclosure is not limited thereto, and various devices for performing surgery may be used as the end tool 100. For example, a configuration such as a cantilever cautery may also be used as the end tool. The above-described end tool 100 is connected to the driving part 200 by the power transmission part 300 and receives a driving force through the power transmission part 300 to perform a motion necessary for surgery, such as a gripping motion, a cutting motion, a suturing motion, or the like.

Here, the end tool 100 of the multi-joint type surgical device 30 according to the first embodiment of the present disclosure is formed to be rotatable in at least two directions, for example, the end tool 100 may be formed to perform a pitch motion around a rotation shaft 143 of FIG. 5 and simultaneously perform a yaw motion and an actuation motion around a rotation shaft 141 of FIG. 5.

Here, each of the pitch, yaw, and actuation motions used in the present disclosure are defined as follows.

First, the pitch motion means a motion of the end tool 100 rotating in a vertical direction with respect to an extension direction of the connection part 310 (an X-axis direction of FIG. 4), that is, a motion rotating around the Y-axis of FIG. 4. In other words, the pitch motion means a motion of the end tool 100, which is formed to extend from the connection part 310 in the extension direction of the connection part 310 (the X-axis direction of FIG. 4), rotating vertically around the Y-axis with respect to the connection part 310.

Next, the yaw motion means a motion of the end tool 100 rotating in left and right directions, that is, a motion rotating around the Z-axis of FIG. 4, with respect to the extension direction of the connection part 310 (the X-axis direction of FIG. 4). In other words, the yaw motion means a motion of the end tool 100, which is formed to extend from the connection part 310 in the extension direction of the connection part 310 (the X-axis direction of FIG. 4), rotating horizontally around the Z-axis with respect to the connection part 310. That is, the yaw motion means a motion of two jaws 101 and 102, which are formed on the end tool 100, rotating around the Z-axis in the same direction.

Meanwhile, the actuation motion means a motion of the end tool 100 rotating around the same shaft of rotation as that of the yaw motion, while the two jaws 101 and 102 rotate in the opposite directions so as to be closed or opened. That is, the actuation motion means rotating motions of the two jaws 101 and 102, which are formed on the end tool 100, in the opposite directions around the Z-axis.

Defining this from another perspective, the yaw rotation may be defined as a motion in which an end tool jaw pulley to be described later is rotated around the rotation shaft 141, which is an end tool jaw pulley rotation shaft, and the pitch rotation may be defined as a motion in which the end tool jaw pulley is revolved around the rotation shaft 143, which is an end tool pitch rotation shaft.

The power transmission part 300 may connect the driving part 200 and the end tool 100, transmit the driving force from the driving part 200 to the end tool 100, and include a plurality of wires, pulleys, links, sections, gears, or the like.

Hereinafter, the end tool 100, the driving part 200, the power transmission part 300, and the like of the multi-joint type surgical device 30 of FIG. 4 will be described in more detail.

(Power Transmission Part)

Hereinafter, the power transmission part 300 of the multi-joint type surgical device 30 of FIG. 4 will be described in more detail.

Referring to FIGS. 4 to 12, the power transmission part 300 of the multi-joint type surgical device 30 according to an embodiment of the present disclosure may include a wire 301, a wire 302, a wire 303, a wire 304, a wire 305, and a wire 306.

Here, the wires 301 and 305 may be paired to serve as first jaw wires. The wires 302 and 306 may be paired to serve as second jaw wires. Here, the components encompassing the wires 301 and 305, which are first jaw wires, and the wires 302 and 306, which are second jaw wires, may be referred to as jaw wires. In addition, the wires 303 and 304 may be paired to serve as pitch wires.

Here, in the drawings, a pair of wires are illustrated as being associated with a rotational motion of a first jaw 101, and a pair of wires are illustrated as being associated with a rotational motion of a second jaw 102, but the concept of the present disclosure is not limited thereto. For example, a pair of wires may be associated with a yaw motion, and a pair of wires may be associated with an actuation motion.

In addition, the power transmission part 300 of the multi-joint type surgical device 30 according to an embodiment of the present disclosure may include a coupling member 321, a coupling member 326, and the like, which are coupled to respective end portions of the wires in order to couple the wires and the pulleys. Here, each of the coupling members may have various shapes as necessary, such as a ball shape, a tube shape, and the like.

Here, the coupling member 321, which is a pitch wire coupling member, is coupled to the end portions of the wires 303 and 304, which are pitch wires, at the end tool 100 side to serve as a pitch wire-end tool coupling member. Meanwhile, although not illustrated in the drawings, a pitch wire-driving part coupling member (not shown) may be coupled to the end portions of the wires 303 and 304, which are pitch wires, at the driving part 200 side.

Meanwhile, the coupling member 326, which is a second jaw wire coupling member, is coupled to the end portions of the wires 302 and 306, which are second jaw wires, at the end tool 100 side to serve as a second jaw wire-end tool coupling member. Meanwhile, although not illustrated in the drawings, a second jaw wire-driving part coupling member (not shown) may be coupled to the end portions of the wires 302 and 306, which are second jaw wires, at the driving part 200 side.

Meanwhile, although not illustrated in the drawings, a coupling member (not shown) having the same shape as the coupling member 326 may be coupled to the end portions of the wires 301 and 305, which are first jaw wires, at the end tool 100 side to serve as a first jaw wire-end tool coupling member. Meanwhile, although not illustrated in the drawings, a first jaw wire-driving part coupling member (not shown) may be coupled to the end portions of the wires 301 and 305, which are first jaw wires, at the driving part 200 side.

Here, each of the coupling members is classified as being included in the power transmission part 300, but the coupling members may be classified such that the coupling member at the end tool 100 side may be included in the end tool 100, and the coupling member at the driving part 200 side may be included in the driving part 200.

The coupling relationship between the wires, the coupling members, and the respectively pulleys will be described in detail as follows.

First, the wires 302 and 306, which are second jaw wires, may be a single wire. The coupling member 326, which is a first jaw wire-end tool coupling member, is inserted at an intermediate point of the second jaw wire, which is a single wire, and the coupling member 326 is crimped and fixed, and then, both strands of the second jaw wire centered on the coupling member 326 may be referred to as the wire 302 and the wire 306, respectively.

Alternatively, the wires 302 and 306, which are second jaw wires, may also be formed as separate wires, and connected by the coupling member 326.

In addition, by coupling the coupling member 326 to a pulley 121, the wires 302 and 306 may be fixedly coupled to the pulley 121. This allows the pulley 121 to rotate as the wires 302 and 306 are pulled and released.

Meanwhile, the second jaw wire-driving part coupling member (not shown) may be coupled to the end portions of the wires 302 and 306, which are opposite to the end portions to which the coupling member 326 is coupled. That is, the second jaw wire-driving part coupling member (not shown) may be fixed to each of the wires 302 and 306 by inserting the opposite end portions of the wires 302 and 306 into the second jaw wire-driving part coupling member (not shown) and crimping the coupling member (not shown).

In addition, by coupling the second jaw wire-driving part coupling member (not shown) coupled to the wires 302 and 306 to each of the pulley 221 and the pulley 222, the wire 302 and the wire 306 may be fixedly coupled to the pulley 221 and the pulley 222, respectively. As a result, when the pulley 221 and the pulley 222 are rotated by a motor or a human force, the pulley 121 of the end tool 100 may be rotated as the wire 302 and the wire 306 are pulled and released.

Here, a driving part second jaw pulley may include two pulleys of the pulley 221 and the pulley 222, and thus the second jaw wire-driving part coupling member may also include two coupling members. Alternatively, the driving part second jaw pulley includes one pulley, the second jaw wire-driving part coupling member also includes one coupling member, and the wires 302 and 306 may be coupled to one coupling member to be coupled to one driving part second jaw pulley.

In the same manner, the wire 301 and the wire 305, which are first jaw wires, are coupled to the first jaw wire-end tool coupling member (not shown) and the first jaw wire-driving part coupling member (not shown), respectively. In addition, the first jaw wire-end tool coupling member (not shown) is coupled to a pulley 111, and the first jaw wire-driving part coupling member (not shown) is coupled to a pulley 211 and a pulley 212. As a result, when the pulleys 211 and 212 are rotated by a motor or a human force, the pulley 111 of the end tool 100 may be rotated as the wire 301 and the wire 305 are pulled and released.

In the same manner, each of one end portions of the wires 303 and 304, which are pitch wires, is coupled to the coupling member 321, which is a pitch wire-end tool coupling member, and each of the other end portions of the wires 303 and 304 are coupled to the pitch wire-driving part coupling member (not shown). In addition, the coupling member 321 is coupled to a pulley 131, and the pitch wire-driving part coupling member (not shown) is coupled to a pulley 231. As a result, when the pulley 231 is rotated by a motor or a human force, the pulley 131 of the end tool 100 may be rotated as the wire 303 and the wire 304 are pulled and released.

As a result, the wire 301 and the wire 305, which are both strands of the first jaw wire, are coupled to a coupling member 323, which is a first jaw wire-end tool coupling member, and the first jaw wire-driving part coupling member (not shown) so as to form as a whole a closed loop. Similarly, the second jaw wire and the pitch wire may each be formed to form a closed loop.

(End Tool)

Hereinafter, the end tool 100 of the multi-joint type surgical device 30 of FIG. 4 will be described in more detail.

FIGS. 5 and 6 are perspective views illustrating the end tool of the multi-joint type surgical device of FIG. 4, and FIG. 7 is a plan view illustrating the end tool of the multi-joint type surgical device of FIG. 4. Here, FIG. 5 illustrates a state in which an end tool hub 106 and a pitch hub 107 are coupled, and FIG. 6 illustrates a state in which the end tool hub 106 and the pitch hub 107 are removed.

Referring to FIGS. 5 to 7, the end tool 100 of the first embodiment of the present disclosure includes a pair of jaws for performing a grip motion, that is, the first jaw 101 and the second jaw 102. Here, each of the first jaw 101 and the second jaw 102, or a component encompassing the first jaw 101 and the second jaw 102 may be referred to as a jaw 103.

Further, the end tool 100 may include the pulley 111, a pulley 112, a pulley 113, a pulley 114, a pulley 115, and a pulley 116 that are related to a rotational motion of the first jaw 101. In addition, the end tool 100 may include the pulley 121, a pulley 122, a pulley 123, a pulley 124, a pulley 125, and a pulley 126 that are related to a rotational motion of the second jaw 102.

Here, in the drawings, one group of pulleys are illustrated as being associated with a rotational motion of the first jaw 101, and one group of pulleys are illustrated as being associated with a rotational motion of the second jaw 102, but the concept of the present disclosure is not limited thereto. For example, one group of pulleys in the end tool may be associated with a yaw motion, and one group of pulleys in the end tool may be associated with an actuation motion. Here, the pulleys included in the end tool 100, including the pulleys described above, may be collectively referred to as end tool pulleys.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 100 of the first embodiment of the present disclosure may include the end tool hub 106 and the pitch hub 107.

The rotation shaft 141 and a rotation shaft 142, which will be described later, may be inserted through the end tool hub 106, and the end tool hub 106 may internally accommodate at least some of the first jaw 101 and the second jaw 102, which are axially coupled to the rotation shaft 141. In addition, the end tool hub 106 may internally accommodate at least some of the pulley 112 and the pulley 122 that are axially coupled to the rotation shaft 142.

In addition, the pulley 131 serving as an end tool pitch pulley may be formed at one end portion of the end tool hub 106. As shown in FIG. 5, the pulley 131 may be formed as a separate member from the end tool hub 106 and coupled to the end tool hub 106. Alternatively, although not illustrated in the drawings, the pulley 131 may be integrally formed with the end tool hub 106 as one body. That is, one end portion of the end tool hub 106 is formed in a disk shape or a semi-circular shape such as a pulley, and a groove around which a wire can be wound may be formed on an outer circumferential surface thereof. The wires 303 and 304 described above are coupled to the pulley 131 serving as an end tool pitch pulley, and a pitch motion is performed as the pulley 131 is rotated around the rotation shaft 143.

The rotation shaft 143 and a rotation shaft 144, which will be described later, may be inserted through the pitch hub 107, and the pitch hub 107 may be axially coupled to the end tool hub 106 and the pulley 131 by the rotation shaft 143. Thus, the end tool hub 106 and the pulley 131 (coupled thereto) may be formed to be rotatable around the rotation shaft 143 with respect to the pitch hub 107.

Further, the pitch hub 107 may internally accommodate at least some of the pulley 113, the pulley 114, the pulley 123, and the pulley 124 that are axially coupled to the rotation shaft 143. In addition, the pitch hub 107 may internally accommodate at least some of the pulley 115, the pulley 116, the pulley 125, and the pulley 126 that are axially coupled to the rotation shaft 144.

Further, the end tool 100 of the first embodiment of the present disclosure may include the rotation shaft 141, the rotation shaft 142, the rotation shaft 143, and the rotation shaft 144. As described above, the rotation shaft 141 and the rotation shaft 142 may be inserted through the end tool hub 106, and the rotation shaft 143 and the rotation shaft 144 may be inserted through the pitch hub 107.

The rotation shaft 141, the rotation shaft 142, the rotation shaft 143, and the rotation shaft 144 may be arranged sequentially from a distal end 104 of the end tool 100 toward a proximal end 105 thereof. Accordingly, starting from the distal end 104, the rotation shaft 141 may be referred to as a first pin, the rotation shaft 142 may be referred to as a second pin, the rotation shaft 143 may be referred to as a third pin, and the rotation shaft 144 may be referred to as a fourth pin.

Here, the rotation shaft 141 may function as an end tool jaw pulley rotation shaft, the rotation shaft 142 may function as an end tool jaw auxiliary pulley rotation shaft, the rotation shaft 143 may function as an end tool pitch rotation shaft, and the rotation shaft 144 may function as an end tool pitch auxiliary rotation shaft of the end tool 100.

Each of the rotation shafts 141, 142, 143, and 144 may be fitted into one or more pulleys, which will be described in detail below.

The pulley 111 functions as an end tool first jaw pulley, and the pulley 121 functions as an end tool second jaw pulley, and these two components may be collectively referred to as end tool jaw pulleys.

The pulley 111 and the pulley 121, which are end tool jaw pulleys, are formed to face each other, and are formed to be rotatable independently of each other around the rotation shaft 141, which is an end tool jaw pulley rotation shaft. Here, in the drawings, it is illustrated that the pulley 111 and the pulley 121 are formed to rotate around one rotation shaft 141, but it is of course possible that each end tool jaw pulley may be formed to be rotatable around a separate shaft. Here, the first jaw 101 may be fixedly coupled to the pulley 111 and rotated together with the pulley 111, and the second jaw 102 may be fixedly coupled to the pulley 121 and rotated together with the pulley 121. Yaw and actuation motions of the end tool 100 are performed according to the rotation of the pulley 111 and the pulley 121. That is, when the pulley 111 and the pulley 121 are rotated in the same direction around the rotation shaft 141, the yaw motion is performed, and when the pulley 111 and the pulley 121 are rotated in opposite directions around the rotation shaft 141, the actuation motion is performed.

Here, the first jaw 101 and the pulley 111 may be formed as separate members and coupled to each other, or the first jaw 101 and the pulley 111 may be integrally formed as one body. Similarly, the second jaw 102 and the pulley 121 may be formed as separate members and coupled to each other, or the second jaw 102 and the pulley 121 may be integrally formed as one body.

The pulley 112 functions as an end tool first jaw auxiliary pulley, and the pulley 122 functions as an end tool second jaw auxiliary pulley, and these two components may be collectively referred to as end tool jaw auxiliary pulleys.

In detail, the pulley 112 and the pulley 122, which are end tool jaw auxiliary pulleys, may be additionally provided on one side of the pulley 111 and one side of the pulley 121, respectively. In other words, the pulley 112, which is an auxiliary pulley, may be disposed between the pulley 111 and the pulley 113/pulley 114. In addition, the pulley 122, which is an auxiliary pulley, may be disposed between the pulley 121 and the pulley 123/pulley 124. The pulley 112 and the pulley 122 may be formed to be rotatable independently of each other around the rotation shaft 142. Here, in the drawings, it is illustrated that the pulley 112 and the pulley 122 are formed to rotate around one rotation shaft 142, but it is of course possible that each of the pulley 112 and the pulley 122 may be formed to be rotatable around a separate shaft. Such auxiliary pulleys will be described in more detail later.

The pulley 113 and the pulley 114 function as end tool first jaw pitch main pulleys, and the pulley 123 and the pulley 124 function as end tool second jaw pitch main pulleys, and these two components may be collectively referred to as end tool jaw pitch main pulleys.

The pulley 115 and the pulley 116 function as end tool first jaw pitch sub-pulleys, and the pulley 125 and the pulley 126 function as end tool second jaw pitch sub-pulleys, and these two components may be collectively referred to as end tool jaw pitch sub-pulleys.

Hereinafter, components related to the rotation of the pulley 111 will be described.

The pulley 113 and the pulley 114 function as end tool first jaw pitch main pulleys. That is, the pulley 113 and the pulley 114 function as main rotation pulleys for a pitch motion of the first jaw 101. Here, the wire 301, which is a first jaw wire, is wound around the pulley 113, and the wire 305, which is a first jaw wire, is wound around the pulley 114.

The pulley 115 and the pulley 116 function as end tool first jaw sub-pulleys. That is, the pulley 115 and the pulley 116 function as sub rotation pulleys for a pitch motion of the first jaw 101. Here, the wire 301, which is a first jaw wire, is wound around the pulley 115, and the wire 305, which is a first jaw wire, is wound around the pulley 116.

Here, the pulley 113 and the pulley 114 are disposed on one side of the pulley 111 and the pulley 112 to face each other. Here, the pulley 113 and the pulley 114 are formed to be rotatable independently of each other around the rotation shaft 143 that is an end tool pitch rotation shaft. In addition, the pulley 115 and the pulley 116 are disposed on one side of the pulley 113 and on one side of the pulley 114, respectively, to face each other. Here, the pulley 115 and the pulley 116 are formed to be rotatable independently of each other around the rotation shaft 144 that is an end tool pitch auxiliary rotation shaft. Here, in the drawings, it is illustrated that the pulley 113, the pulley 115, the pulley 114, and the pulley 116 are all formed to be rotatable around a Y-axis direction, but the concept of the present disclosure is not limited thereto, and the rotation axes of the respective pulleys may be formed in various directions according to configurations thereof.

The wire 301, which is a first jaw wire, is sequentially wound to make contact with at least portions of the pulley 115, the pulley 113, and the pulley 111. In addition, the wire 305 connected to the wire 301 by the coupling member 323 is sequentially wound to make contact with at least portions of the pulley 111, the pulley 112, the pulley 114, and the pulley 116 in turn.

Viewed from another perspective, the wires 301 and 305, which are first jaw wires, are sequentially wound to make contact with at least portions of the pulley 115, the pulley 113, the pulley 111, the pulley 112, the pulley 114, and the pulley 116 and are formed to move along the above pulleys while rotating the above pulleys.

Accordingly, when the wire 301 is pulled in the direction of an arrow 301 of FIG. 7, a coupling member (not shown) to which the wire 301 is coupled and the pulley 111 coupled to the coupling member (not shown) are rotated in an arrow L direction of FIG. 7. In contrast, when the wire 305 is pulled in the direction of an arrow 305 of FIG. 7, a coupling member (not shown) to which the wire 305 is coupled and the pulley 111 coupled to the coupling member (not shown) are rotated in an arrow R direction of FIG. 7.

Hereinafter, the pulley 112 and the pulley 122 serving as auxiliary pulleys will be described in more detail.

The pulley 112 and the pulley 122 may serve to increase rotation angles of the first jaw 101 and the second jaw 102, respectively, by coming into contact with the wire 305, which is a first jaw wire, and the wire 302, which is a second jaw wire, and changing the arrangement paths of the wires 305 and 302 to a certain extent.

That is, when the auxiliary pulleys are not disposed, each of the first jaw and the second jaw may be rotated up to a right angle, but in an embodiment of the present disclosure, the pulley 112 and the pulley 122, which are auxiliary pulleys, are additionally provided, so that the maximum rotation angle may be increased by θ as shown in FIG. 7. This enables a motion of the two jaws of the end tool 120 being opened for an actuation motion while the two jaws are yaw-rotated by 90° in the L direction. This is because the second jaw 102 is rotated by the additional angle θ as shown in FIG. 7. Similarly, an actuation motion is possible even when the two jaws are yaw-rotated in the R direction. In other words, a feature of increasing the range of yaw rotation in which an actuation motion is possible may be obtained through the pulley 112 and the pulley 122.

This will be described below in more detail.

When the auxiliary pulleys are not disposed, since the first jaw wire is fixedly coupled to the end tool first jaw pulley, and the second jaw wire is fixedly coupled to the end tool second jaw pulley, each of the end tool first jaw pulley and the end tool second jaw pulley may be rotated up to 90°. In this case, when the actuation motion is performed while the first jaw and the second jaw are located at a 90° line, the first jaw may be opened, but the second jaw may not be rotated beyond 90°. Accordingly, when the first jaw and the second jaw perform a yaw motion over a certain angle, there was a problem that the actuation motion is not smoothly performed.

In order to address such a problem, in the multi-joint type surgical device 30 of the present disclosure, the pulley 112 and the pulley 122, which are auxiliary pulleys, are additionally disposed at one side of the pulley 111 and one side of the pulley 121, respectively. As described above, as the arrangement paths of the wire 305, which is a first jaw wire, and the wire 302, which is a second jaw wire, are changed to a certain extent by disposing the pulley 112 and the pulley 122, a tangential direction of the wires 305 and 302 is changed, and accordingly, the coupling member 326 for coupling the wire 302 and the pulley 121 may be rotated up to a line N of FIG. 7. That is, the coupling member 326, which is a coupling part of the wire 302 and the pulley 121, is rotatable until the coupling member 326 is located on a common internal tangent of the pulley 121 and the pulley 122. Similarly, the coupling member 323, which is a coupling part of the wire 305 and the pulley 111, is rotatable until the coupling member 323 is located on a common internal tangent of the pulley 111 and the pulley 112, so that the range of rotation in the L direction may be increased.

In other words, by the pulley 112, the wires 301 and 305, which are two strands of the first jaw wire wound around the pulley 111, are disposed at one side with respect to a plane perpendicular to the Y-axis and passing through the X-axis. Simultaneously, by the pulley 122, the wires 302 and 306, which are two strands of the second jaw wire wound around the pulley 121, are disposed at the other side with respect to the plane perpendicular to the Y-axis and passing through the X-axis.

In other words, the pulley 113 and the pulley 114 are disposed at one side with respect to the plane perpendicular to the Y-axis and passing through the X-axis, and the pulley 123 and the pulley 124 are disposed at the other side with respect to the plane perpendicular to the Y-axis and passing through the X-axis.

In other words, the wire 305 is located on the internal tangent of the pulley 111 and the pulley 112, and the rotation angle of the pulley 111 is increased by the pulley 112. In addition, the wire 302 is located on the internal tangent of the pulley 121 and the pulley 122, and the rotation angle of the pulley 121 is increased by the pulley 122.

According to the present disclosure, as the rotation radii of the jaw 101 and the jaw 102 increase, an effect of increasing a yaw motion range in which a normal opening/closing actuation motion is performed may be obtained.

Next, components related to the rotation of the pulley 121 will be described.

The pulley 123 and the pulley 124 function as end tool second jaw pitch main pulleys. That is, the pulley 123 and the pulley 124 function as main rotation pulleys for a pitch motion of the second jaw 102. Here, the wire 306, which is a second jaw wire, is wound around the pulley 123, and the wire 302, which is a second jaw wire, is wound around the pulley 124.

The pulley 125 and the pulley 126 function as end tool second jaw sub-pulleys. That is, the pulley 125 and the pulley 126 function as sub rotation pulleys for a pitch motion of the second jaw 102. Here, the wire 306, which is a second jaw wire, is wound around the pulley 125, and the wire 302, which is a second jaw wire, is wound around the pulley 126.

On one side of the pulley 121, the pulley 123 and the pulley 124 are disposed to face each other. Here, the pulley 123 and the pulley 124 are formed to be rotatable independently of each other around the rotation shaft 143 that is an end tool pitch rotation shaft. In addition, the pulley 125 and the pulley 126 are disposed on one side of the pulley 123 and one side of the pulley 124, respectively, to face each other. Here, the pulley 125 and the J15 pulley 123J25 are formed to be rotatable independently of each other around the rotation shaft 144, which is an end tool pitch auxiliary rotation shaft. Here, in the drawings, it is illustrated that all of the pulley 123, the pulley 125, the pulley 124, and the pulley 126 are formed to be rotatable around the Y-axis direction, but the concept of the present disclosure is not limited thereto, and the rotation axes of the respective pulleys may be formed in various directions according to configurations thereof.

The wire 306, which is a second jaw wire, is sequentially wound to make contact with at least portions of the pulley 125, the pulley 123, and the pulley 121. In addition, the wire 302 connected to the wire 306 by the coupling member 326 is sequentially wound to make contact with at least portions of the pulley 121, the pulley 122, the pulley 124, and the pulley 126.

Viewed from another perspective, the wires 306 and 302, which are second jaw wires, are sequentially wound to make contact with at least portions of the pulley 125, the pulley 123, the pulley 121, the pulley 122, the pulley 124, and the pulley 126, and are formed to move along the above pulleys while rotating the above pulleys.

Accordingly, when the wire 306 is pulled in the direction of an arrow 306 of FIG. 7, the coupling member 326 to which the wire 306 is coupled and the pulley 121 coupled to the coupling member 326 are rotated in the arrow R direction of FIG. 7. In contrast, when the wire 302 is pulled in the direction of an arrow 302 of FIG. 6, the coupling member 326 to which the wire 302 is coupled and the pulley 121 coupled to the coupling member 326 are rotated in the arrow L direction of FIG. 7.

Hereinafter, a pitch motion of the present disclosure will be described in more detail.

First, for the pitch motion, at the end tool 100 side, the pulley 113, the pulley 114, the pulley 123, and the pulley 124, which are end tool jaw pitch main pulleys, are formed to be rotatable around the rotation shaft 143. Meanwhile, in a direction of the proximal end 105 of the end tool jaw pitch main pulley, the pulley 115, the pulley 116, the pulley 125, and the pulley 126, which are end tool jaw pitch sub-pulleys, are formed to be rotatable around the rotation shaft 144.

In addition, based on a plane perpendicular to the rotation shaft 141 and including the rotation shaft 143 (i.e., an XY plane), the wires 301 and 305, which are two strands of the first jaw wire, are located on the same side with respect to the XY plane That is, the wire 301 and the wire 305 are formed to pass through lower sides of the pulley 113 and the pulley 114, which are end tool jaw pitch main pulleys, and upper sides of the pulley 115 and the pulley 116, which are end tool jaw pitch sub-pulleys.

Similarly, the wires 302 and 306, which are two strands of the second jaw wire, are located on the same side with respect to the XY plane. That is, the wires 302 and 306 are formed to pass through upper sides of the pulley 123 and the pulley 124, which are end tool jaw pitch main pulleys, and lower sides of the pulley 125 and the pulley 126, which are end tool jaw pitch sub-pulleys.

In addition, in the wires 301 and 305 that are two strands of the first jaw wire, when the wire 301 is pulled toward the arrow 301 of FIG. 7 and simultaneously the wire 305 is pulled toward the arrow 305 of FIG. 7 (i.e., when both strands of the first jaw wire are pulled in the same direction), as shown in FIG. 5, since the wires 301 and 305 are wound around lower portions of the pulleys 113 and 114, which are rotatable around the rotation shaft 143 that is an end tool pitch rotation shaft, the pulley 111 to which the wire 301 and the wire 305 are fixedly coupled, and the end tool hub 106 to which the pulley 111 is coupled are rotated together as a whole in a counterclockwise direction around the rotation shaft 143, as a result, the end tool 100 performs the pitch motion while rotating downward. At this time, since the second jaw 102 and the wires 302 and 306 fixedly coupled thereto are wound around the upper portions of the pulleys 123 and 124 rotatable around the rotation shaft 143, the wires 302 and 306 are unwound in opposite directions of the arrows 302 and 306, respectively.

In contrast, in the wires 302 and 306 that are two strands of the second jaw wire, when the wire 302 is pulled toward the arrow 302 of FIG. 7 and simultaneously the wire 306 is pulled toward the arrow 306 of FIG. 7 (i.e., when both strands of the second jaw wire are pulled in the same direction), as shown in FIG. 5, since the wires 302 and 306 are wound around upper portions of the pulleys 123 and 124, which are rotatable around the rotation shaft 143 that is an end tool pitch rotation shaft, the pulley 121 to which the wire 302 and the wire 306 are fixedly coupled, and the end tool hub 106 to which the pulley 121 is coupled are rotated together as a whole in a clockwise direction around the rotation shaft 143, as a result, the end tool 100 performs the pitch motion while rotating upward. At this time, since the first jaw 101 and the wires 301 and 305 fixedly coupled thereto are wound around the lower portions of the pulleys 113 and 114 rotatable around the rotation shaft 143, the wires 302 and 306 are moved in opposite directions of the arrows 301 and 305, respectively.

Viewed from another perspective, it may be also described that both strands of each jaw wire are moved simultaneously in the same direction when the end tool 100 is pitch-rotated.

Meanwhile, the end tool 100 of the multi-joint type surgical device 30 of the present disclosure may further include the pulley 131, which is an end tool pitch pulley, the driving part 200 may further include the pulley 231, which is a driving part pitch pulley, and the power transmission part 300 may further include the wire 303 and the wire 304 that are pitch wires. In detail, the pulley 131 of the end tool 100 is rotatable around the rotation shaft 143, which is an end tool pitch rotation shaft, and may be integrally formed with the end tool hub 106 (or fixedly coupled to the end tool hub 106) as one body. In addition, the wires 303 and 304 may serve to connect the pulley 131 of the end tool 100 and the pulley 231 of the driving part 200.

Thus, when the pulley 231 of the driving part 200 is rotated, the rotation of the pulley 231 is transmitted to the pulley 131 of the end tool 100 via the wires 303 and 304, which causes the pulley 131 to also be rotated, and as a result, the end tool 100 performs a pitch motion while rotating.

That is, in the multi-joint type surgical device 30 according to the first embodiment of the present disclosure, by providing the pulley 131 of the end tool 100, the pulley 231 of the driving part 200, and the wires 303 and 304 of the power transmission part 300 to transmit power for a pitch motion, the driving force for a pitch motion from the driving part 200 may be more completely transmitted to the end tool 100, thereby improving operation reliability.

Here, a diameter of each of the pulley 113, the pulley 114, the pulley 123, and the pulley 124, which are end tool jaw pitch main pulleys, and a diameter of the pulley 131, which is an end tool pitch pulley, may be the same as each other or different from each other. At this time, a ratio of the diameter of the end tool jaw pitch main pulley to the diameter of the end tool pitch pulley may be the same as a ratio of a diameter of a driving part relay pulley of the driving part 200, which will be described later, to a diameter of a driving part pitch pulley. This will be described in detail below.

(Driving Part)

Hereinafter, the driving part 200 of the multi-joint type surgical device 30 of FIG. 4 will be described in more detail.

Referring to FIGS. 8 to 14, the driving part 200 of the multi-joint type surgical device 30 according to the first embodiment of the present disclosure may include the pulley 211, the pulley 212, a pulley 213, a pulley 214, a pulley 215, a pulley 216, a pulley 217, a pulley 218, a pulley 219, and a pulley 220, which are related to a rotational motion of the first jaw 101 In addition, the driving part 200 may include the pulley 221, the pulley 222, a pulley 223, a pulley 224, a pulley 225, a pulley 226, a pulley 227, a pulley 228, a pulley 229, and a pulley 230, which are related to a rotational motion of the second jaw 102.

Here, the pulleys facing each other are illustrated in the drawings as being formed parallel to each other, but the concept of the present disclosure is not limited thereto, and each of the pulleys may be variously formed with a position and a size suitable for the configuration of the driving part.

In addition, the driving part 200 of the multi-joint type surgical device 30 according to the first embodiment of the present disclosure may further include the pulley 231 serving as a driving part pitch pulley, and a pitch-yaw connector 232 configured to connect the pulley 231 and the above-described jaw pulleys of the driving part.

Further, the driving part 200 of the first embodiment of the present disclosure may include a rotation shaft 241, a rotation shaft 242, a rotation shaft 243, a rotation shaft 244, a rotation shaft 245, and a rotation shaft 246. Here, the rotation shaft 241 may function as a first jaw rotation shaft of the driving part, and the rotation shaft 242 may function as a second jaw rotation shaft of the driving part. In addition, the rotation shaft 243 may function as a driving part pitch rotation shaft, and the rotation shaft 244 may function as a driving part roll rotation shaft. In addition, the rotation shaft 245 may function as a driving part first jaw auxiliary rotation shaft of the driving part, and the rotation shaft 246 may function as a driving part second jaw auxiliary rotation shaft. Each of the rotation shafts 241, 242, 243, 244, 245, and 246 may be fitted into one or more pulleys, which will be described in detail later.

In addition, the driving part 200 of the first embodiment of the present disclosure may include a motor coupling part 251, a motor coupling part 252, a motor coupling part 253, and a motor coupling part 254. Here, the motor coupling part 251 may function as a first jaw driving motor coupling part, the motor coupling part 252 may function as a second jaw driving motor coupling part, the motor coupling part 253 may function as a pitch driving motor coupling part, and the motor coupling part 254 may function as a roll driving motor coupling part. Here, each of the motor coupling parts 251, 252, 253, and 254 may be formed in the form of a rotatable flat plate, in which one or more coupling holes to which a motor (not shown) may be coupled may be formed.

The motor coupling parts 251, 252, 253, and 254 of the driving part 200 described above are coupled to motors (not shown) formed in the robot arm units 21, 22, and 23, respectively, so that the driving part 200 is operated by driving the motors (not shown).

In addition, the driving part 200 of the first embodiment of the present disclosure may include a gear 261, a gear 262, a gear 263, and a gear 264. Here, the gear 261 and the gear 262 may function as pitch driving gears, and the gear 263 and the gear 264 may function as roll driving gears.

Hereinafter, each component will be described in more detail.

The pulley 211 and the pulley 212 may function as driving part first jaw pulleys, and the pulley 221 and the pulley 222 may function as driving part second jaw pulleys, and these components may be collectively referred to as driving part jaw pulleys.

Here, it is illustrated in the drawings that the pulley 211 is associated with a rotational motion of the first jaw 101 of the end tool 100, and the pulley 221 is associated with a rotational motion of the second jaw 102 of the end tool 100, but the concept of the present disclosure is not limited thereto. For example, one group of pulleys in the driving part may be associated with a yaw motion, and one group of pulleys in the driving part may be associated with an actuation motion. Thus, the pulley 211 and the pulley 212 may be collectively referred to as driving part driving pulleys. In addition, in the other pulleys, one group of pulleys may also be associated with a yaw motion, and one group of pulleys may also be associated with an actuation motion.

The pulley 213 and the pulley 214 may function as driving part first jaw auxiliary pulleys, and the pulley 223 and the pulley 224 may function as driving part second jaw auxiliary pulleys, and these components may be collectively referred to as driving part auxiliary pulleys.

The pulley 215 and the pulley 216 may function as driving part first jaw first relay pulleys, and the pulley 217 and the pulley 218 may function as driving part first jaw second relay pulleys, and these components may be collectively referred to as driving part first jaw relay pulleys. Meanwhile, the pulley 225 and the pulley 226 may function as driving part second jaw first relay pulleys, and the pulley 227 and the pulley 228 may function as driving part second jaw second relay pulleys, and these components may be collectively referred to as driving part second jaw relay pulleys. Meanwhile, the pulley 215, the pulley 216, the pulley 225, and the pulley 226 may be collectively referred to as driving part first relay pulleys, and the pulley 217, the pulley 218, the pulley 227, and the pulley 228 may be collectively referred to as driving part second relay pulleys. Furthermore, the pulley 215, the pulley 216, the pulley 217, the pulley 218, the pulley 225, the pulley 226, the pulley 227, and the pulley 228 may be collectively referred to as driving part relay pulleys.

Here, it is illustrated in the drawings that two pulleys are paired to form the driving part relay pulleys for each jaw, but the concept of the present disclosure is not limited thereto. For example, it is illustrated that the pulley 215, which is a driving part first jaw first relay pulley, and the pulley 217, which is a driving part first jaw second relay pulley, are formed as a pair, and the wire 301 sequentially passes through the pulley 215 and the pulley 217. However, the driving part first jaw relay pulley may be configured with not just two pulleys but also with three or more pulleys Meanwhile, the pulley 219 and the pulley 220 may function as driving part first jaw satellite pulleys, and the pulley 229 and the pulley 230 may function as driving part second jaw satellite pulleys, and these two components may be collectively referred to as driving part satellite pulleys.

A plurality of rotation shafts including the rotation shaft 241, the rotation shaft 242, the rotation shaft 243, the rotation shaft 244, the rotation shaft 245, and the rotation shaft 246 may be formed on a first surface of a base plate 201. In addition, a plurality of relay pulleys 202 are formed on the first surface of the base plate 201, and may serve to redirect the wires 301, 302, 303, 304, 305, and 306 entering the driving part 200 through the connection part 310 toward the pulley 231.

Further, the connection part 310 in the form of a shaft is coupled to a second surface of the base plate 201 opposite to the first surface, and the motor coupling part 251, the motor coupling part 252, the motor coupling part 253, and the motor coupling part 254, to which the motors (not shown) for driving the pulleys are coupled, may be formed on the second surface.

Here, each rotation shaft and each motor coupling part may be directly connected or indirectly connected via a gear.

In an example, by directly coupling the motor coupling part 251, which is a first jaw driving motor coupling part, to the rotation shaft 241 that is a driving part first jaw rotation shaft, when the motor coupling part 251 coupled to a first jaw driving motor (not shown) is rotated, the rotation shaft 241 directly coupled to the motor coupling part 251 may be rotated together. Similarly, by directly coupling the motor coupling part 252, which is a second jaw driving motor coupling part, to the rotation shaft 242 that is a driving part second jaw rotation shaft, when the motor coupling part 252 coupled to a second jaw driving motor (not shown) is rotated, the rotation shaft 242 directly coupled to the motor coupling part 252 may be rotated together.

In another example, when viewed from a plane perpendicular to the rotation shaft 243, the motor coupling part 253, which is a pitch driving motor coupling part, and the rotation shaft 243, which is a driving part pitch rotation shaft, may be disposed to be spaced apart from each other by a certain extent. In addition, the motor coupling part 253 and the rotation shaft 243 may be connected by the gears 261 and 263, which are pitch driving gears.

Similarly, when viewed from a plane perpendicular to the rotation shaft 244, the motor coupling part 254, which is a roll driving motor coupling part, and the rotation shaft 244, which is a driving part roll rotation shaft, may be disposed to be spaced apart from each other by a certain extent. In addition, the motor coupling part 254 and the rotation shaft 244 may be connected by the gears 263 and 264, which are roll driving gears.

As such, some motor coupling parts are configured to be directly connected to the rotation shafts, respectively, and the remaining motor coupling parts are configured to be indirectly connected to the rotation shafts, respectively, because the coupling position and direction between the multi-joint type surgical device 30 and the slave robot 20 should be considered. That is, the rotation shaft that is not affected by the coupling position with the slave robot 20 is directly connected to the motor coupling part, whereas the rotation shaft that may cause interference with the coupling position with the slave robot 20 may be indirectly connected to the motor coupling part.

It is illustrated in the drawings that the motor coupling part 251 and the motor coupling part 252 are directly connected to the rotation shafts, respectively, and the motor coupling part 253 and the motor coupling part 254 are indirectly connected, respectively, through the gears, but the concept of the present disclosure is not limited thereto, and various configurations are possible according to the coupling position and direction with the slave robot 20.

The pulleys 211 and 212, which are driving part first jaw pulleys, may be coupled to the rotation shaft 241, which is a driving part first jaw rotation shaft. Here, the pulleys 211 and 212 may be formed to rotate together with the rotation shaft 241.

In addition, the rotation shaft 245, which is a driving part first jaw auxiliary rotation shaft, may be disposed in a region adjacent to the rotation shaft 241. The pulleys 213 and 214, which are driving part first jaw auxiliary pulleys, may be coupled to the rotation shaft 245. Here, the pulleys 213 and 214 may be formed to be rotatable around the rotation shaft 245.

Here, it is illustrated in the drawings that the driving part first jaw pulley is formed of two pulleys 211 and 212, the wire 301 is coupled to one pulley 211, and the wire 305 is coupled to the other pulley 212. However, the concept of the present disclosure is not limited thereto, and the driving part first jaw pulley may be formed of one pulley, and both the wires 301 and 305 may be coupled to the one pulley.

As described above, the rotation shaft 241 is coupled to the first jaw driving motor (not shown) by the motor coupling part 251, and thus, when the first jaw driving motor (not shown) rotates for driving the first jaw 101, the pulleys 211 and 212, which are driving part first jaw pulleys, are rotated together with the rotation shaft 241, so that the wires 301 and 305, which are first jaw wires, are pulled or released.

The pulleys 221 and 222, which are driving part second jaw rotation shafts, may be coupled to the rotation shaft 242 that is a driving part second jaw pulley. Here, the pulley 221 and the pulley 222 may be formed to rotate together with the rotation shaft 242.

In addition, the rotation shaft 246, which is a driving part second jaw auxiliary rotation shaft, may be disposed in a region adjacent to the rotation shaft 242. The pulleys 223 and 224, which are driving part second jaw auxiliary pulleys, may be coupled to the rotation shaft 245. Here, the pulleys 223 and 224 may be formed to be rotatable around the rotation shaft 246.

Here, it is illustrated in the drawings that the driving part second jaw pulley is formed of two pulleys 221 and 222, the wire 302 is coupled to one pulley 221, and the wire 306 is coupled to the other pulley 222. However, the concept of the present disclosure is not limited thereto, and the driving part second jaw pulley may be formed of one pulley, and both the wires 302 and 306 may be coupled to the one pulley.

As described above, the rotation shaft 242 is coupled to the second jaw driving motor (not shown) by the motor coupling part 252, and thus, when the second jaw driving motor (not shown) rotates for driving the second jaw 102, the pulley 221 and the pulley 222, which are driving part second jaw pulleys, are rotated together with the rotation shaft 242, so that the wires 302 and 306, which are second jaw wires, are pulled or released.

The pulley 231, which is a driving part pitch pulley, may be coupled to the rotation shaft 243 that is a driving part pitch rotation shaft. Here, the pulley 231 may be formed to rotate together with the rotation shaft 243.

As described above, the rotation shaft 243 is coupled to a pitch driving motor (not shown) by the motor coupling part 253, and thus, when the pitch driving motor (not shown) rotates for a pitch motion, the wires 303 and 304, which are pitch wires, are pulled or released as the pulley 231, which is a driving part pitch pulley, is rotated together with the rotation shaft 243.

Meanwhile, the pulley 215, the pulley 216, the pulley 217, the pulley 218, the pulley 225, the pulley 226, the pulley 227, and the pulley 228, which are driving part relay pulleys, may be formed to be rotatable around the rotation shaft 243 by inserting the rotation shaft 243 therethrough. Here, the pulley 215, the pulley 216, the pulley 217, and the pulley 218, which are driving part first jaw relay pulleys, may be disposed on one surface side of the pulley 231 that is a pitch pulley, and the pulley 225, the pulley 226, the pulley 227, and the pulley 228, which are driving part second jaw relay pulleys, may be disposed on the other surface side of the pulley 231.

Viewed from another perspective, along the rotation shaft 243, the pulleys 225 and 226, which are driving part second jaw first relay pulleys, the pulleys 227 and 228, which are driving part second jaw second relay pulleys, the pulley 231, which is a driving part pitch pulley, and the pulleys 217 and 218, which are driving part first jaw second relay pulleys, and the pulleys 215 and 216, which are driving part first jaw first relay pulleys, are sequentially stacked and formed.

In addition, the pitch-yaw connector 232 may be coupled to the rotation shaft 243. The pitch-yaw connector 232 may be formed to rigidly connect the pulley 231, which is a driving part pitch pulley, to the pulley 219, the pulley 220, the pulley 229, and the pulley 230, which are driving part satellite pulleys to allow the driving part satellite pulleys to be revolved around the rotation shaft 243 when the pulley 231 is rotated. This will be described in more detail later.

Here, the pitch-yaw connector 232 may be formed to rotate together with the rotation shaft 243. That is, the pulley 231 and the pitch-yaw connector 232 may be coupled to the rotation shaft 243, and may be rotated together with the rotation shaft 243.

Here, the pitch-yaw connector 232 may be described as being formed in an approximately Y-shape as shown in FIG. 10, or the pitch-yaw connector 232 may be described as being formed in a shape in which at least two extension portions 232*a* and 232*b* are formed to extend from the center thereof. In addition, a driving part first jaw satellite pulley central shaft 233 and a driving part second jaw satellite pulley central shaft 234 may be formed at end portions of the extension portions 232*a* and 232*b*, respectively.

In addition, the pulleys 219 and 220, which are driving part first jaw satellite pulleys, may be coupled to the driving part first jaw satellite pulley central shaft 233, and the pulleys 229 and 230, which are driving part second jaw satellite pulleys, may be coupled to the driving part second jaw satellite pulley central shaft 234.

As a result, when the pulley 231, which is a driving part pitch pulley, is rotated together with the rotation shaft 243, the pulley 219, the pulley 220, the pulley 229, and the pulley 230, which are driving part satellite pulleys, are revolved around the rotation shaft 243. In other words, it may be said that the driving part first jaw satellite pulley central shaft 233 and the driving part second jaw satellite pulley central shaft 234 are rotated around the rotation shaft 243 while maintaining a constant distance from the rotation shaft 243 in a state in which the driving part first jaw satellite pulley central shaft 233 and the driving part second jaw satellite pulley central shaft 234 are spaced apart from the rotation shaft 243 by a certain extent.

That is, the driving part satellite pulley is formed to be movable relative to the driving part relay pulley and the rotation shaft 243 so that a relative position of the driving part satellite pulley with respect to the driving part relay pulley and the rotation shaft 243 may be changed. On the other hand, the relative positions of the driving part pitch pulley and the driving part relay pulley remain constant.

In addition, when the pulley 231, which is a driving part pitch pulley, is rotated around the rotation shaft 243, the pulley 219, the pulley 220, the pulley 229, and the pulley 230, which are driving part satellite pulleys, are moved relative to the pulley 231, which is a driving part pitch pulley, so that the overall lengths of the wire 301, the wire 302, the wire 305, and the wire 306, which are jaw wires, in the driving part 200 are changed.

The wire 301, which is a first jaw wire, is connected to the end tool 100 through the connection part 310 after being sequentially wound to make contact with at least portions of the pulley 211, the pulley 213, the pulley 215, the pulley 219, and the pulley 217 in a state in which one end portion of the wire 301 is coupled to the pulley 211 by the first jaw wire-driving part coupling member (not shown).

Viewed from another perspective, the wire 301, which is a first jaw wire, is connected to the end tool 100 through the connection part 310 after being sequentially passing through the driving part first jaw pulley 211, the driving part first jaw auxiliary pulley 213, the driving part first jaw first relay pulley 215, the driving part first jaw satellite pulley 219, and the driving part first jaw second relay pulley 217.

Viewed from another perspective, the wire 301, which is a first jaw wire, enters the driving part 200 after passing through the end tool 100 and the connection part 310, and then is fixedly coupled to the pulley 211, which is a driving part first jaw pulley after being sequentially wound around the pulley 217, the pulley 219, the pulley 215, and the pulley 213.

Meanwhile, the wire 305, which is a first jaw wire, is connected to the end tool 100 through the connection part 310 after being sequentially wound to make contact with at least portions of the pulley 212, the pulley 214, the pulley 216, the pulley 220, and the pulley 218 in a state in which one end portion of the wire 305 is coupled to the pulley 212 by the first jaw wire-driving part coupling member (not shown).

The wire 302, which is a second jaw wire, is connected to the end tool 100 through the connection part 310 after being sequentially wound to make contact with at least portions of the pulley 221, the pulley 223, the pulley 225, the pulley 229, and the pulley 227 in a state in which one end portion thereof is coupled to the pulley 221 by the second jaw wire-driving part coupling member (not shown).

Meanwhile, the wire 306, which is a second jaw wire, is connected to the end tool 100 through the connection part 310 after being sequentially wound to make contact with at least portions of the pulley 222, the pulley 224, the pulley 226, the pulley 230, and the pulley 228 in a state in which one end portion thereof is coupled to the pulley 222 by the second jaw wire-driving part coupling member (not shown).

(Pitch Motion)

FIGS. 15 and 16 are views illustrating a pitch motion of the multi-joint type surgical device illustrated in FIG. 4. Here, for convenience of description, only the pulleys and wires related to the rotation of the first jaw are illustrated in FIGS. 15A and 16A, and only the pulleys and wires related to the rotation of the second jaw are illustrated in FIGS. 15B and 16B. In addition, FIGS. 15C and 16C illustrate a pitch motion of the end tool according to a pitch motion of the driving part.

Here, in the multi-joint type surgical device 30 according to an embodiment of the present disclosure, when the driving part satellite pulley is moved relative to the driving part relay pulley, which causes the overall length of the jaw wire to be changed in the driving part 200, allowing the end tool 100 to perform a pitch motion. In particular, in the multi-joint type surgical device 30 according to an embodiment of the present disclosure, when the driving part pitch pulley is rotated, which causes the driving part satellite pulley to be revolved around the (common) rotation shaft of the driving part relay pulley and the driving part pitch pulley so that a path length of the jaw wire wound around the driving part relay pulley is changed, allowing the end tool to perform a pitch motion.

In detail, when a motion compensation for the pitch motion is not separately performed in the driving part, the pitch motion itself cannot be performed in the end tool.

Figure 33:
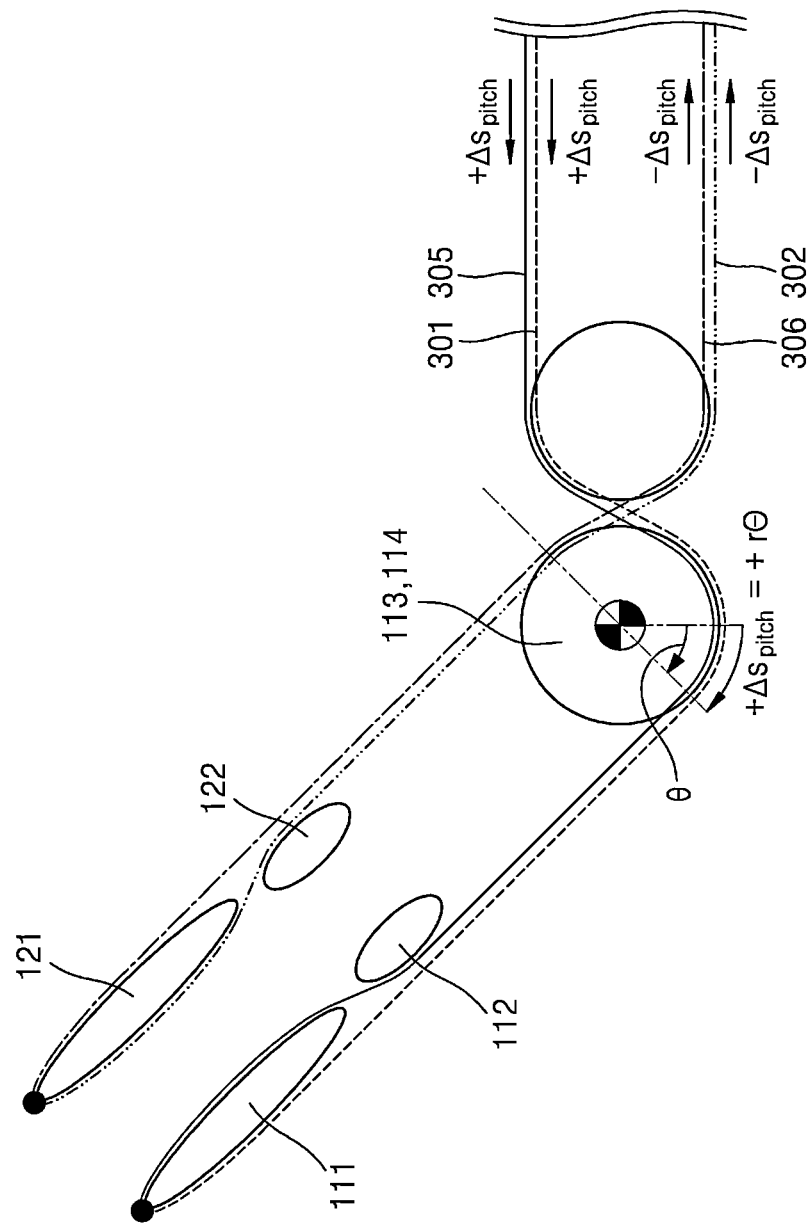
FIG. 33 is a conceptual diagram illustrating pitch motion compensation of the multi-joint type surgical device according to an embodiment of the present disclosure.

Referring to FIG. 33, which is a conceptual diagram illustrating pitch motion compensation, in order for the end tool to perform a pitch motion, the wires 301 and 305 should be further wound around the pulley 113 by $\Delta S_{pitch}$ and the wires 302 and 306 should be further unwound from the pulley 114 by $\Delta S_{pitch}$. However, when such compensation is not performed in the driving part, the pitch motion itself cannot be performed in the end tool.

In order to perform motion compensation for the pitch motion as described above, in the multi-joint type surgical device 30 according to an embodiment of the present disclosure, the driving part pitch pulleys are rotated while the driving part satellite pulleys are revolved, so that the jaw wires are wound around or released from the driving part relay pulley, which allows the movement of the jaw wires to be compensated for by the rotation of the driving part pitch pulley.

In other words, when the pulley 231, which is a driving part pitch pulley, is rotated together with the rotation shaft 243, the driving part satellite pulleys are revolved around the rotation shaft 243. In addition, as the driving part satellite pulleys are revolved around the rotation shaft 243, the jaw wire wound around the driving part relay pulley is changed in length. That is, the jaw wire wound at the end tool 100 side due to the rotation of the pulley 231 is released by the same amount at the driving part 200 side, and the jaw wire unwound at the end tool 100 side is wound by the same amount at the driving part 200 side, so that the pitch motion does not affect the yaw motion.

Viewed from another perspective, when the end tool performs a pitch motion due to the rotation of the driving part pitch pulley, the jaw wire (responsible for the yaw and actuation motions) is also moved by the pitch motion. That is, as the pitch rotation is performed around the rotation shaft 143 of the end tool 100, both strands of the jaw wire coupled to one jaw are pulled, and both strands thereof coupled to the other jaw are released. Accordingly, it may be described that in the present disclosure, in order to compensate for the movement of the jaw wire, when the end tool performs the pitch motion, the overall length of the jaw wire in the driving part is changed while the driving part satellite pulley is moved relative to the driving part relay pulley, so that the jaw wire is released (or pulled) at the end tool side as much as the jaw wire is pulled (or released) at the driving part side, thereby compensating for the movement of the jaw wire when the end tool performs the pitch motion.

Hereinafter, the pitch motion will be described in more detail.

When the pulley 231, which is a driving part pitch pulley, is rotated in the direction of an arrow A1 (i.e., in the clockwise direction in the drawing) in order for the pitch motion, the pitch-yaw connector 232 (see FIG. 8) is rotated in the direction of the arrow A1 together with the pulley 231, and thus, the pulleys 219 and 220, which are driving part satellite pulleys fixedly coupled to the pitch-yaw connector 232 (see FIG. 8), are revolved as a whole in the direction of an arrow A2 of FIG. 16A (i.e., in the clockwise direction in the drawing) around the rotation shaft 243 by θ. That is, when the pulley 231 is rotated, the pulleys 219 and 220 are rotated by θ from the position of P1 of FIG. 15A to the position of P2 of FIG. 16A. Viewed from another perspective, it may be described that when the driving part pitch pulley is rotated, the driving part satellite pulley is moved in conjunction with the driving part pitch pulley.

At the same time, when the pulley 231, which is a driving part pitch pulley, is rotated in the direction of the arrow A1 (i.e., in the clockwise direction in the drawing), the pitch-yaw connector 232 (see FIG. 8) is rotated in the direction of the arrow A1 together with the pulley 231, and thus, the pulleys 229 and 230, which are driving part satellite pulleys fixedly coupled to the pitch-yaw connector 232 (see FIG. 8), are revolved as a whole in the direction of an arrow A3 of FIG. 16B (i.e., in the clockwise direction in the drawing) around the rotation shaft 243 by θ. That is, when the pulley 231 is rotated, the pulleys 229 and 230 are rotated by θ from the position of P3 of FIG. 15B to the position of P4 of FIG. 16B. Viewed from another perspective, it may be described that when the driving part pitch pulley is rotated, the driving part satellite pulley is moved in conjunction with the driving part pitch pulley.

Meanwhile, in this case, the positions of the pulley 215, the pulley 216, the pulley 217, the pulley 218, the pulley 225, the pulley 226, the pulley 227, and the pulley 228, which are driving part relay pulleys coupled to the rotation shaft 243, are not changed. That is, the relative positions of the pulley 211, which is a driving part jaw pulley, the pulley 231, which is a driving part pitch pulley, and the pulley 215, the pulley 216, the pulley 217, and the pulley 218, which are driving part relay pulleys, remain constant. Similarly, the relative positions of the pulley 221, which is a driving part jaw pulley, the pulley 231, which is a driving part pitch pulley, and the pulley 225, the pulley 226, the pulley 227, and the pulley 228, which are driving part relay pulleys, remain constant.

In addition, as described above, the relative position of the driving part satellite pulley with respect to the driving part relay pulley is changed as the driving part satellite pulley is revolved, and thus, the length of each wire wound around the driving part relay pulley, that is, the path length, is changed. Here, since the driving part relay pulley includes the pulley 215, which is a driving part first jaw first relay pulley, and the pulley 217, which is a driving part first jaw second relay pulley, the path length also means the sum of the length of the wire 301 wound around the pulley 215 and the length of the wire 301 wound around the pulley 217 (or, the sum of the length by which the wire 305 is wound around the pulley 216 and the length by which the wire 305 is wound on the pulley 218).

That is, as compared to a path length L1 by which the wires 301 and 305, which are first jaw wires, wound around the driving part relay pulleys at the position of FIG. 15A, a path length L2 by which the first jaw wires wound around the driving part relay pulleys at the position of FIG. 16A is reduced, and thus, the first jaw wires are further released at the driving part 200 side by the reduced path length (L1−L2). That is, the overall lengths of the wires 301 and 305, which are first jaw wires, in the driving part 200 are reduced. In addition, as the overall length of the first jaw wire in the driving part 200 is reduced, the overall length of the first jaw wire in the end tool 100 is increased as much as the first jaw wire is unwound.

In contrast, when the pulley 231, which is a driving part pitch pulley, is rotated in the direction of the arrow A1, as compared to a path length L3 by which the wires 302 and 306, which are second jaw wires, wound around the driving part relay pulleys at the position of FIG. 15B, a path length L4 by which the second jaw wires wound around the driving part relay pulleys at the position of FIG. 16B is increased, and the second jaw wires are further pulled at the driving part 200 side by as much as the increased path length (L4−L3). That is, the overall lengths of the wires 302 and 306, which are second jaw wires, in the driving part 200 are increased. In addition, as the overall length of the second jaw wire in the driving part 200 is increased, the overall length of the second jaw wire in the end tool 100 is reduced as much as the second jaw wire is pulled.

As such, when the pulley 231, which is a driving part pitch pulley, is rotated in the direction of the arrow A1 for a pitch motion, the relative position of the driving part satellite pulley is changed as the driving part satellite pulley is moved relative to the driving part pitch pulley and the driving part relay pulley. In addition, due to the relative movement of the driving part satellite pulley, the overall length of the first jaw wire in the driving part 200 is reduced, and the overall length of the first jaw wire in the end tool 100 is increased. At the same time, due to the relative movement of the driving part satellite pulley, the overall length of the second jaw wire in the driving part 200 is increased, and the overall length of the second jaw wire in the end tool 100 is reduced.

As a result, when the pulley 231, which is a driving part pitch pulley, is rotated in the direction of the arrow A1, the wires 301 and 305, which are two strands of the first jaw wire, are released and the wires 302 and 306, which are two strands of the second jaw wire, are pulled when viewed from the end tool 100 side, so that the end tool 100 performs a pitch motion in the direction of an arrow A4 around the rotation shaft 143.

Here, the term "path length" may be defined as a length of the jaw wire from a point at which the jaw wire enters the driving part first relay pulley to a point at which the jaw wire exits from the driving part second relay pulley through the driving part satellite pulley. That is, the path length may be defined as a length of the wire 301, which is a jaw wire, from a point at which the jaw wire enters the pulley 215, which is a driving part first relay pulley, to a point at which the jaw wire exits from the pulley 217, which is a driving part second relay pulley, through the pulley 219 that is a driving part satellite pulley.

Viewed from another perspective, the path length may be defined as the length of the jaw wire from an initial contact point of the jaw wire with the driving part relay pulley to a final contact point of the jaw wire with the driving part relay pulley on a deployment path of the jaw wire that connects the end tool jaw pulley to the driving part jaw pulley. That is, the path length may be defined as the length of the jaw wire from an initial contact point of the wire 301, which is a jaw wire, with the pulley 215, which is a driving part first relay pulley, to a final contact point of the wire 301 with the pulley 217, which is a driving part second relay pulley.

Meanwhile, as the above-described path length is changed while the driving part satellite pulley is moved relative to the driving part relay pulley, the overall length of the jaw wire in the driving part 200 is also changed. In addition, as the overall length of the jaw wire in the driving part 200 is changed, the overall length of the jaw wire in the end tool 100 is also changed. However, it may be said that since the overall length of the jaw wire in the end tool 100 is also increased (or reduced) by as much as the overall length of the jaw wire increased (reduced) in the driving part 200, a total length of the jaw wire is not changed (assuming that elastic deformation or the like is not considered).

As a result, when the driving part pitch pulley is rotated, the wire 301/wire 305, which are first jaw wires, are released at the driving part 200 side by as much as the wire 301/wire 305, which are first jaw wires, are pulled at the end tool 100 side, as a result, a pitch motion is enabled.

Meanwhile, as described above, the end tool 100 of the multi-joint type surgical device 30 of the present disclosure may further include the pulley 131, which is an end tool pitch pulley, the driving part 200 may further include the pulley 231, which is a driving part pitch pulley, and the power transmission part 300 may further include the wire 303 and the wire 304 which are pitch wires.

Accordingly, when the pulley 231, which is a driving part pitch pulley, is rotated in the direction of the arrow A1, due to the rotation of the pulley 231, the wire 304 is wound around the pulley 231 and the wire 303 is released from the pulley 231. Accordingly, the pulley 131, which is an end tool pitch pulley connected to the other sides of the wires 303 and 304, is rotated in the direction of the arrow A2 around the rotation shaft 143, so that the pitch motion may be more surely and reliably performed.

(Size Ratio of Pulleys)

Here, among the pulleys that are rotated around the rotation shaft 143, which is an end tool pitch rotation shaft, the pulley 131, which is an end tool pitch pulley in contact with the wires 303 and 304 that are pitch wires, may be formed to have a diameter different from those of the pulley 113, the pulley 114, the pulley 123, and the pulley 124, which are end tool jaw pitch main pulleys in contact with the wire 301, the wire 305, the wire 302, and the wire 306 that are jaw wires.

In this case, when the rotation shaft 143 is rotated, the lengths of the wires wound around or unwound from the respective pulleys are different from each other. For example, when a diameter of the end tool pitch pulley is 6φ, a diameter of the end tool jaw pitch main pulley is 4φ, and the rotation shaft 143 is rotated by 90°, a length of the pitch wire wound around the end tool pitch pulley is 1.5π, whereas a length of the jaw wire wound around the end tool jaw pitch main pulley may be 1π.

From this perspective, the length of the wire wound around or unwound from the pulley may be defined as "rotation amount". The rotation amount is a concept different from a rotation angle, and may be calculated as (diameter*rotation angle/360°*π).

In this case, since essentially the pulley 231, which is a driving part pitch pulley, is directly connected to the pulley 131, which is an end tool pitch pulley, by the wires 303 and 304, which are pitch wires, the rotation amount of the driving part pitch pulley is the same as that of the end tool pitch pulley. That is, the pitch wire is released from or wound around the end tool pitch pulley by as much as the pitch wire is wound around or released from the driving part pitch pulley.

Meanwhile, a relation of (diameter of end tool pitch pulley:diameter of end tool jaw pitch main pulley)=(rotation amount of wire wound around end tool pitch pulley:rotation amount of wire wound around end tool jaw pitch main pulley) may be established.

As described above, when, in the end tool 100, the length of the pitch wire wound around the end tool pitch pulley is different from the length of the jaw wire wound around the end tool jaw pitch main pulley, in the driving part 200, the length of the pitch wire to be released should be different from the length of the jaw wire to be released by the same proportion.

To this end, the relationship of (diameter of end tool pitch pulley:diameter of end tool jaw pitch main pulley)=(diameter of driving part pitch pulley:diameter of driving part relay pulley) may be established.

For example, when a ratio of (diameter of end tool pitch pulley:diameter of end tool jaw pitch main pulley) is 6:4, a ratio of (diameter of driving part pitch pulley:diameter of driving part relay pulley) may also be 6:4. According to this ratio, the diameter of the driving part pitch pulley may be 9φ, and the diameter of the driving part relay pulley may be 6φ.

However, here, the driving part relay pulley may include two or more pulleys including the driving part first relay pulley and the driving part second relay pulley. In addition, the sum of the diameters of the driving part first relay pulley and the driving part second relay pulley may be defined as the diameter of the driving part relay pulley.

For example, when the diameter of the driving part relay pulley is 6φ, there are several possible combinations for (diameter of driving part first relay pulley, diameter of driving part second relay pulley), including (1φ, 5φ), (2φ, 4φ), (3φ, 3φ), (4φ, 2φ), and (5φ, 1φ), among others." Here, it is illustrated in the drawings that the diameter of the pulley 215, which is a driving part first relay pulley, is 4φ, and the diameter of the pulley 217, which is the driving part second relay pulley, is 2φ.

In addition, a relationship of (rotation amount of driving part first relay pulley+rotation amount of driving part second relay pulley) may be described as being proportional to the rotation amount of the driving part pitch pulley.

However, although the ratio of (diameter of end tool pitch pulley:diameter of end tool jaw pitch main pulley) does not exactly match the ratio of (diameter of driving part pitch pulley:diameter of driving part relay pulley), when the pulley diameters are selected to make these ratios similar, the object of the present disclosure, which is to compensate for the movement of the jaw wire with the rotation of the driving part pitch pulley, can be achieved to some extent.

The process of the final pitch motion will be described again as follows.

Hereinafter, a case in which the diameter of the end tool pitch pulley is 6φ, the diameter of the end tool jaw pitch main pulley is 4φ, the diameter of the driving part pitch pulley is 9φ, and the diameter of the driving part relay pulley is 6φ will be described as an example.

First, for a pitch motion, the pulley 231, which is a driving part pitch pulley of the driving part 200, is rotated by 60° to wind the wire 304, which is a pitch wire, while releasing the wire 303. At this time, the length of the wire 303/wire 304 wound and unwound is 1.5π.

Accordingly, as the wire 304 is pulled by 1.5π and the wire 303 is released by 1.5π in the end tool 100, the pulley 131, which is an end tool pitch pulley, is rotated by 90° corresponding to 1.5π.

Meanwhile, when the pulley 131 is pitch-rotated around the rotation shaft 143, the jaws 101 and 102 and the pulley 111/pulley 112 are also pitch-rotated around the rotation shaft 143. Accordingly, the wires 301 and 305, which are first jaw wires coupled to the pulley 111, are both pulled, and the wires 302 and 306, which are second jaw wires coupled to the pulley 121, are both released. At this time, the angles by which the end tool pitch pulley and the end tool jaw pitch main pulley are rotated are equal to each other and measure 90°, and thus, the length of the jaw wires wound around or released from the end tool jaw pitch main pulley becomes 1π.

Meanwhile, since the pulley 231 and the pulley 219/pulley 220 are rigidly connected by the pitch-yaw connector 232, when the pulley 231 is rotated by 60° around the rotation shaft 243, the pulley 219/pulley 220 are revolved by 60° around the rotation shaft 243.

In addition, as described above, as the pulley 219/pulley 220 are revolved, the jaw wires are wound around or released from the pulley 215 and the pulley 216, whose combined diameter is 6φ, by 1π corresponding to a revolution angle of 60°. That is, the wires 301 and 305, which are first jaw wires, are released as a whole, and the wires 302 and 306, which are second jaw wires, are pulled as a whole.

In other words, the overall path lengths of the wires 301 and 305 wound around the pulley 215, the pulley 216, the pulley 217, and the pulley 218, which are driving part first jaw relay pulleys, are reduced, and the wires 301 and 305 are released by as much as the reduced path length. In addition, the overall path lengths of the wires 302 and 306 wound around the pulley 225, the pulley 226, the pulley 227, and the pulley 228, which are driving part second jaw relay pulleys, are increased, and the wires 302 and 306 are pulled by as much as the increased path length.

That is, the wires 301 and 305, which are first jaw wires, are released at the driving part 200 side by as much as the wires 301 and 305 are pulled at the end tool 100 side, thereby compensating for the movement of the jaw wire due to the pitch motion. Similarly, the wires 302 and 306, which are second jaw wires, are released at the driving part 200 side by as much as the wires 302 and 306 are pulled at the end tool 100 side, thereby compensating for the movement of the jaw wire due to the pitch motion.

As a result, by releasing (or pulling) the jaw wires at the driving part 200 side by as much as a length equal to the length by which the jaw wires are wound around (or released from) the end tool 100 side in response to the pitch motion, the pitch motion can be performed independently without affecting the rotation of the jaw around the yaw shaft.

That is, when the driving part pitch pulley and the driving part satellite pulley are rigidly connected, and the driving part pitch pulley is rotated around the rotation shaft 243, the path length of the jaw wire wound around the driving part relay pulley is changed as the driving part satellite pulley is revolved around the rotation shaft 243. In addition, the change in the path length of the jaw wire compensates for the movement of the jaw wires at the end tool side due to the pitch motion, as a result, the pitch motion is independently performed.

(Yaw Motion)

FIGS. 17 and 18 are views illustrating a yaw motion of the multi-joint type surgical device illustrated in FIG. 4.

Referring to FIGS. 13, 14, 17, and 18 and the like, when the pulley 211, which is a driving part first jaw pulley, is rotated in the direction of an arrow A3 for a yaw motion, one of the wires 301 and 305, which are first jaw wires, is wound around the pulley 211 and the other one thereof is released from the pulley 211 in response to the rotation of the pulley 211. Accordingly, the pulley 111, which is an end tool first jaw pulley connected to the opposite side of the wires 301 and 305, is rotated in the direction of as arrow A4, so that the yaw motion is performed.

At this time, the pulley 219, the pulley 220, the pulley 229, and the pulley 230, which are driving part satellite pulleys, and the pulley 215, the pulley 216, the pulley 217, the pulley 218, the pulley 225, the pulley 226, the pulley 227, and the pulley 228, which are driving part relay pulleys, are not changed in position, but only the motion in which the wires 301 and 305 are wound around or released from the driving part satellite pulley and the driving part relay pulley occurs.

Accordingly, the driving part pitch pulley rigidly connected to the driving part satellite pulley is not rotated, and the wires 303 and 304, which are pitch wires, are not wound or released and maintained in position.

Similarly, when the pulley 221, which is a driving part second jaw pulley, is rotated for a yaw motion, in response to the rotation of the pulley 221, one of the wires 302 and 306, which are second jaw wires, is wound around the pulley 221 and the other one thereof is released from the pulley 221. Accordingly, the pulley 121, which is an end tool second jaw pulley connected to the opposite side of the wires 302 and 306, is rotated in one direction, so that the yaw motion is performed.

At this time, the pulley 219, the pulley 220, the pulley 229, and the pulley 230, which are driving part satellite pulleys, and the pulley 215, the pulley 216, the pulley 217, the pulley 218, the pulley 225, the pulley 226, the pulley 227, and the pulley 228, which are driving part relay pulleys, are not changed in position, but only the motion in which the wires 302 and 306 are wound around or released from the driving part satellite pulley and the driving part relay pulley occurs.

Accordingly, the driving part pitch pulley rigidly connected to the driving part satellite pulley is not rotated, and the wires 303 and 304, which are pitch wires, are not wound or released and maintained in position.

As a result, the overall lengths of the wire 301, the wire 302, the wire 305, and the wire 306, which are jaw wires, in the driving part 200 remain constant even when the pulley 211 or pulley 221, which is a driving part jaw pulley, is rotated for the yaw or actuation motion.

As described above, in the multi-joint type surgical device 30 according to an embodiment of the present disclosure, when the driving part pitch pulley is rotated, the driving part satellite pulley is revolved around the rotation shaft of the driving part pitch pulley to change the path length of the jaw wire wound around the driving part relay pulley, and the jaw wire is wound or released in response to the rotation of the driving part pitch pulley, so that the movement of the jaw wire due to the pitch drive may be offset or compensated, and as a result, the effect of separating the pitch motion and the yaw motion can be obtained.

Second Embodiment

Figure 19:
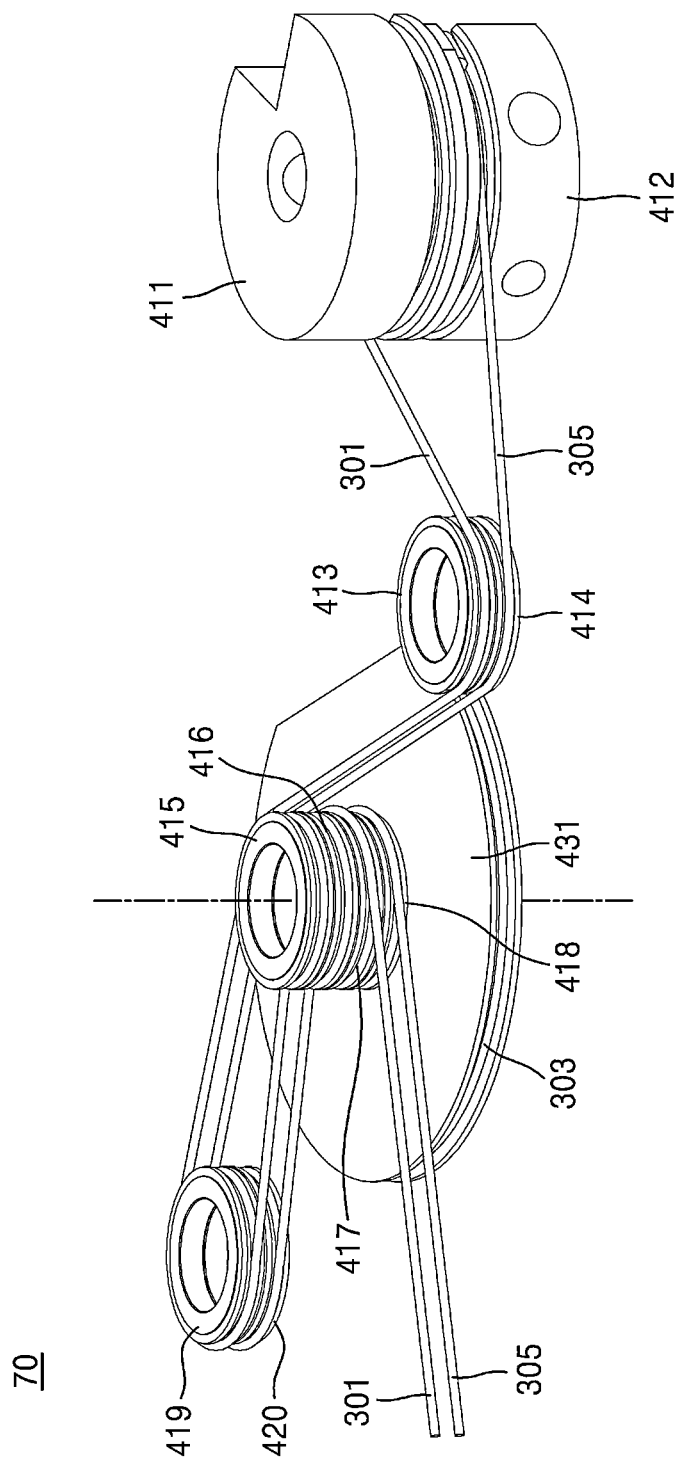
FIGS. 19 and 20 are conceptual diagrams illustrating a multi-joint type surgical device according to a second embodiment of the present disclosure.
Figure 20:
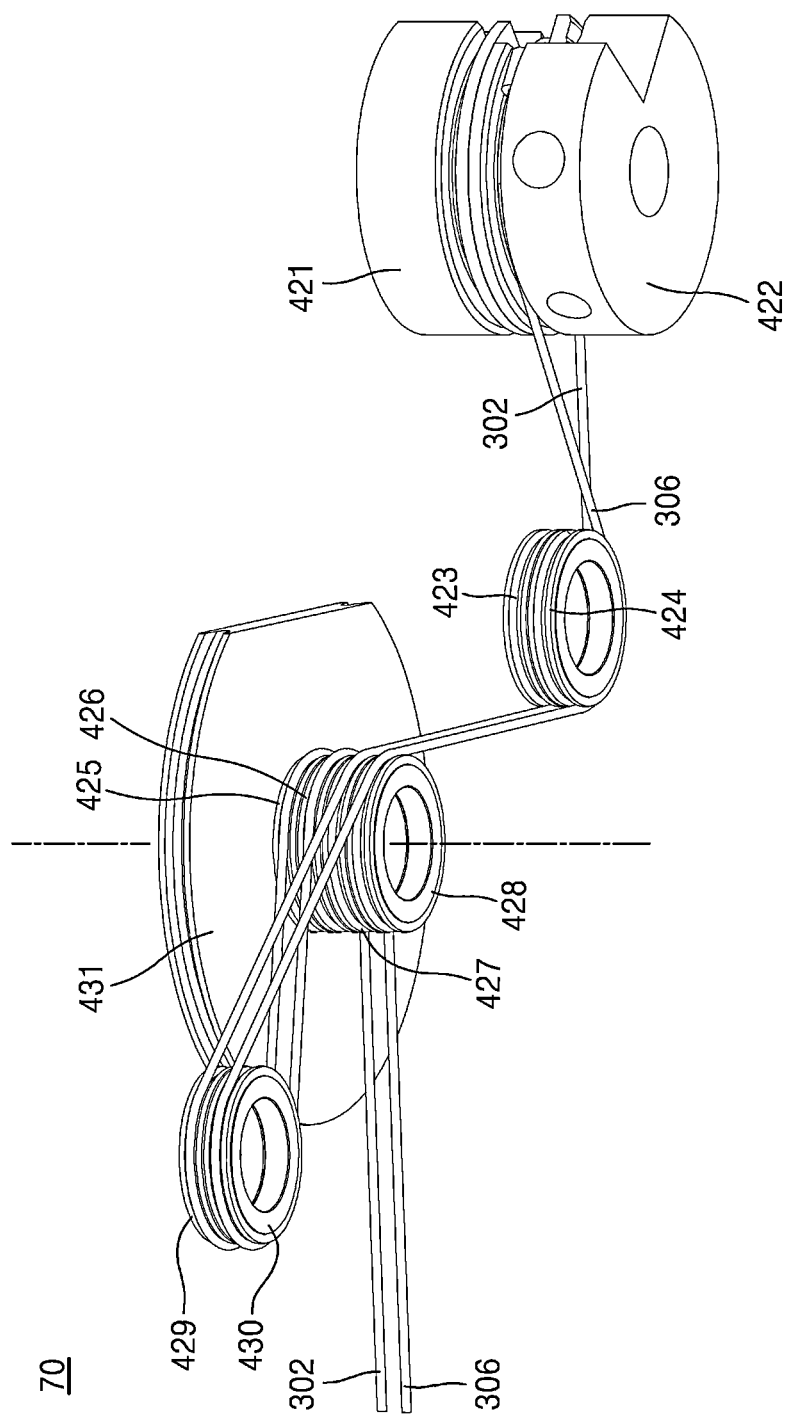

FIGS. 19 and 20 are conceptual diagrams illustrating a multi-joint type surgical device according to a second embodiment of the present disclosure.

A multi-joint type surgical device 70 according to the second embodiment of the present disclosure is different from the first embodiment illustrated in FIGS. 4 to 18 in that the configuration of driving part relay pulleys is different. The following description will focus on the difference from the first embodiment.

Referring to FIGS. 19 and 20, in the multi-joint type surgical device 70 according to the second embodiment of the present disclosure, a driving part first relay pulley and a driving part second relay pulley all have substantially the same diameter.

That is, a pulley 415 and a pulley 416, which are driving part first jaw first relay pulleys, and a pulley 417 and a pulley 418, which are driving part first jaw second relay pulleys, are all formed to have the same diameter. In addition, a pulley 425 and a pulley 426, which are driving part second jaw first relay pulleys, and a pulley 427 and a pulley 428, which are driving part second jaw second relay pulleys, may all be formed to have the same diameter as those of the driving part first jaw first relay pulleys and the driving part first jaw second relay pulleys.

In addition, the relationship of (diameter of end tool pitch pulley:diameter of end tool jaw pitch main pulley)=(diameter of driving part pitch pulley:diameter of driving part relay pulley) described in the first embodiment may also be established in the present embodiment.

For example, when a ratio of (diameter of end tool pitch pulley:diameter of end tool jaw pitch main pulley) is 6:4, a ratio of (diameter of driving part pitch pulley:diameter of driving part relay pulley) may also be 6:4.

In addition, here, the driving part relay pulley may include two or more pulleys including the driving part first relay pulley and the driving part second relay pulley. In addition, the sum of the diameters of the driving part first relay pulley and the driving part second relay pulley may be defined as the diameter of the driving part relay pulley.

In addition, a relationship of (rotation amount of driving part first relay pulley+rotation amount of driving part second relay pulley) may be described as being proportional to the rotation amount of the driving part pitch pulley.

However, although the ratio of (diameter of end tool pitch pulley:diameter of end tool jaw pitch main pulley) does not exactly match the ratio of (diameter of driving part pitch pulley:diameter of driving part relay pulley), when the pulley diameters are selected to make these ratios similar, the object of the present disclosure, which is to compensate for the movement of the jaw wire with the rotation of the driving part pitch pulley, can be achieved to some extent.

According to the present embodiment described above, using uniform-sized pulleys reduces the number of components, resulting in simplifying manufacturing and lowering costs.

Third Embodiment

Figure 21:
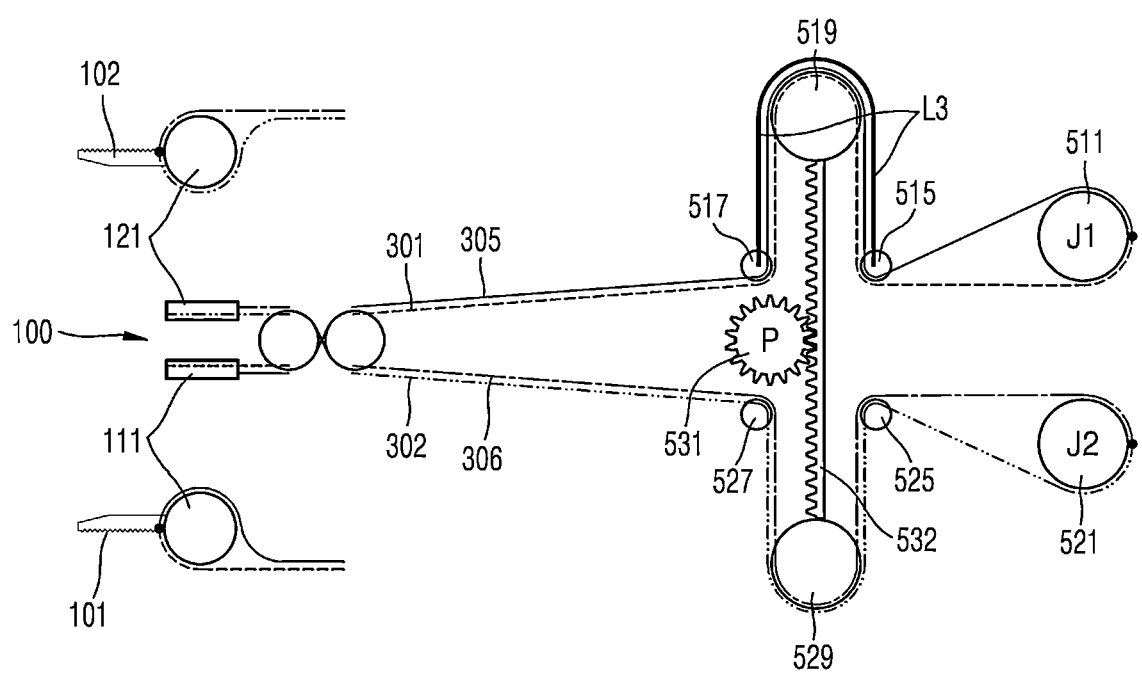
FIG. 21 is a conceptual diagram illustrating a multi-joint type surgical device according to a third embodiment of the present disclosure.
Figure 22:
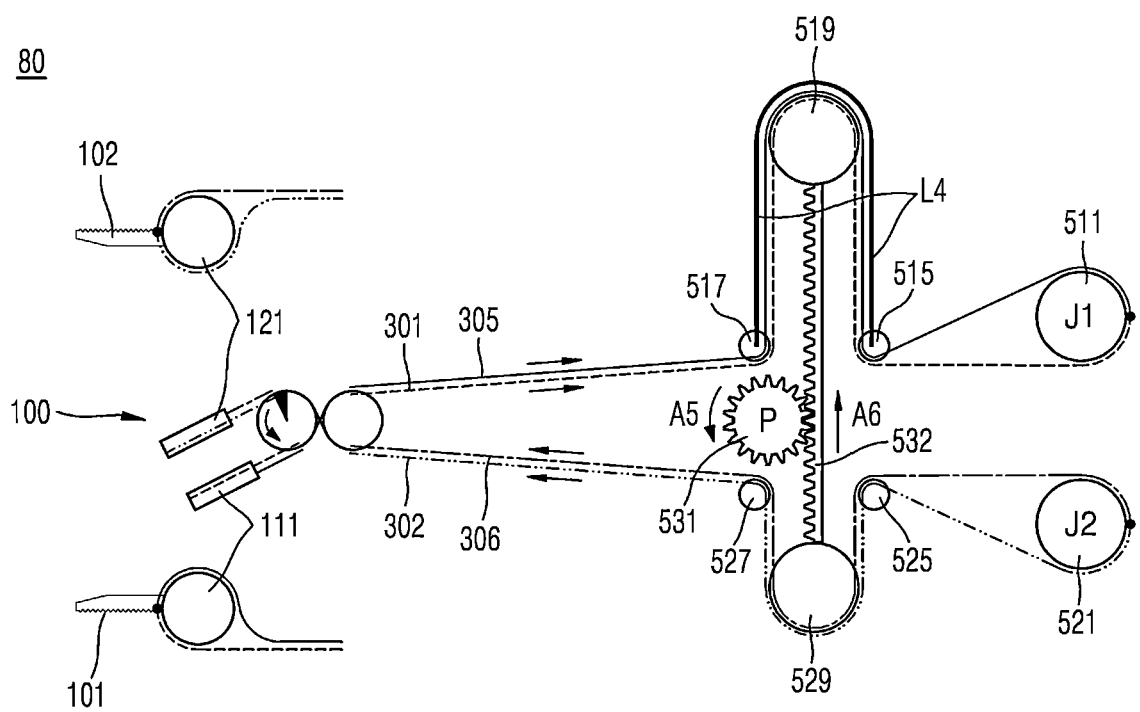
FIG. 22 is a conceptual diagram illustrating a pitch motion of the multi-joint type surgical device of FIG. 21.

FIG. 21 is a conceptual diagram illustrating a multi-joint type surgical device according to a third embodiment of the present disclosure, and FIG. 22 is a conceptual diagram illustrating a pitch motion of the multi-joint type surgical device of FIG. 21.

In order to change a path length of a jaw wire as a driving part pitch pulley is rotated, a multi-joint type surgical device 80 according to the third embodiment of the present disclosure adopts a rack/pinion structure. That is, in the present embodiment, the rotational motion described in the first embodiment of FIG. 4, which uses pulleys and wires, is replaced using a linear motion using a rack/pinion structure.

Referring to FIGS. 21 and 22, a driving part pitch gear 531 is formed to be rotatable together with a driving part pitch pulley (not shown) around the same shaft. In addition, a compensation gear 532 is formed at one side of the driving part pitch gear 531 so as to be engaged with the driving part pitch gear 531, and the compensation gear 532 is formed to translationally move up and down when the driving part pitch gear 531 is rotated together with the driving part pitch pulley (not shown). That is, the compensation gear serves as a kind of rack, and the pitch gear serves as a kind of pinion.

Meanwhile, the multi-joint type surgical device 80 according to the third embodiment of the present disclosure includes a driving part first jaw first relay pulley 515, a driving part first jaw second relay pulley 517, and a driving part first jaw satellite pulley 519, around which a wire 301/wire 305 that are first jaw wires are wound, In addition, the multi-joint type surgical device 80 includes a driving part second jaw first relay pulley 525, a driving part second jaw second relay pulley 527, and a driving part second jaw satellite pulley 529, around which a wire 302/wire 306 that are second jaw wires are wound.

Hereinafter, a pitch motion of the multi-joint type surgical device 80 according to the third embodiment of the present disclosure will be described.

Referring to FIGS. 21 and 22, the compensation gear 532 may be formed to translationally move in the direction of an arrow A6 of FIG. 20 when the driving part pitch gear 531 in the state of FIG. 21 is rotated in the direction of an arrow A5 of FIG. 22 together with the driving part pitch pulley (not shown).

In addition, as the compensation gear 532 is translationally moved as described above, path lengths of the wires 301 and 302, which are jaw wires, are changed.

That is, as compared to a path length L3 of the wire 301, which is first jaw wire, at the position of FIG. 21, a path length L4 of the first jaw wire at the position of FIG. 22 is increased, and the first jaw wire is further pulled at the driving part side by as much as the increased path length (L4−L3). As a result, the wire 301, which is a first jaw wire, is released at the end tool 100 side by as much as a length by which the wire 301, which is a first jaw wire, is pulled at the driving part 200 side, and as a result, thereby enabling a pitch motion.

Similarly, as compared to a path length of the wire 302, which is a second jaw wire, at the position of FIG. 21, a path length of the second jaw wire at the position of FIG. 22 is reduced, and the second jaw wire is further released at the driving part side by as much as the reduced path length. As a result, the wire 302, which is a second jaw wire, is wound at the end tool 100 side by as much as a length by which the wire 302, which is a second jaw wire, is released at the driving part 200 side, thereby enabling a pitch motion.

As described above, in the multi-joint type surgical device 80 according to the third embodiment of the present disclosure, when the driving part pitch gear 531 is rotated, the compensation gear 532 engaged with the driving part pitch gear 531 and the driving part satellite pulleys 519 and 529 connected to the compensation gear 532 are linearly moved to change the overall length of the jaw wire in the driving part, so that the jaw wire is wound and released in response to the rotation of the driving part pitch pulley, as a result, a pitch motion can be performed.

Fourth Embodiment

Figure 23:
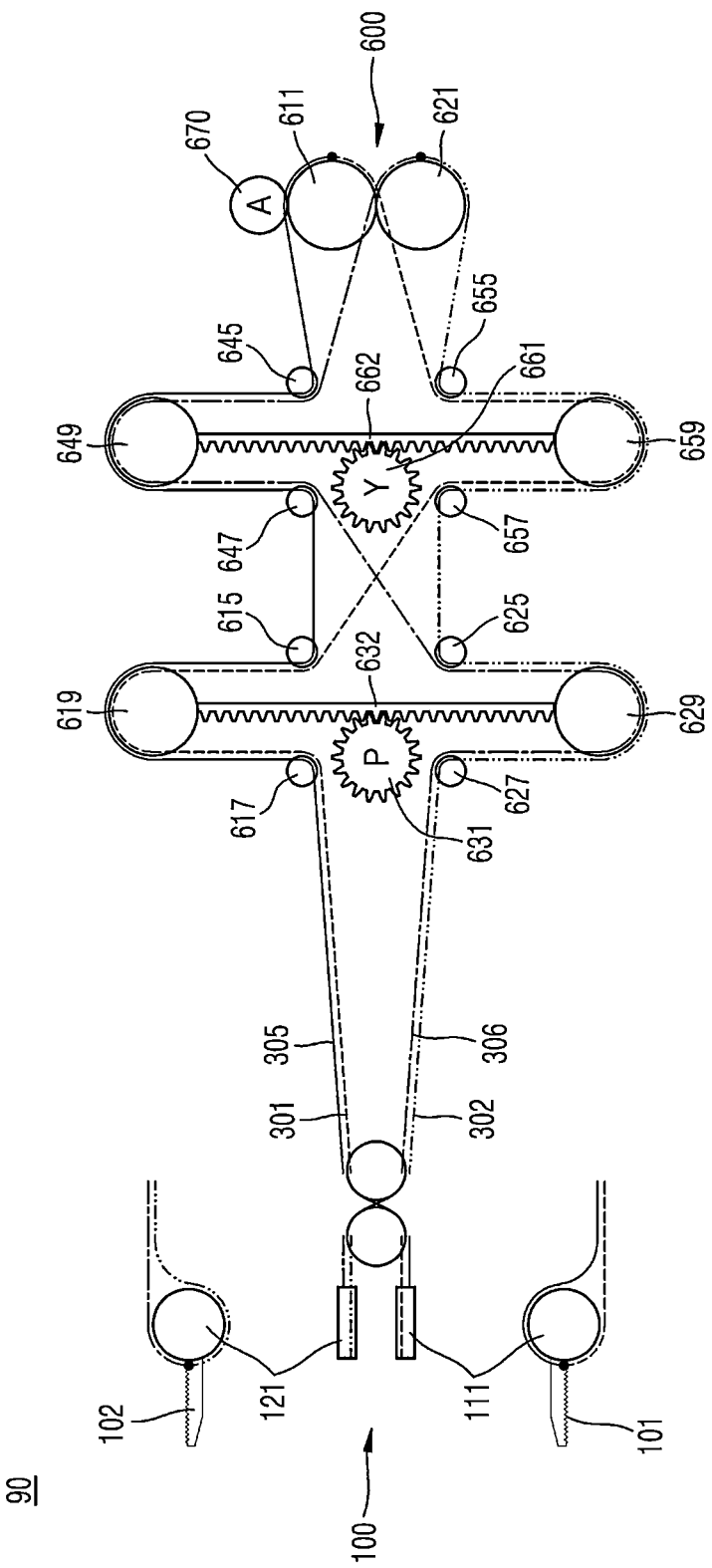
FIG. 23 is a conceptual diagram illustrating a multi-joint type surgical device according to a fourth embodiment of the present disclosure.
Figure 24:
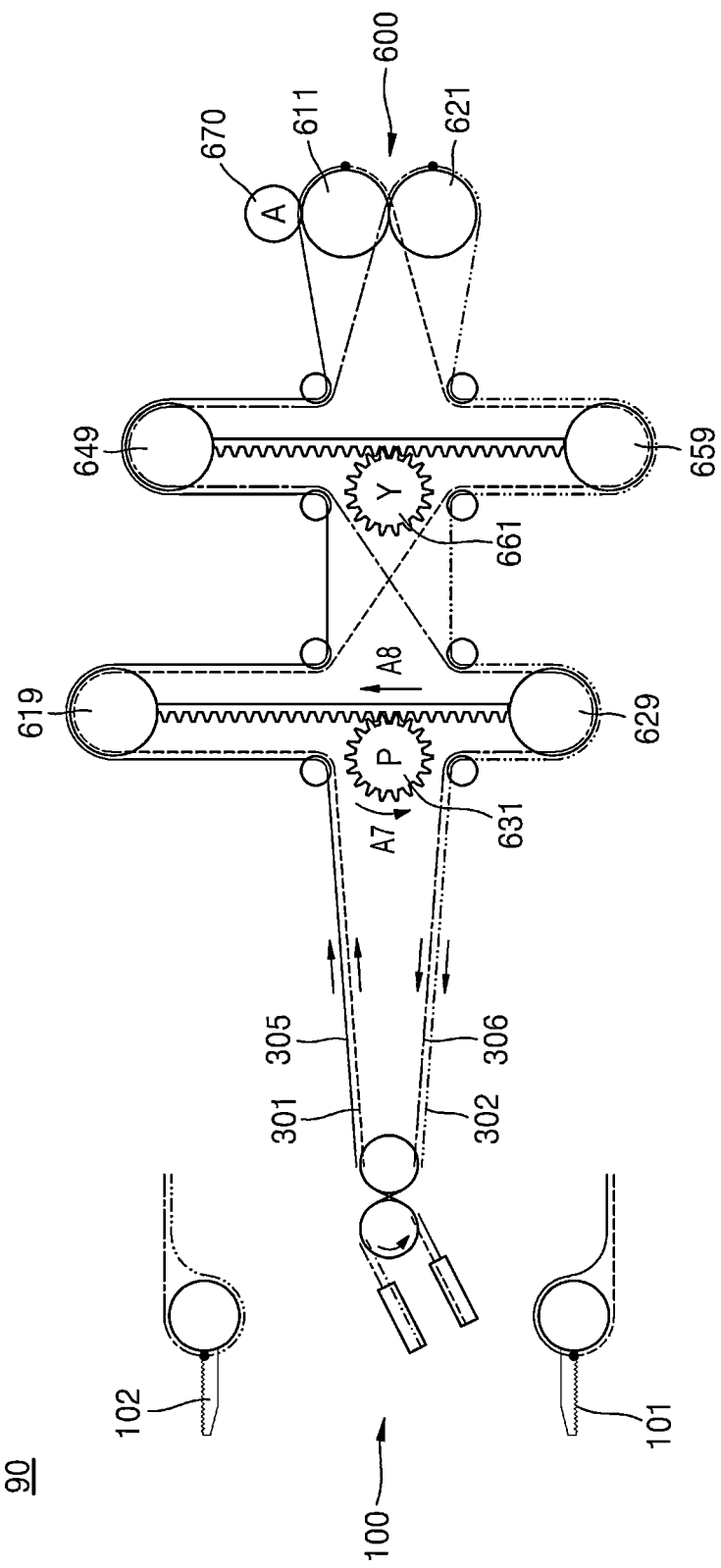
FIG. 24 is a conceptual diagram illustrating a pitch motion of the multi-joint type surgical device of FIG. 23.
Figure 25:
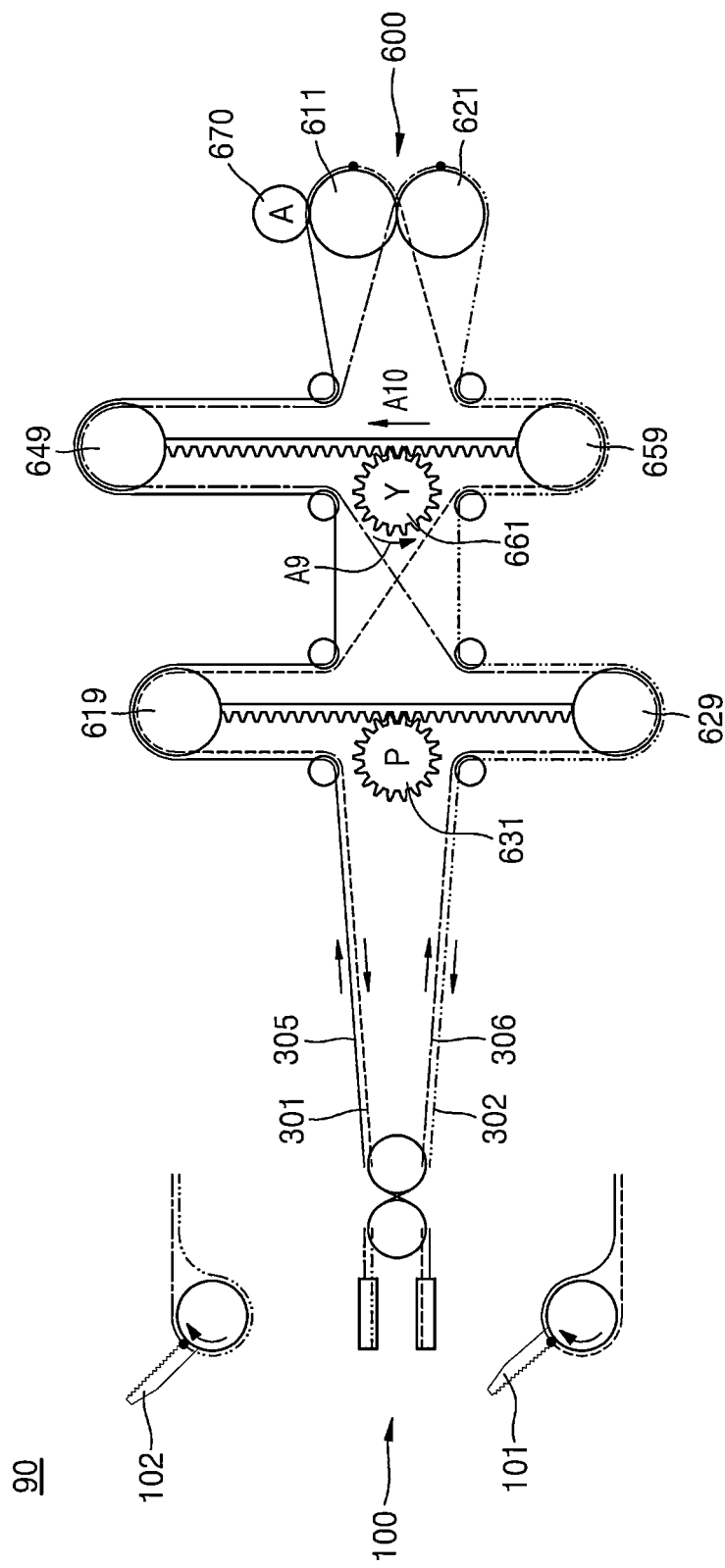
FIG. 25 is a conceptual diagram illustrating a yaw motion of the multi-joint type surgical device of FIG. 23.
Figure 26:
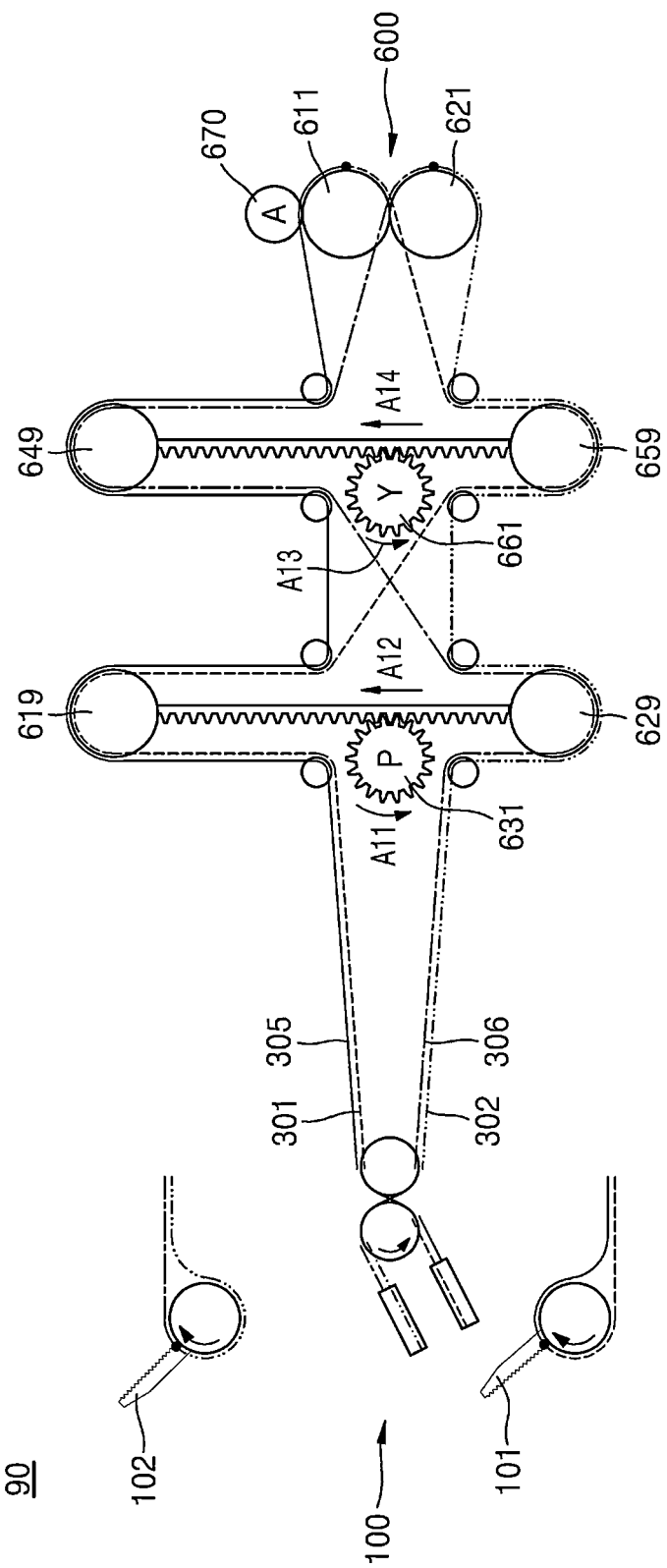
FIG. 26 is a conceptual diagram illustrating the multi-joint type surgical device of FIG. 23 simultaneously performing a pitch motion and a yaw motion.
Figure 27:
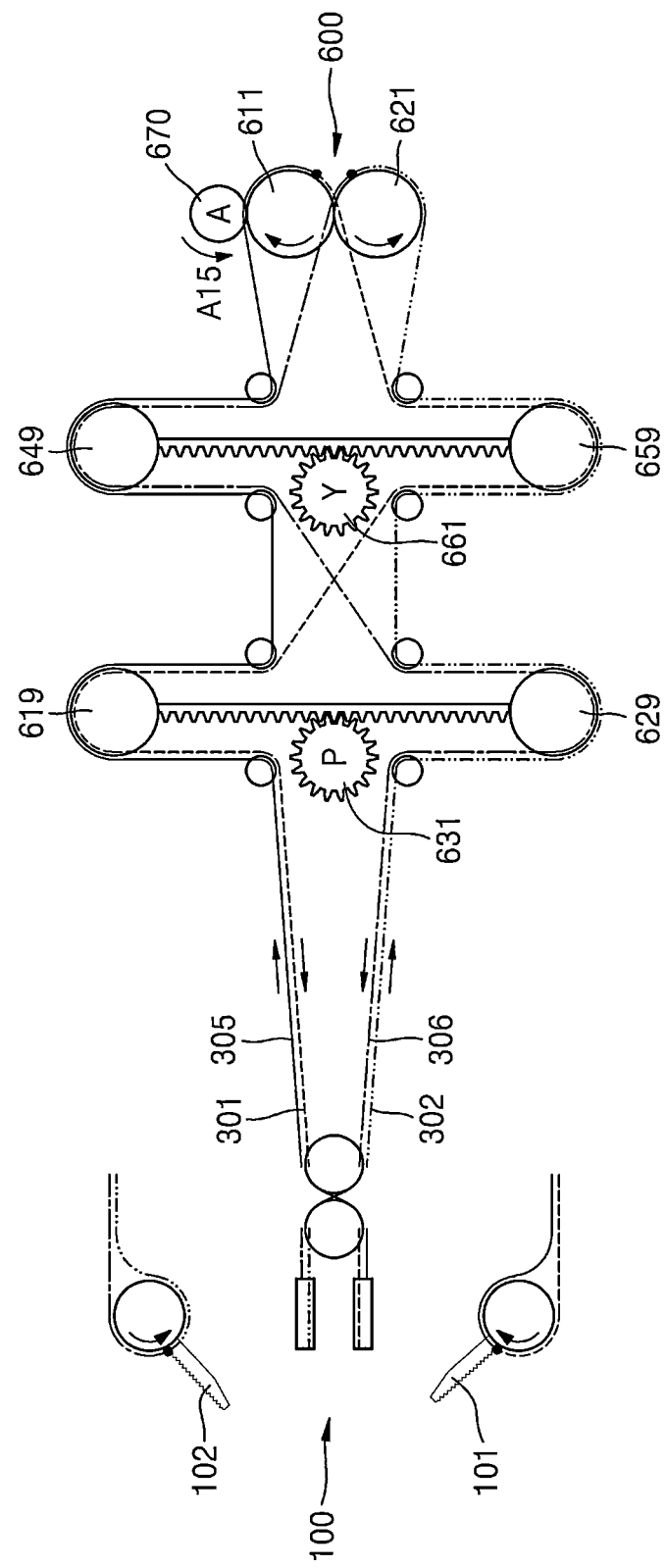
FIG. 27 is a conceptual diagram illustrating an actuation motion of the multi-joint type surgical device of FIG. 23.

FIG. 23 is a conceptual diagram illustrating a multi-joint type surgical device according to a fourth embodiment of the present disclosure, FIG. 24 is a conceptual diagram illustrating a pitch motion of the multi-joint type surgical device of FIG. 23, FIG. 25 is a conceptual diagram illustrating a yaw motion of the multi-joint type surgical device of FIG. 23, FIG. 26 is a conceptual diagram illustrating the multi-joint type surgical device of FIG. 23 simultaneously performing a pitch motion and a yaw motion, and FIG. 27 is a conceptual diagram illustrating an actuation motion of the multi-joint type surgical device of FIG. 23. In each drawing, a plan view of a pulley 111, which is a first jaw pulley, and a first jaw 101 connected to the pulley 111 is also illustrated at one side of the pulley 111, and a plan view of a pulley 121, which is a second jaw pulley, and a second jaw 102 connected to the pulley 121 is also illustrated at one side of the pulley 121.

In the first to third embodiments of the present disclosure described above, the pulley configuration of the driving part includes the driving part first jaw pulley for driving the first jaw, the driving part second jaw pulley for driving the second jaw, and the driving part pitch pulley for implementing a pitch motion. In addition, the motor connected to the driving part first jaw pulley is operated for the rotation (i.e., a yaw or actuation motion) of the first jaw, the motor connected to the driving part second jaw pulley is operated for the rotation (i.e., yaw or actuation motion) of the second jaw, and the motor connected to the driving part pitch pulley is operated for pitch rotation.

In contrast, a multi-joint type surgical device 90 according to the fourth embodiment of the present disclosure is configured with a driving part pitch pulley for driving a pitch motion, a driving part yaw pulley for driving a yaw motion, and a driving part actuation pulley for driving an actuation motion. In addition, a motor connected to the driving part pitch pulley is operated for pitch rotation, a motor connected to the driving part yaw pulley is operated for yaw rotation, and a motor connected to the driving part actuation pulley is operated for actuation rotation.

At this time, the configuration of each of the pulleys/wires for the pitch motion and the pulleys/wires for the yaw motion may be considered somewhat similar to that of the third embodiment described above.

Referring to FIG. 23, for a pitch motion, the multi-joint type surgical device 90 according to the fourth embodiment of the present disclosure includes a driving part pitch pulley (not shown), a driving part pitch gear 631, and a pitch compensation gear 632. Here, the driving part pitch pulley (not shown) and the driving part pitch gear 631 are formed to be rotatable together around the same shaft. In addition, the pitch compensation gear 632 is formed at one side of the driving part pitch gear 631 so as to be engaged with the driving part pitch gear 631, and the pitch compensation gear 632 is formed to translationally move up and down when the driving part pitch gear 631 is rotated together with the driving part pitch pulley (not shown). That is, the compensation gear serves as a kind of rack, and the pitch gear serves as a kind of pinion.

In addition, for a pitch motion, the multi-joint type surgical device 90 according to the fourth embodiment of the present disclosure includes a driving part first pitch first relay pulley 615, a driving part first pitch second relay pulley 617, and a driving part first pitch satellite pulley 619, around which a wire 301/wire 305 that are first jaw wires are wound. In addition, the multi-joint type surgical device 90 further includes a driving part second pitch first relay pulley 625, a driving part second pitch second relay pulley 627, and a driving part second pitch satellite pulley 629, around which a wire 302/wire 306 that are second jaw wires are wound. Meanwhile, although not illustrated in the drawings, each of the driving part relay pulley and the driving part satellite pulley may be provided in pairs so that both strands of each wire may be wound therearound.

Here, the driving part pitch gear 631 and the pulleys 615, 617, 625, and 627, which are driving part relay pulleys, may be formed such that relative positions thereof are fixed. In addition, the pulleys 619 and 629, which are driving part satellite pulleys, may be formed to be movable relative to the driving part pitch gear 631 and the driving part relay pulleys. When the driving part satellite pulleys are moved relative to the driving part pitch pulleys and the driving part relay pulleys as described above, the end tool performs pitch rotation as an overall length of the jaw wire in the driving part is changed.

Meanwhile, referring to FIG. 23, for a yaw motion, the multi-joint type surgical device 90 according to the fourth embodiment of the present disclosure includes a driving part yaw pulley (not shown), a driving part yaw gear 661, and a yaw compensation gear 662. Here, the driving part yaw pulley (not shown) and the driving part yaw gear 661 are formed to be rotatable together around the same shaft. In addition, a compensation gear 662 is formed at one side of the driving part yaw gear 661 so as to be engaged with the driving part yaw gear 661, and the compensation gear 662 is formed to translationally move up and down when the driving part yaw gear 661 is rotated together with the driving part yaw pulley (not shown). That is, the compensation gear serves as a kind of rack, and the yaw gear serves as a kind of pinion.

In addition, for a yaw motion, the multi-joint type surgical device 90 according to the fourth embodiment of the present disclosure includes a driving part first yaw first relay pulley 645, a driving part first yaw second relay pulley 647, and a driving part first yaw satellite pulley 649, around which a wire 305/wire 306 are wound. In addition, the multi-joint type surgical device 90 further includes a driving part second yaw first relay pulley 655, a driving part second yaw second relay pulley 657, and a driving part second yaw satellite pulley 659, around which the wire 301/wire 302 wound. Meanwhile, although not illustrated in the drawings, each of the driving part relay pulley and the driving part satellite pulley may be provided in pairs so that both strands of each wire may be wound therearound.

Here, the driving part yaw gear 661 and the pulleys 645, 647, 655, and 657, which are driving part relay pulleys, may be formed such that relative positions thereof are fixed. In addition, the pulleys 649 and 659, which are driving part satellite pulleys, may be formed to be movable relative to the driving part yaw gear 661 and the driving part relay pulleys. When the driving part satellite pulleys are moved relative to the driving part yaw pulleys and the driving part relay pulleys as described above, the end tool performs yaw rotation as the overall length of the jaw wire in the driving part is changed.

Hereinafter, a pitch motion of the multi-joint type surgical device 90 according to the fourth embodiment of the present disclosure will be described.

Referring to FIGS. 23 and 24, when the driving part pitch gear 631 in the state of FIG. 23 is rotated in the direction of an arrow A7 of FIG. 24 together with the driving part pitch pulley (not shown), the pitch compensation gear 632 may be translationally moved (linearly moved) in the direction of an arrow A8 of FIG. 24.

In addition, as the pitch compensation gear 632 is translationally moved as described above, path lengths of the wires 301 and 305, which are first jaw wires, and the wires 302 and 306, which are second jaw wires, are changed.

That is, as compared to the path lengths of the wires 301 and 305, which are first jaw wires, at the position of FIG. 23, the path lengths of the first jaw wires at the position of FIG. 24 are increased, and the first jaw wires are further pulled toward the driving part by as much as the increased path length. In other words, as the overall length of the first jaw wire in a driving part 600 is increased and the overall length of the first jaw wire in the end tool 100 is reduced in conjunction therewith, the first jaw 101 is rotated in a downward direction of FIG. 24.

Similarly, as compared to the path lengths of the wires 302 and 306, which are second jaw wires, at the position of FIG. 23, the path lengths of the second jaw wires at the position of FIG. 24 are further reduced, and the second jaw wires are further released at the driving part side by as much as the reduced path length. In other words, as the overall length of the second jaw wire in the driving part 600 is reduced, and the overall length of the second jaw wire in the end tool 100 is increased in conjunction therewith, the second jaw 101 is rotated in a downward direction of FIG. 24.

As a result, at the driving part 200 side, the wire 301/wire 305, which are first jaw wires, are pulled and the wire 302/wire 306, which are second jaw wires, are released, so that the pitch motion of the end tool 100 is enabled.

Hereinafter, a yaw motion of the multi-joint type surgical device 90 according to the fourth embodiment of the present disclosure will be described.

Referring to FIGS. 23 and 25, when the driving part yaw gear 661 in the state of FIG. 23 is rotated in the direction of an arrow A9 of FIG. 25 together with the driving part yaw pulley (not shown), the yaw compensation gear 662 is translationally moved (linearly moved) in the direction of an arrow A10 of FIG. 25.

In addition, as the yaw compensation gear 652 is translationally moved as described above, the path lengths of the wire 301, the wire 302, the wire 305, and the wire 306 are changed.

In detail, the wire 305 among the first jaw wires and the wire 306 among the second jaw wires are wound around the driving part first yaw satellite pulley 649, and the wire 301 among the first jaw wires and the wire 302 among the second jaw wires are wound around the driving part second yaw satellite pulley 659.

Thus, when the driving part yaw gear 661 is rotated in the direction of the arrow A9 of FIG. 25, and accordingly, the yaw compensation gear 662 is linearly move in the direction of the arrow A10 of FIG. 25, the path lengths of the wire 305 and the wire 306 wound around the driving part first yaw satellite pulley 649 are increased, and the path lengths of the wire 305 and the wire 306 wound around the driving part second yaw satellite pulley 659 are reduced.

That is, as compared to the path lengths of the wire 305 and the wire 306 at the position of FIG. 23, the path lengths of the wire 305 and the wire 306 at the position of FIG. 25 are further increased, and the wire 305 and the wire 306 are further pulled toward the driving part by as much as the increased path length. In other words, as the overall lengths of the wire 305 and the wire 306 in the driving part 600 is increased, and the overall lengths of the wire 305 and the wire 306 in the end tool 100 are reduced in conjunction therewith, the first jaw 101 is rotated in the clockwise direction when viewed from FIG. 25.

Similarly, as compared to the path lengths of the wires 301 and 302 at the position of FIG. 23, the path lengths of the wires 301 and 302 at the position of FIG. 25 are further reduced, and the wires 301 and 302 are further released at the driving part side by as much as the reduced path length. In other words, as the overall lengths of the wires 301 and 302 in the driving part 600 are reduced, and the overall lengths of the wires 301 and 302 in the end tool 100 are increased in conjunction therewith, the second jaw 102 is rotated in the clockwise direction when viewed from FIG. 25.

That is, when viewed from the end tool, among the first jaw wires, the wire 305 is pulled toward the driving part 200 and the wire 301 is released in the opposite direction, and thus, the first jaw 101 is rotated in the clockwise direction. Meanwhile, among the second jaw wires, the wire 306 is pulled and the wire 302 is released, and thus the second jaw 102 is rotated in the clockwise direction. As described above, as the first jaw 101 and the second jaw 102 are rotated in the same direction, the yaw motion is performed.

As a result, at the driving part 200 side, as the wire 305 and the wire 306 are pulled and the wire 301 and the wire 302 are released, the yaw motion of the end tool 100 is enabled.

Hereinafter, an actuation motion of the multi-joint type surgical device 90 according to the fourth embodiment of the present disclosure will be described.

Referring to FIGS. 23 and 27, a driving part actuation pulley 670, a pulley 611, which is a driving part first jaw pulley, and a pulley 621, which is a driving part second jaw pulley, are formed to be coupled to each other in the form of a gear or the like, so that when one pulley is rotated, the remaining pulleys are rotated together in conjunction with the one pulley.

When the driving part actuation pulley 670 in the state of FIG. 23 is rotated in the direction of an arrow A15 of FIG. 27, the pulley 611 and the pulley 612 are also rotationally moved in the arrow directions, respectively.

In addition, as the pulley 611 and the pulley 612 are rotationally moved as described above, the path lengths of the wire 301, the wire 302, the wire 305, and the wire 306 are changed.

In detail, the wires 301 and 305, which are first jaw wires, are wound around the pulley 611, and the wires 302 and 306, which are second jaw wires, are wound around the pulley 612. Accordingly, when the driving part actuation pulley 670 is rotated in the direction of the arrow A15 of FIG. 27, and accordingly, the pulley 611 and the pulley 612 are also rotationally moved in the arrow directions, respectively, which causes the wires 301 and 305 wound around the pulley 611 and the wires 302 and 306 wound around the pulley 612 to rotate along the respective pulleys as a whole.

That is, when viewed from the end tool, among the first jaw wires, the wire 305 is pulled toward the driving part 200 and the wire 301 is released in the opposite direction, and thus, the first jaw 101 is rotated in the clockwise direction. Meanwhile, among the second jaw wires, the wire 302 is pulled and the wire 306 is released, and thus the second jaw 102 is rotated in the clockwise direction. As described above, as the first jaw 101 and the second jaw 102 are rotated in opposite directions, the actuation motion is performed.

However, at this time, since the pulleys 619 and 629, which are driving part satellite pulleys, do not move with respect to the driving part pitch gear 631 and the driving part relay pulleys, and the pulleys 649 and 659, which are driving part satellite pulleys, do not move with respect to the driving part yaw gear 661 and the driving part relay pulleys, the overall length of each jaw wire in the driving part is not changed.

Meanwhile, the driving part pitch gear 631, the driving part pitch gear 631, and the driving part yaw gear 661 are formed to be rotatable independently of each other. Accordingly, in the present embodiment, the pitch motion and the yaw motion can be performed independently of each other and simultaneously.

For example, as shown in FIG. 26, when the driving part pitch gear 631 is rotated in the direction of an arrow A11 of FIG. 26 together with the driving part pitch pulley (not shown), the pitch compensation gear 632 is translationally moved (linearly moved) in the direction of an arrow A12 of FIG. 26. In addition, as the pitch compensation gear 632 is translationally moved as described above, the path lengths of the wires 301 and 305, which are first jaw wires, and the wires 302 and 306, which are second jaw wires, are changed. Accordingly, at the driving part 200 side, the wire 301/wire 305, which are first jaw wires, are pulled and the wire 302/wire 306, which are second jaw wires, are released, and as a result, the pitch motion of the end tool 100 is performed.

At the same time, as shown in FIG. 26, when the driving part yaw gear 661 is rotated in the direction of an arrow A13 of FIG. 26 together with the driving part yaw pulley (not shown), the yaw compensation gear 662 is translationally moved (linearly moved) in the direction of an arrow A14 of FIG. 26. In addition, as the yaw compensation gear 662 is translationally moved as described above, the path lengths of the wires 301 and 305, which are first jaw wires, and the wires 302 and 306, which are second jaw wires, are changed. As a result, at the driving part 200 side, as the wire 305 and the wire 306 are pulled and the wire 301 and the wire 302 are released, the yaw motion of the end tool 100 is performed.

As described above, in the multi-joint type surgical device 90 according to the fourth embodiment of the present disclosure. when the driving part pitch gear 531 is rotated, the compensation gear 532 engaged with the driving part pitch gear 531 and the driving part satellite pulleys 519 and 529 connected to the compensation gear 532 are linearly moved to change the overall length of the jaw wire in the driving part, so that the jaw wire is wound and unwound in response to the rotation of the driving part pitch pulley, as a result, a pitch motion can be performed.

Furthermore, the multi-joint type surgical device 90 according to the fourth embodiment of the present disclosure is configured with the driving part pitch pulley for driving a pitch motion, the driving part yaw pulley for driving a yaw motion, and the driving part actuation pulley for driving an actuation motion. In the first embodiment described above, the yaw motion and the actuation motion are performed by a combination of the rotation of the driving part first jaw pulley and the rotation of the driving part second jaw pulley, whereas in the present embodiment, as the yaw pulley and the actuation pulley are provided separately, the yaw motion and the actuation motion can be controlled independently, so that the input/output of the yaw motion and the input/output of the actuation motion can be controlled and measured independently. By separating driving components for a yaw motion and an actuation motion as described above, it is possible to obtain the effect of being able to implement force feedback for the operation of the end tool 100.

Fifth Embodiment

Figure 28:
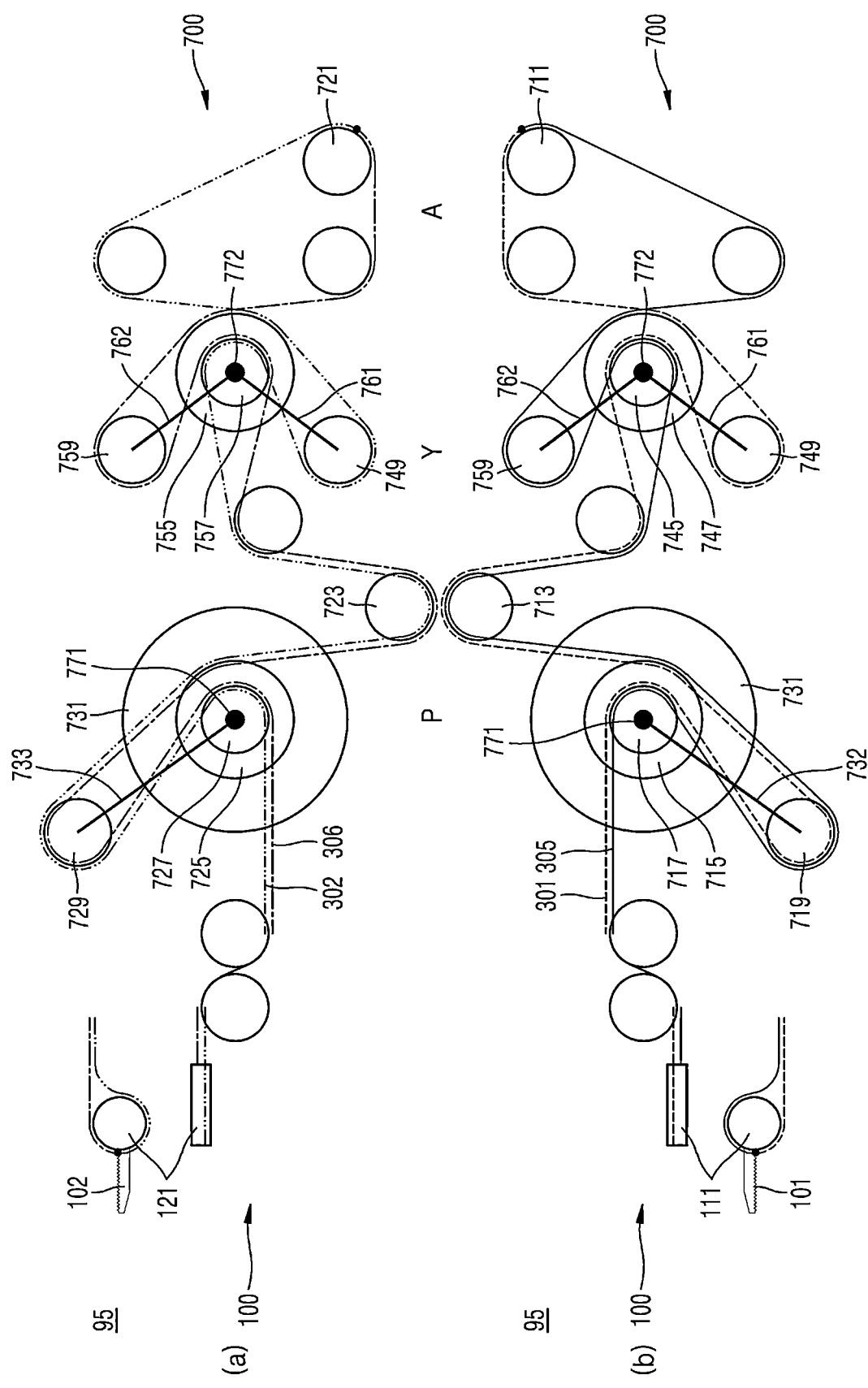
FIG. 28 is a conceptual diagram illustrating a multi-joint type surgical device according to a fifth embodiment of the present disclosure.
Figure 29:
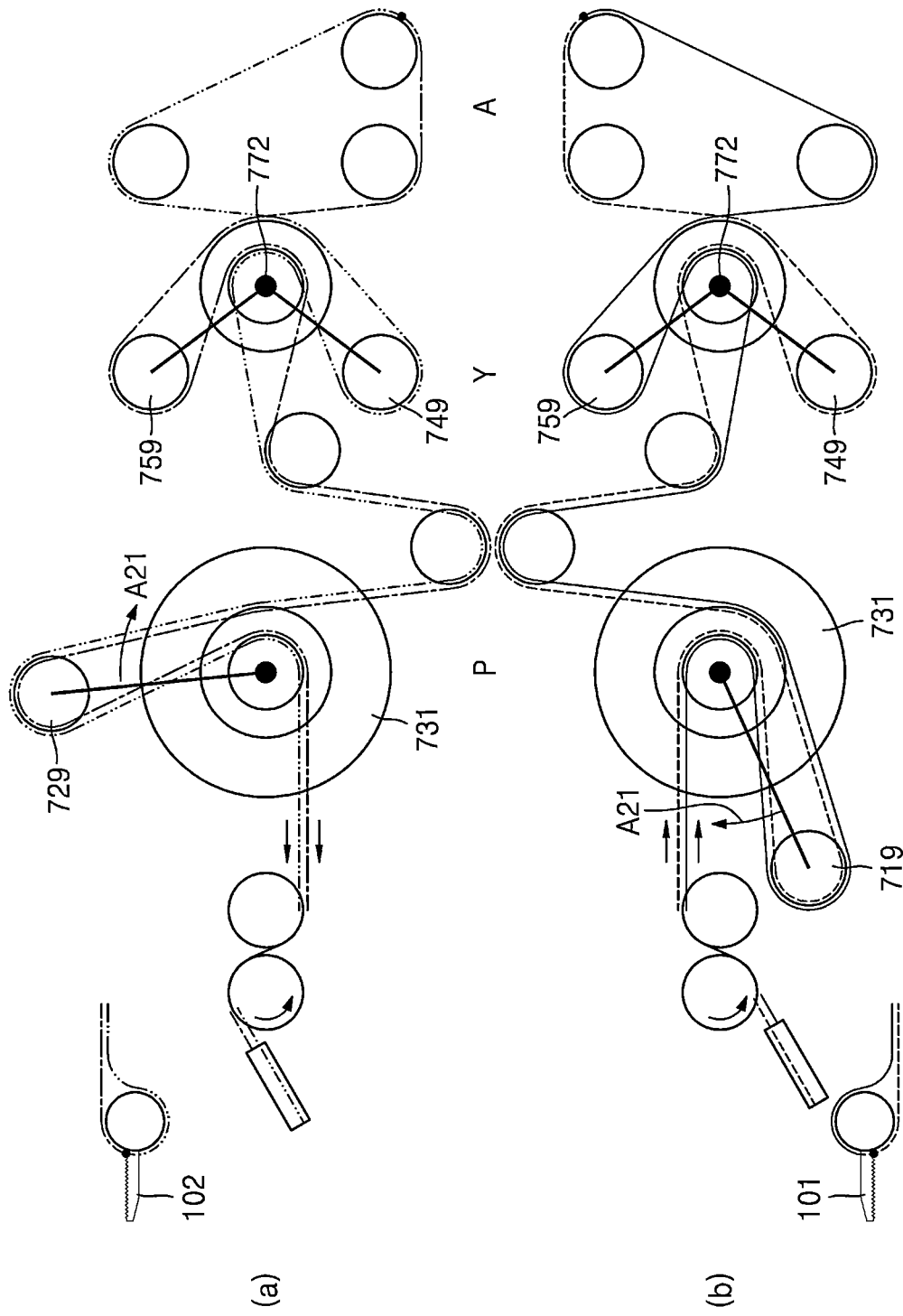
FIG. 29 is a conceptual diagram illustrating a pitch motion of the multi-joint type surgical device of FIG. 28.
Figure 30:
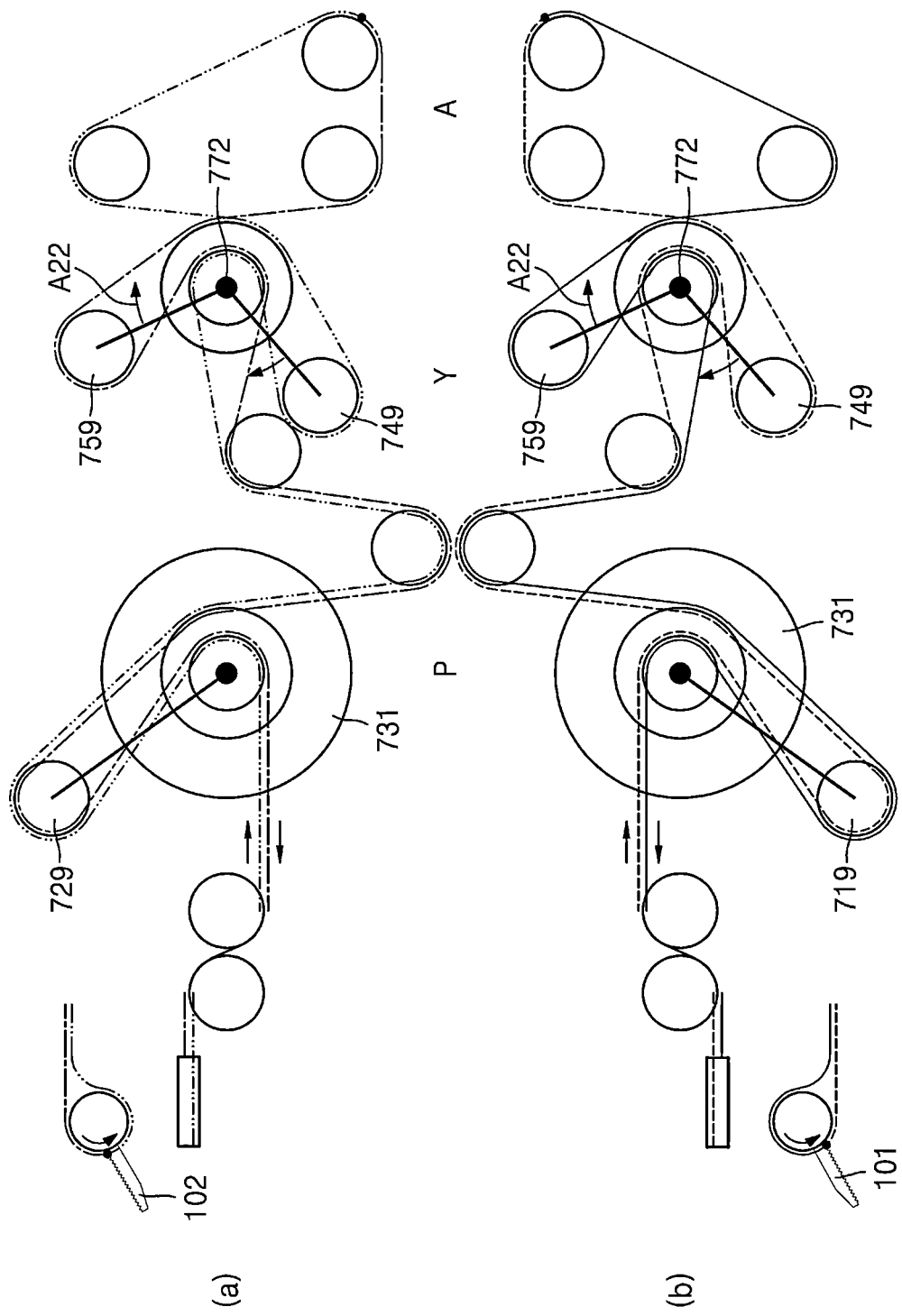
FIG. 30 is a conceptual diagram illustrating a yaw motion of the multi-joint type surgical device of FIG. 28.
Figure 31:
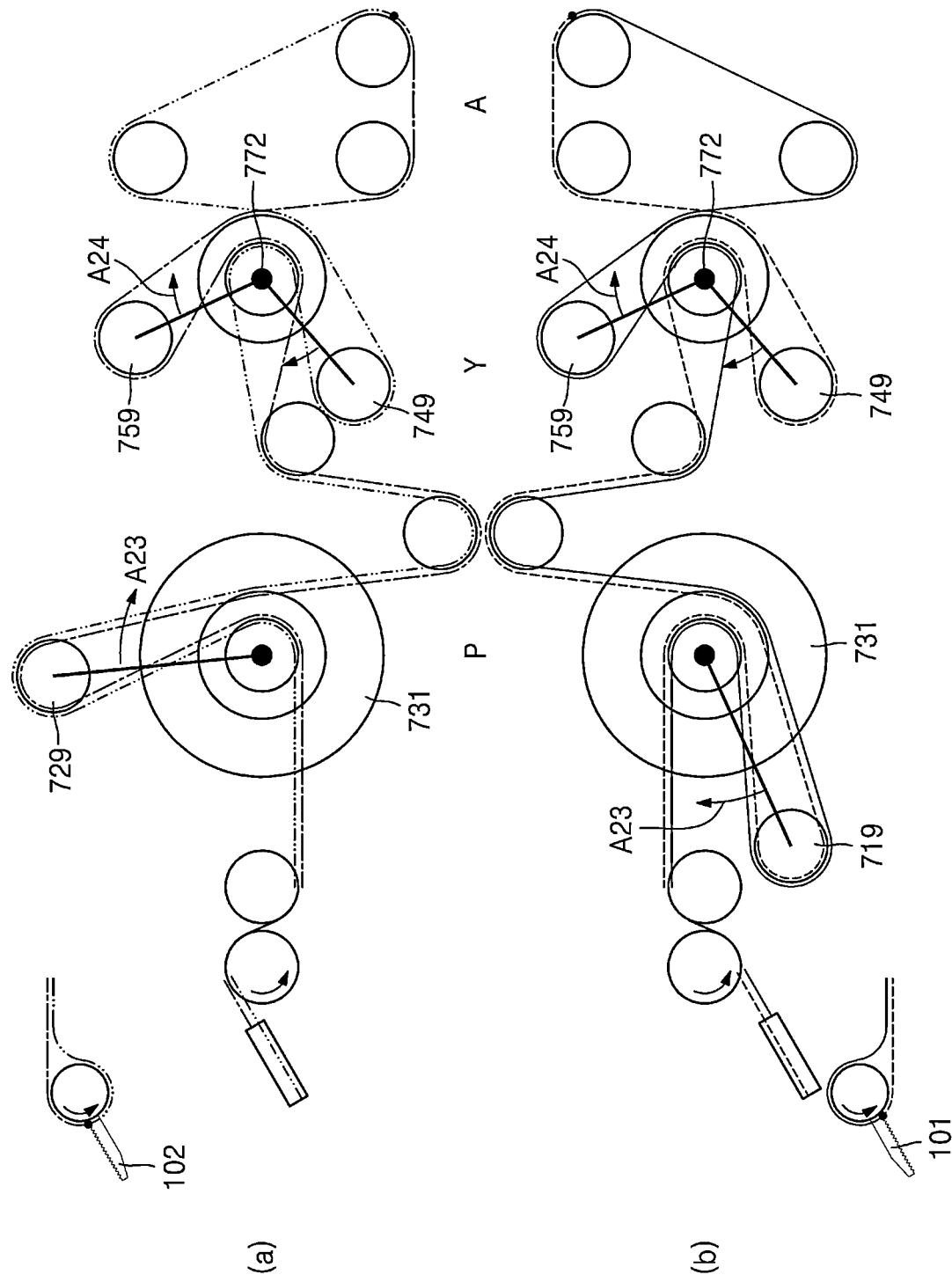
FIG. 31 is a conceptual diagram illustrating the multi-joint type surgical device of FIG. 28 simultaneously performing a pitch motion and a yaw motion.
Figure 32:
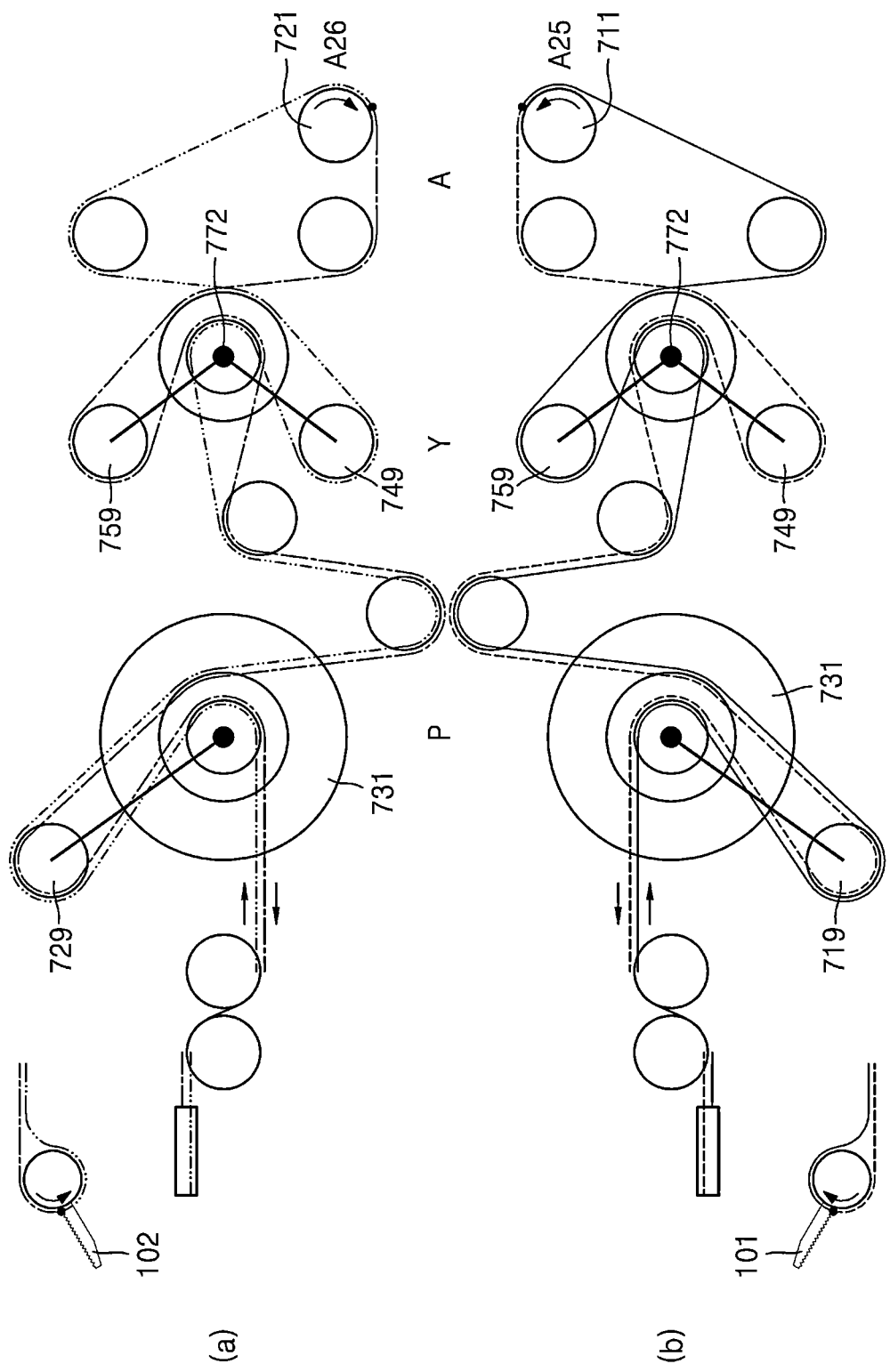
FIG. 32 is a conceptual diagram illustrating an actuation motion of the multi-joint type surgical device of FIG. 28.

FIG. 28 is a conceptual diagram illustrating a multi-joint type surgical device according to a fifth embodiment of the present disclosure, FIG. 29 is a conceptual diagram illustrating a pitch motion of the multi-joint type surgical device of FIG. 28, FIG. 30 is a conceptual diagram illustrating a yaw motion of the multi-joint type surgical device of FIG. 28, FIG. 31 is a conceptual diagram illustrating the multi-joint type surgical device of FIG. 28 simultaneously performing a pitch motion and a yaw motion, and FIG. 32 is a conceptual diagram illustrating an actuation motion of the multi-joint type surgical device of FIG. 28.

(A) of each drawing is a view illustrating a wire-pulley configuration related to a second jaw, and (B) of each drawing is a view illustrating a wire-pulley configuration related to a first jaw. In addition, in each drawing, a plan view of a pulley 111, which is a first jaw pulley, and a first jaw 101 connected to the pulley 111 is also illustrated at one side of the pulley 111, and a plan view of a pulley 121, which is a second jaw pulley, and a second jaw 102 connected to the pulley 121 is also illustrated at one side of the pulley 121.

In the first to third embodiments of the present disclosure described above, the pulley configuration of the driving part includes the driving part first jaw pulley for driving the first jaw, the driving part second jaw pulley for driving the second jaw, and the driving part pitch pulley for implementing a pitch motion. In addition, the motor connected to the driving part first jaw pulley is operated for the rotation (i.e., a yaw or actuation motion) of the first jaw, the motor connected to the driving part second jaw pulley is operated for the rotation (i.e., yaw or actuation motion) of the second jaw, and the motor connected to the driving part pitch pulley is operated for pitch rotation.

In contrast, a multi-joint type surgical device 95 according to the fifth embodiment of the present disclosure is configured with a driving part pitch rotation shaft for driving a pitch motion, a driving part yaw rotation shaft for driving a yaw motion, and a driving part actuation rotation shaft for driving an actuation motion. In addition, a motor connected to the driving part pitch rotation shaft is operated for pitch rotation, a motor connected to the driving part yaw rotation shaft is operated for yaw rotation, and a motor connected to the driving part actuation rotation shaft is operated for actuation rotation.

At this time, the configuration of each of the pulleys/wires for the pitch motion and the pulleys/wires for the yaw motion may be considered somewhat similar to that of the first embodiment described above.

Referring to FIG. 28, for a pitch motion, the multi-joint type surgical device 95 according to the fifth embodiment of the present disclosure includes a driving part first pitch first relay pulley 715, a driving part first pitch second relay pulley 717, a driving part first pitch satellite pulley 719, and a driving part first pitch auxiliary pulley 713, around which a wire 301/wire 305 that are first jaw wires are wound. In addition, the multi-joint type surgical device 95 further includes a driving part second pitch first relay pulley 725, a driving part second pitch second relay pulley 727, a driving part second pitch satellite pulley 729, and a driving part second pitch auxiliary pulley 723, around which a wire 302/wire 306 that are second jaw wires are wound. Meanwhile, although not illustrated in the drawings, each of the driving part relay pulley and the driving part satellite pulley may be provided in pairs so that both strands of each wire may be wound therearound.

In addition, for a pitch motion, the multi-joint type surgical device 95 according to the fifth embodiment of the present disclosure includes a driving part pitch rotation shaft 771, a driving part pitch pulley 731, a driving part pitch first connector 732, and a driving part pitch second connector 733.

Here, the driving part pitch first connector 732 and the driving part pitch second connector 733 may be formed to rotate together with the driving part pitch rotation shaft 771. That is, the driving part pitch pulley 731, the driving part pitch first connector 732, and the driving part pitch second connector 733 may be coupled to the driving part pitch rotation shaft 771 and rotated together with the driving part pitch rotation shaft 771.

In addition, the driving part first pitch satellite pulley 719 may be coupled to an end portion of the driving part pitch first connector 732. The driving part second pitch satellite pulley 729 may be coupled to an end portion of the driving part pitch second connector 733.

As a result, when the driving part pitch pulley 731 is rotated together with the driving part pitch rotation shaft 771, the pulleys 719 and 729, which are driving part satellite pulleys, are revolved around the driving part pitch rotation shaft 771. In other words, it may also be said that each of the pulleys 719 and 729 is rotated around the driving part pitch rotation shaft 771 as a whole, with a central axis of each of the pulleys 719 and 729 maintaining a certain distance from the driving part pitch rotation shaft 771, in a state in which the center of each of the pulleys 719 and 729 is spaced apart from the driving part pitch rotation shaft 771 by a certain extent.

That is, the driving part satellite pulley is formed to be movable relative to the driving part pitch pulley 731 so that the relative position of the driving part satellite pulley with respect to the driving part pitch pulley 731 may be changed. On the other hand, the relative positions of the driving part pitch pulley 731 and the driving part relay pulley remain constant.

In addition, when the driving part pitch pulley 731 is rotated around the driving part pitch rotation shaft 771, the pulleys 719 and 729, which are the driving part satellite pulleys, are moved relative to the driving part pitch pulley 731, which causes the overall lengths of the wire 301, the wire 302, the wire 305, and the wire 306, which are jaw wires, to be changed in a driving part 700, so that the end tool performs pitch rotation.

Meanwhile, referring to FIG. 28, for a yaw motion, the multi-joint type surgical device 95 according to the fifth embodiment of the present disclosure includes a driving part first yaw first relay pulley 745, a driving part first yaw second relay pulley 747, and a driving part first yaw satellite pulley 749, around which the wire 301/wire 302 are wound. In addition, the multi-joint type surgical device 95 further includes a driving part second yaw first relay pulley 755, a driving part second yaw second relay pulley 757, and a driving part second yaw satellite pulley 759, around which the wire 305/wire 306 wound. Meanwhile, although not illustrated in the drawings, each of the driving part relay pulley and the driving part satellite pulley may be provided in pairs so that both strands of each wire may be wound therearound.

In addition, for a yaw motion, the multi-joint type surgical device 95 according to the fifth embodiment of the present disclosure includes a driving part yaw rotation shaft 772, a driving part yaw first connector 761, and a driving part yaw second connector 762.

Here, the driving part yaw first connector 761 and the driving part yaw second connector 762 may be formed to rotate together with the driving part yaw rotation shaft 772.

In addition, the driving part first yaw satellite pulley 749 may be coupled to an end portion of the driving part yaw first connector 761. The driving part second yaw satellite pulley 759 may be coupled to an end portion of the driving part yaw second connector 762.

As a result, when the driving part yaw rotation shaft 772 is rotated, the pulleys 749 and 759, which are driving part satellite pulleys, are revolve around the driving part yaw rotation shaft 772. In other words, it may also be said that each of the pulleys 749 and 759 is rotated around the driving part yaw rotation shaft 772 as a whole, with a central axis of each of the pulleys 749 and 759 maintaining a certain distance from the driving part yaw rotation shaft 772, in a state in which the center of each of the pulleys 749 and 759 is spaced apart from the driving part yaw rotation shaft 772 by a certain extent.

That is, the driving part satellite pulley is formed to be movable relative to the driving part yaw rotation shaft 772 so that the relative position of the driving part satellite pulley with respect to the driving part yaw rotation shaft 772 may be changed. On the other hand, the relative positions of the driving part yaw rotation shaft 772 and the driving part relay pulley remain constant In addition, when the driving part yaw rotation shaft 772 is rotated, as the pulleys 749 and 759, which are driving part satellite pulleys, are moved relative to the driving part yaw rotation shaft 772, the overall lengths of the wire 301, the wire 302, the wire 305, and the wire 306, which are jaw wires, are changed in the driving part 700, so that the end tool performs yaw rotation.

Hereinafter, a pitch motion of the multi-joint type surgical device 95 according to the fifth embodiment of the present disclosure will be described.

Referring to FIGS. 28 and 29, when the driving part pitch pulley 731 in the state of FIG. 28 is rotated in the direction of an arrow A21 of FIG. 29, the driving part pitch first connector 732 and the driving part pitch second connector 733 are rotated in the direction of the arrow A21 together with the driving part pitch pulley 731. Accordingly, the driving part first pitch satellite pulley 719 fixedly coupled to the driving part pitch first connector 732 and the driving part second pitch satellite pulley 729 fixedly coupled to the driving part pitch second connector 733 are revolved as a whole in the direction of the arrow A21 around to the driving part pitch rotation shaft 771.

In addition, as the driving part first pitch satellite pulley 719 and the driving part second pitch satellite pulley 729 are revolved as described above, the path lengths of the wires 301 and 305, which are first jaw wires, and the wires 302 and 306, which are second jaw wires, are changed.

That is, as compared to the path lengths of the wires 301 and 305, which are first jaw wires, at the position of FIG. 28, the path lengths of the first jaw wires at the position of FIG. 29 are increased, and the first jaw wires are further pulled toward the driving part by as much as the increased path length. In other words, as the overall length of the first jaw wire in the driving part 700 is increased, and the overall length of the first jaw wire in the end tool 100 is reduced in conjunction therewith, the first jaw 101 is rotated in a downward direction of FIG. 29.

Similarly, as compared to the path lengths of the wires 302 and 306, which are second jaw wires, at the position of FIG. 28, the path lengths of the second jaw wires at the position of FIG. 29 are further reduced, and the second jaw wires are further released at the driving part side by as much as the reduced path length. In other words, as the overall length of the second jaw wire in the driving part 700 is reduced, and the overall length of the second jaw wire in the end tool 100 is increased in conjunction therewith, the second jaw 101 is rotated in the downward direction of FIG. 24.

As a result, at the driving part 700 side, the wire 301/wire 305, which are first jaw wires, are pulled and the wire 302/wire 306, which are second jaw wires, are released, so that the pitch motion of the end tool 100 is enabled.

Hereinafter, a yaw motion of the multi-joint type surgical device 95 according to the fifth embodiment of the present disclosure will be described.

Referring to FIGS. 28 and 30, when the driving part yaw rotation shaft 772 in the state of FIG. 28 is rotated in the direction of an arrow A22 of FIG. 30, the driving part yaw first connector 761 and the driving part yaw second connector 762 are rotated in the direction of the arrow A22 together with the driving part yaw rotation shaft 772. Accordingly, the driving part first yaw satellite pulley 749 fixedly coupled to the driving part yaw first connector 761 and the driving part second yaw satellite pulley 759 fixedly coupled to the driving part yaw second connector 762 are revolved as a whole in the direction of the arrow A22 around the driving part yaw rotation shaft 772.

In addition, as the driving part first yaw satellite pulley 749 and the driving part second yaw satellite pulley 759 are revolved as described above, the path lengths of the wire 301, the wire 302, the wire 305, and the wire 306 are changed.

In detail, the wire 305 among the first jaw wires and the wire 306 among the second jaw wires are wound around the driving part first yaw satellite pulley 749, and the wire 301 among the first jaw wires and the wire 302 among the second jaw wires are wound around the driving part second yaw satellite pulley 759.

Thus, when the driving part yaw rotation shaft 772 is rotated in the direction of the arrow A22 of FIG. 30, and accordingly, the driving part first yaw satellite pulley 749 and the driving part second yaw satellite pulley 759 are revolved as a whole in the direction of the arrow A22 around the driving part yaw rotation shaft 772, the path lengths of the wires 305 and 306 wound around the driving part first yaw satellite pulley 749 are reduced, and the path lengths of the wires 305 and 306 wound around the driving part second yaw satellite pulley 759 are increased.

That is, as compared to the path lengths of the wires 305 and 306 at the position of FIG. 28, the path lengths of the wires 305 and 306 at the position of FIG. 30 are further reduced, and the wires 305 and 306 are further released at the driving part side by as much as the reduced path length. In other words, as the overall lengths of the wires 305 and 306 in the driving part 700 are reduced, and the overall lengths of the wires 305 and 306 in the end tool 100 are increased in conjunction therewith, the first jaw 101 is rotated in the counterclockwise direction when viewed from FIG. 30.

Similarly, as compared to the path lengths of the wires 301 and 302 at the position of FIG. 28, the path lengths of the wires 301 and 302 at the position of FIG. 30 are further increased, and the wires 301 and 302 are further pulled toward the driving part by as much as the increased path length. In other words, as the overall lengths of the wires 301 and 302 in the driving part 700 are increased, and the overall lengths of the wires 301 and 302 in the end tool 100 are reduced in conjunction therewith, the second jaw 102 is rotated in the counterclockwise direction when viewed from FIG. 30.

That is, when viewed from the end tool, among the first jaw wires, the wire 301 is pulled toward the driving part 200 and the wire 305 is released in the opposite direction, and thus, the first jaw 101 is rotated in the counterclockwise direction. Meanwhile, among the second jaw wires, the wire 302 is pulled and the wire 306 is released, and thus the second jaw 102 is rotated in the counterclockwise direction. As described above, as the first jaw 101 and the second jaw 102 are rotated in the same direction, the yaw motion is performed.

As a result, at the driving part 200 side, as the wire 301 and the wire 302 are pulled and the wire 305 and the wire 306 are released, the yaw motion of the end tool 100 is enabled.

Hereinafter, an actuation motion of the multi-joint type surgical device 95 according to the fifth embodiment of the present disclosure will be described.

Referring to FIGS. 28 and 30, a driving part first jaw pulley 711 and a driving part second jaw pulley 721 are coupled to each other in the form of a gear or the like, so that, when one pulley is rotated, the other pulley is also rotated in conjunction with the one pulley.

In the state of FIG. 28, the driving part first jaw pulley 711 is rotated in the direction of an arrow A25, and the driving part second jaw pulley 721 is rotated in the direction of an arrow A26.

In addition, as the driving part first jaw pulley 711 and the driving part second jaw pulley 712 are rotationally moved as described above, the path lengths of the wires 301 and 302 and the wires 305 and 306 are changed.

In detail, the wires 301 and 305, which are first jaw wires, are wound around the pulley 711, and the wires 302 and 306, which are second jaw wires, are wound around the pulley 712. Accordingly, when the driving part first jaw pulley 711 is rotated in the direction of the arrow A25, which causes the wires 301 and 305 wound around the pulley 711 to be rotated as a whole along the pulleys, respectively. In addition, when the driving part first jaw pulley 721 is rotated in the direction of the arrow A26, which causes the wires 302 and 306 wound around the pulley 721 to be rotated as a whole along the pulleys, respectively.

That is, when viewed from the end tool, among the first jaw wires, the wire 305 is pulled toward the driving part 200 and the wire 301 is released in the opposite direction, and thus, the first jaw 101 is rotated in the clockwise direction. Meanwhile, among the second jaw wires, the wire 302 is pulled and the wire 306 is released, and thus the second jaw 102 is rotated in the counterclockwise direction. As described above, as the first jaw 101 and the second jaw 102 are rotated in opposite directions, the actuation motion is performed.

However, at this time, since the pulleys 719 and 729, which are driving part satellite pulleys, do not move with respect to the driving part pitch pulley 731 and the driving part relay pulleys, and the pulleys 749 and 759, which are driving part satellite pulleys, do not move with respect to the driving part yaw rotation shaft 772 and the driving part relay pulleys, the overall length of each jaw wire in the driving part is not changed.

Meanwhile, the driving part pitch rotation shaft 771 and the driving part yaw rotation shaft 772 are formed to be rotatable independently of each other. Accordingly, in the present embodiment, the pitch motion and the yaw motion can be performed independently of each other and simultaneously.

As described above, in the multi-joint type surgical device 95 according to the fifth embodiment of the present disclosure, when the driving part pitch pulley 731 is rotated, the driving part pitch pulley 731 and the driving part satellite pulleys 719 and 729 connected thereto are rotationally moved to change the overall length of the jaw wire in the driving part, so that the jaw wire is wound and released in response to the rotation of the driving part pitch pulley, as a result, a pitch motion can be performed.

Furthermore, the multi-joint type surgical device 95 according to the fifth embodiment of the present disclosure is configured with the driving part pitch rotation shaft for driving a pitch motion, the driving part yaw rotation shaft for driving a yaw motion, and the driving part actuation rotation shaft for driving an actuation motion. In the first embodiment described above, the yaw motion and the actuation motion are performed by a combination of the rotation of the driving part first jaw pulley and the rotation of the driving part second jaw pulley, whereas in the present embodiment, as the yaw rotation shaft and the actuation rotation shaft are provided separately, the yaw motion and the actuation motion can be controlled independently, so that the input/output of the yaw motion and the input/output of the actuation motion can be controlled and measured independently. By separating driving components for a yaw motion and an actuation motion as described above, it is possible to obtain the effect of being able to implement force feedback for the operation of the end tool 100.

As such, the present disclosure has been described with reference to the embodiments described with reference to the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL USABILITY

The present disclosure relates to a multi-joint type surgical device, and more particularly, may be used to a multi-joint type surgical device capable of being mounted on a robot arm or operated manually for use in laparoscopic surgery or various surgeries.

The invention claimed is:

1. A multi-joint type surgical device comprising a driving part configured to control a pitch rotation of an end tool,
   wherein the driving part includes:
   a driving part pitch relay pulley formed such that at least a portion of a wire is wound therearound; and
   a driving part pitch satellite pulley that changes a position thereof relative to the driving part pitch relay pulley by moving relative to the driving part pitch relay pulley while being spaced a certain distance from the driving part pitch relay pulley, and is formed such that at least a portion of the wire is wound therearound,
   wherein, when the driving part pitch satellite pulley is moved relative to the driving part pitch relay pulley, the pitch rotation of the end tool is controlled as an overall length of the wire in the driving part is changed.

2. The multi-joint type surgical device of claim 1, wherein, when the driving part pitch satellite pulley is moved relative to the driving part pitch relay pulley, the overall length of the wire in the driving part is changed as a path length of the wire wound around the driving part pitch relay pulley is changed.

3. The multi-joint type surgical device of claim 1, further comprising a driving part pitch pulley formed to be rotatable around a driving part pitch rotation shaft,
   wherein the driving part pitch satellite pulley is formed to be movable relative to the driving part pitch pulley, and when the driving part pitch pulley is rotated, a relative position of the driving part pitch satellite pulley with respect to the driving part pitch rotation shaft is changed.

4. The multi-joint type surgical device of claim 3, further comprising a driving part pitch connector that is rotated around the driving part pitch rotation shaft together with the driving part pitch pulley,
   wherein the driving part pitch satellite pulley is coupled to one end portion of the driving part pitch connector.

5. The multi-joint type surgical device of claim 3, wherein the driving part pitch pulley is formed to be rotatable around the driving part pitch rotation shaft, and
   the driving part pitch satellite pulley is formed to be revolvable around the driving part pitch rotation shaft.

6. The multi-joint type surgical device of claim 3, wherein
the wire includes a first wire and a second wire extending to the end tool through the driving part pitch relay pulley, and
when the driving part pitch rotation shaft is rotated, the first wire and the second wire are moved in a same direction.

7. The multi-joint type surgical device of claim 3, wherein the driving part additionally controls a yaw rotation of the end tool, and
the driving part includes:
a driving part yaw relay pulley formed such that at least a portion of the wire is wound therearound; and
a driving part yaw satellite pulley that changes a position thereof relative to the driving part yaw relay pulley by moving relative to the driving part yaw relay pulley while being spaced a certain distance from the driving part yaw relay pulley, and is formed such that at least a portion of the wire is wound therearound,
wherein, when the driving part yaw satellite pulley is moved relative to the driving part yaw relay pulley, the yaw rotation of the end tool is controlled as the overall length of the wire in the driving part is changed.

8. The multi-joint type surgical device of claim 7, further comprising a driving part yaw rotation shaft that is different from the driving part pitch rotation shaft,
wherein the driving part yaw satellite pulley is formed to be movable relative to the driving part yaw rotation shaft, and
when the driving part yaw rotation shaft is rotated, a relative position of the driving part yaw satellite pulley with respect to the driving part yaw rotation shaft is changed.

9. The multi-joint type surgical device of claim 8, wherein the driving part yaw satellite pulley includes:
a driving part first yaw satellite pulley formed such that at least a portion of a first wire of the wire is wound therearound; and
a driving part second yaw satellite pulley formed such that at least a portion of a second wire of the wire is wound therearound.

10. The multi-joint type surgical device of claim 9, wherein the driving part further includes a driving part yaw first connector and a driving part yaw second connector formed to rotate together with the driving part yaw rotation shaft,
wherein the driving part first yaw satellite pulley is coupled to one end portion of the driving part yaw first connector,
the driving part second yaw satellite pulley is coupled to one end portion of the driving part yaw second connector, and
when the driving part yaw rotation shaft is rotated, the driving part first yaw satellite pulley and the driving part second yaw satellite pulley are rotated together around the driving part yaw rotation shaft.

11. The multi-joint type surgical device of claim 9, wherein when the driving part yaw rotation shaft is rotated, the first wire and the second wire extending from the driving part to the end tool are moved in different directions from each other.

12. A multi-joint type surgical device comprising a driving part configured to control a pitch rotation and a yaw rotation of an end tool,
wherein the driving part includes:
a driving part relay pulley formed to be rotatable around a first shaft and formed such that at least a portion of a wire is wound therearound; and
a driving part satellite pulley that changes a position thereof relative to the driving part relay pulley by moving relative to the driving part relay pulley while being spaced a certain distance from the driving part relay pulley, and is formed such that at least a portion of the wire is wound therearound,
wherein, when the driving part satellite pulley is moved relative to the driving part relay pulley, the pitch rotation of the end tool is controlled as an overall length of the wire in the driving part is changed.

13. The multi-joint type surgical device of claim 12, wherein, when the driving part satellite pulley is moved relative to the driving part relay pulley, the overall length of the wire in the driving part is changed as a path length of the wire wound around the driving part relay pulley is changed.

14. The multi-joint type surgical device of claim 12, further comprising a driving part pitch pulley formed to be rotatable around the first shaft,
wherein the driving part satellite pulley is formed to be movable relative to the driving part pitch pulley, and
when the driving part pitch pulley is rotated, a relative position of the driving part satellite pulley with respect to the first shaft is changed.

15. The multi-joint type surgical device of claim 14, wherein, when the driving part pitch pulley is rotated, the driving part satellite pulley is moved in conjunction with the driving part pitch pulley.

16. The multi-joint type surgical device of claim 14, wherein, when the driving part pitch pulley is rotated around the first shaft, the overall length of the wire in the driving part is changed as the driving part satellite pulley is moved relative to the driving part pitch pulley.

17. The multi-joint type surgical device of claim 14, further comprising a pitch-yaw connector formed to rotate together with the driving part pitch pulley around the first shaft,
wherein the driving part satellite pulley is coupled to one end portion of the pitch-yaw connector.

18. The multi-joint type surgical device of claim 14, wherein
the driving part pitch pulley is formed to be rotatable around the first shaft, and
the driving part satellite pulley is formed to be revolvable around the first shaft.

19. The multi-joint type surgical device of claim 12, wherein the wire extends toward the end tool after being sequentially wound around the driving part relay pulley, the driving part satellite pulley, and the driving part relay pulley.

* * * * *